United States Patent
Bowen et al.

(10) Patent No.: US 11,466,268 B2
(45) Date of Patent: Oct. 11, 2022

(54) STRUCTURED SUBSTRATES FOR IMPROVING DETECTION OF LIGHT EMISSIONS AND METHODS RELATING TO THE SAME

(71) Applicant: Illumina, Inc., San Diego, CA (US)

(72) Inventors: M. Shane Bowen, Encinitas, CA (US); Dajun Yuan, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 17/247,731

(22) Filed: Dec. 21, 2020

(65) Prior Publication Data

US 2021/0130814 A1    May 6, 2021

Related U.S. Application Data

(63) Continuation of application No. 15/564,174, filed as application No. PCT/US2016/027399 on Apr. 14, 2016, now Pat. No. 10,900,030.

(Continued)

(51) Int. Cl.
*C12N 15/10* (2006.01)
*B82Y 15/00* (2011.01)
(Continued)

(52) U.S. Cl.
CPC .......... *C12N 15/1093* (2013.01); *B82Y 15/00* (2013.01); *B82Y 20/00* (2013.01);
(Continued)

(58) Field of Classification Search
CPC .... C12N 15/1093; B82Y 15/00; B82Y 20/00; B82Y 30/00; B82Y 40/00; C12Q 1/6816;
(Continued)

(56) References Cited

U.S. PATENT DOCUMENTS 5,599,675 A    2/1997   Brenner
5,750,341 A    5/1998   Macevicz
(Continued)

FOREIGN PATENT DOCUMENTS

CN    1823085 A1    8/2006
CN    101080500 A1    11/2007
(Continued)

OTHER PUBLICATIONS

Huh, et al., "Aptamer based surface enhanced Raman scattering detection of vasopressin using multilayer nanotube arrays", Biosensors and Bioelectronics 25(5), 1240-1243, 2010.
(Continued)

*Primary Examiner* — Benjamin R Whatley
*Assistant Examiner* — Jacqueline Brazin
(74) *Attorney, Agent, or Firm* — Illumina, Inc.

(57) ABSTRACT

A structured substrate includes a substrate body having an active side. The substrate body includes reaction cavities that open along the active side and interstitial regions that separate the reaction cavities. The structured substrate includes an ensemble amplifier positioned within each of the reaction cavities. The ensemble amplifier includes a plurality of nanostructures configured to at least one of amplify electromagnetic energy that propagates into the corresponding reaction cavity or amplify electromagnetic energy that is generated within the corresponding reaction cavity.

13 Claims, 22 Drawing Sheets

Related U.S. Application Data

(60) Provisional application No. 62/147,440, filed on Apr. 14, 2015.

(51) Int. Cl.
*B82Y 20/00* (2011.01)
*G03F 7/00* (2006.01)
*G01N 21/64* (2006.01)
*B82Y 40/00* (2011.01)
*B82Y 30/00* (2011.01)
*C12Q 1/6874* (2018.01)
*C12Q 1/6816* (2018.01)
*C12Q 1/6818* (2018.01)
*C12Q 1/6869* (2018.01)
*G01N 21/76* (2006.01)
*G01N 21/05* (2006.01)

(52) U.S. Cl.
CPC .............. *B82Y 30/00* (2013.01); *B82Y 40/00* (2013.01); *C12Q 1/6816* (2013.01); *C12Q 1/6818* (2013.01); *C12Q 1/6869* (2013.01); *C12Q 1/6874* (2013.01); *G01N 21/648* (2013.01); *G01N 21/6452* (2013.01); *G01N 21/6486* (2013.01); *G03F 7/0002* (2013.01); *B01J 2219/00317* (2013.01); *G01N 21/05* (2013.01); *G01N 21/6456* (2013.01); *G01N 21/76* (2013.01); *G01N 2021/6419* (2013.01); *G01N 2021/6441* (2013.01)

(58) Field of Classification Search
CPC .. C12Q 1/6818; C12Q 1/6869; C12Q 1/6874; G01N 21/6452; G01N 21/648; G01N 21/6486; G01N 21/05; G01N 21/6456; G01N 21/76; G01N 2021/6419; G01N 2021/6441; G03F 7/0002; B01J 2219/00317; B81C 1/00031
USPC ...................................................... 435/292.1
See application file for complete search history.

(56) References Cited

U.S. PATENT DOCUMENTS

| | | | |
|---|---|---|---|
| 6,210,891 | B1 | 4/2001 | Nyren et al. |
| 6,258,568 | B1 | 7/2001 | Nyren |
| 6,274,320 | B1 | 8/2001 | Rothberg et al. |
| 6,355,431 | B1 | 3/2002 | Chee et al. |
| 6,878,557 | B1* | 4/2005 | Zambias ................ C40B 50/08 506/25 |
| 6,890,741 | B2 | 5/2005 | Fan et al. |
| 6,913,884 | B2 | 7/2005 | Stuelpnagel et al. |
| 7,022,288 | B1 | 4/2006 | Boss et al. |
| 7,057,026 | B2 | 6/2006 | Barnes et al. |
| 7,211,414 | B2 | 5/2007 | Hardin et al. |
| 7,244,559 | B2 | 7/2007 | Rothberg et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 7,582,420 | B2 | 9/2009 | Oliphant et al. |
| 7,595,883 | B1 | 9/2009 | El Gamal et al. |
| 7,785,790 | B1 | 8/2010 | Church et al. |
| 8,003,316 | B2* | 8/2011 | Frasch ...................... B82Y 5/00 435/6.11 |
| 8,039,817 | B2 | 10/2011 | Feng et al. |
| 8,535,616 | B2 | 9/2013 | Blair et al. |
| 8,586,368 | B2 | 11/2013 | Superfine et al. |
| 8,895,249 | B2 | 11/2014 | Shen et al. |
| 8,906,320 | B1 | 12/2014 | Eltoukhy et al. |
| 2005/0053980 | A1 | 3/2005 | Gunderson et al. |
| 2005/0181440 | A1 | 8/2005 | Chee et al. |
| 2005/0191698 | A1 | 9/2005 | Chee et al. |
| 2005/0244870 | A1 | 11/2005 | Chee et al. |
| 2008/0108082 | A1 | 5/2008 | Rank et al. |
| 2008/0240543 | A1* | 10/2008 | Budach ............... G01N 21/6428 382/141 |
| 2008/0297802 | A1 | 12/2008 | Ogawa et al. |
| 2009/0186349 | A1 | 7/2009 | Gunderson et al. |
| 2009/0272914 | A1 | 11/2009 | Feng et al. |
| 2010/0111768 | A1 | 5/2010 | Banerjee et al. |
| 2011/0059865 | A1 | 3/2011 | Smith et al. |
| 2011/0312529 | A1 | 12/2011 | He et al. |
| 2012/0270305 | A1 | 10/2012 | Reed et al. |
| 2012/0316086 | A1 | 12/2012 | Lin et al. |
| 2013/0085073 | A1 | 4/2013 | Meuleman et al. |
| 2013/0116153 | A1 | 5/2013 | Bowen et al. |
| 2013/0165328 | A1 | 6/2013 | Previte et al. |
| 2013/0260479 | A1* | 10/2013 | Chou ................... G01N 21/648 436/501 |
| 2013/0261028 | A1 | 10/2013 | Triener et al. |
| 2013/0278928 | A1 | 10/2013 | Mourey et al. |
| 2014/0079923 | A1 | 3/2014 | George et al. |
| 2014/0154668 | A1 | 6/2014 | Chou et al. |
| 2014/0242334 | A1 | 8/2014 | Naraghi |
| 2014/0243224 | A1 | 8/2014 | Barnard et al. |
| 2016/0053252 | A1 | 2/2016 | Von Hatten et al. |
| 2016/0363728 | A1* | 12/2016 | Wang ...................... G02B 6/124 |

FOREIGN PATENT DOCUMENTS

| | | |
|---|---|---|
| CN | 101939329 A1 | 1/2011 |
| CN | 102666946 A1 | 9/2012 |
| CN | 103364544 A1 | 10/2013 |
| WO | 1989/010977 A1 | 11/1989 |
| WO | 1991/006678 A1 | 5/1991 |
| WO | 2004/018497 A2 | 3/2004 |
| WO | 2005/065814 A1 | 7/2005 |
| WO | 2007/123744 A2 | 11/2007 |
| WO | 2012/058096 A1 | 5/2012 |
| WO | 2014/121156 A1 | 8/2014 |
| WO | 2015/089092 A1 | 6/2015 |
| WO | 2015/100373 A1 | 7/2015 |

OTHER PUBLICATIONS

Bains, et al., "A novel method for nucleic acid sequence determination" J. Theor Biol., 135 (3), 303-307, 1988.
Bentley, et al., "Accurate whole human genome sequencing using reversible terminator chemistry" Nature, 456, 53-59, 2008.
Bowen, "Enhancing DNA Cluster Fluorescence Using Localized Surface Plasmmon Resonance", U.S. Appl. No. 61/920,244, 40 pages.
Duijs, Authorized Officer, European Patent Office, International Search Report, International Patent Application No. PCT/US2016/027399, dated Sep. 29, 2016, 5 pages.
Drmanac, et al., "Accurate sequencing by hybridization for DNA diagnostics and individual genomics" Nature Biotechnology, 16 (1), 54-58, 1998.
Fodor, et al., "Light-Directed, Spatially Addressable Parallel Chemical Synthesis" Science, 251, 767-773, 1991.
Gaspar, D. et al., Influence of the layer thickness in plasmonic gold nanoparticles produced by thermal evaporation, Scientific Reports 3 (1469), 1-5, 2013.
Korlach, et al., "Selective aluminum passivation for targeted immobilization of single DNA polymerase molecules in zero-mode waveguide nanostructures" PNAS, 105(4), 1176-1181, Jan. 29, 2008.
Levene, et al., "Zero-Mode Waveguides for Single-Molecule Analysis at High Concentrations" Science, 299, 682-686, Jan. 31, 2003.
Lucas, B. et al., "Nanoimprint Lithography Based Approach for the Fabrication of Large-Area, Uniformly-Oriented Plasmonic Arrays" Advanced Materials 20, 1129-1134, 2008.
Lundquist, et al., "Parallel confocal detection of single molecules in real time" Optics Letters, 33(9), 1026-1028, May 1, 2008.
Ronaghi, et al., "A Sequencing Method Based on Real-Time Pyrophosphate" Science, 281 (5375), 363-365, Jul. 17, 1998.
Ronaghi, et al., "Real-time DNA Sequencing Using Detection of Pyrophosphate Release" Analytical Biochemistry, 24, 84-89, 1996.

(56) References Cited

OTHER PUBLICATIONS

Ronaghi, M., "Pyrosequencing sheds light on DNA sequencing" Genome Research, 11, 3-11, 2001.
Rybenkov, et al., "Probability of DNA knotting and the effective diameter of the DNA double helix" Proc. Natl. Acad. Sci. USA, 90, 5307-531, 1993.
Shendure, et al., "Accurate Multiplex Polony Sequencing of an Evolved Bacterial Genome" Science, 309 (5741), 1728-1732, 2005.
Sobel, et al., "Effects of Na+ on the persistence length and excluded volume of T7 bacteriophage DNA" Biopolymers, 31,1559-1564, 1991.
Zimmerman, et al., "Estimation of macromolecule concentrations and excluded volume effects for the cytoplasm of *Escherichia coli*" J. Mol. Biol. 222, 599-620, 1991.

* cited by examiner

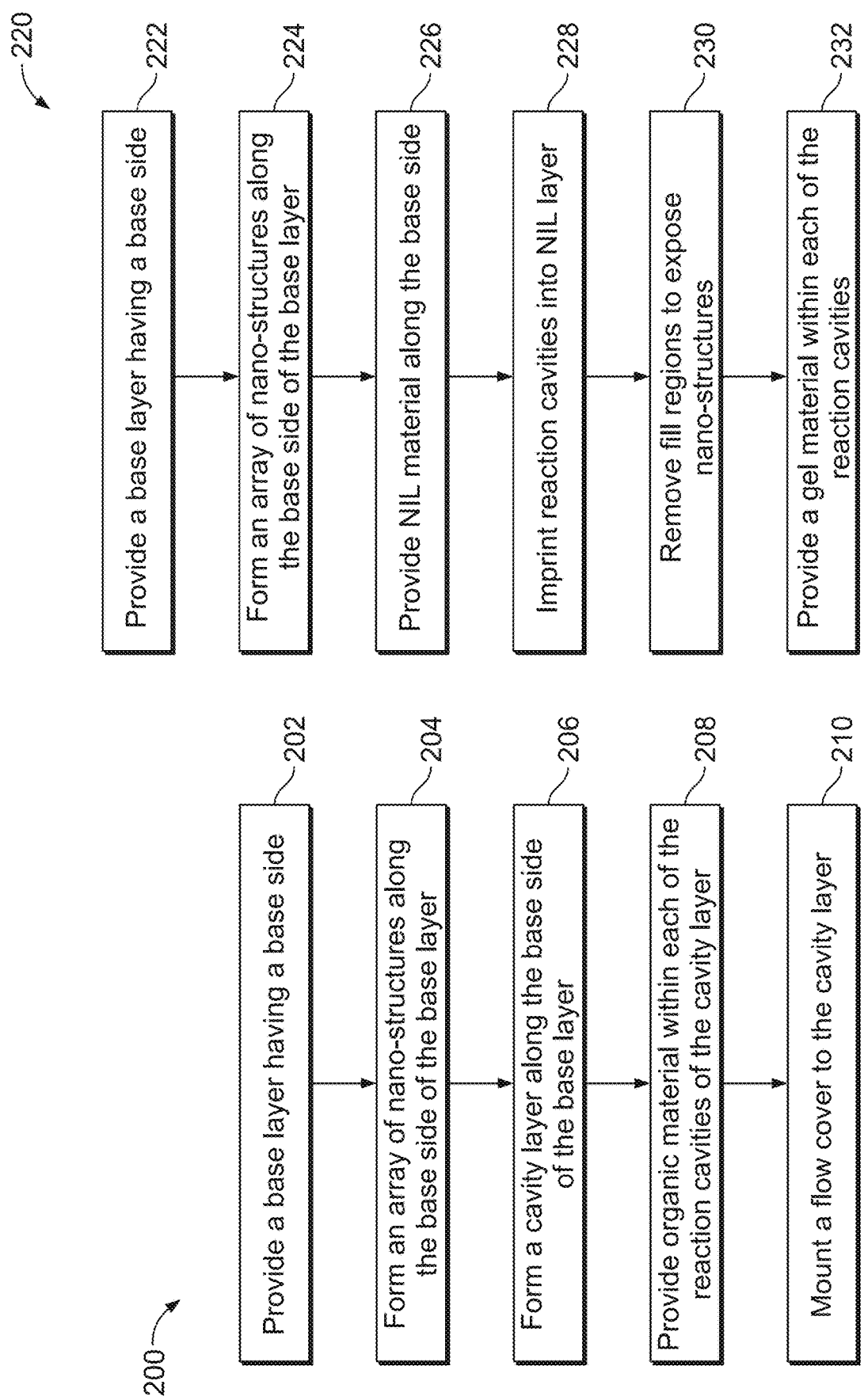

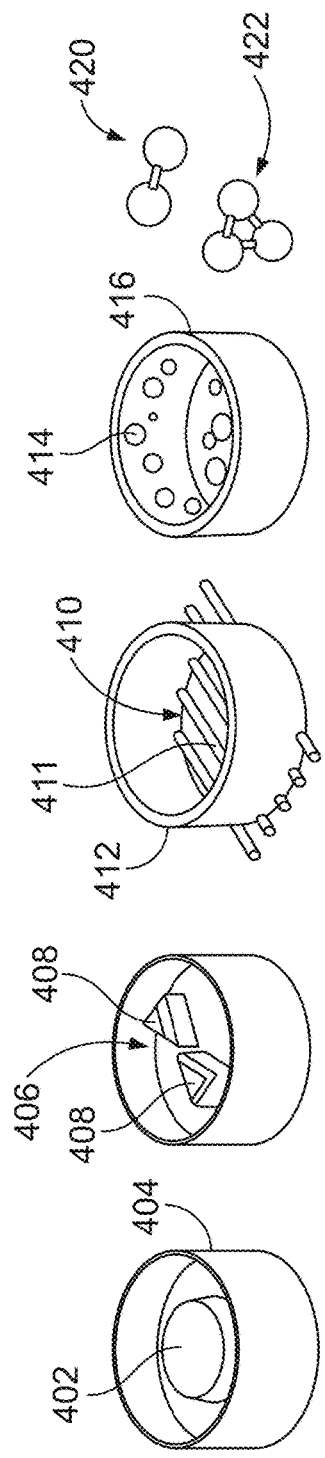
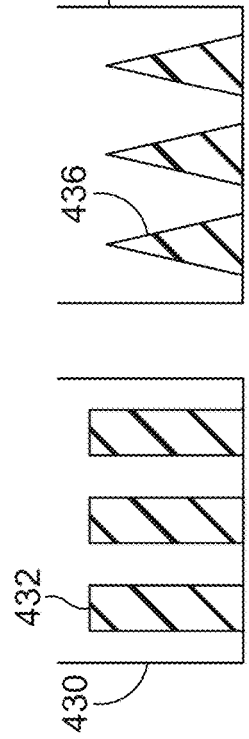
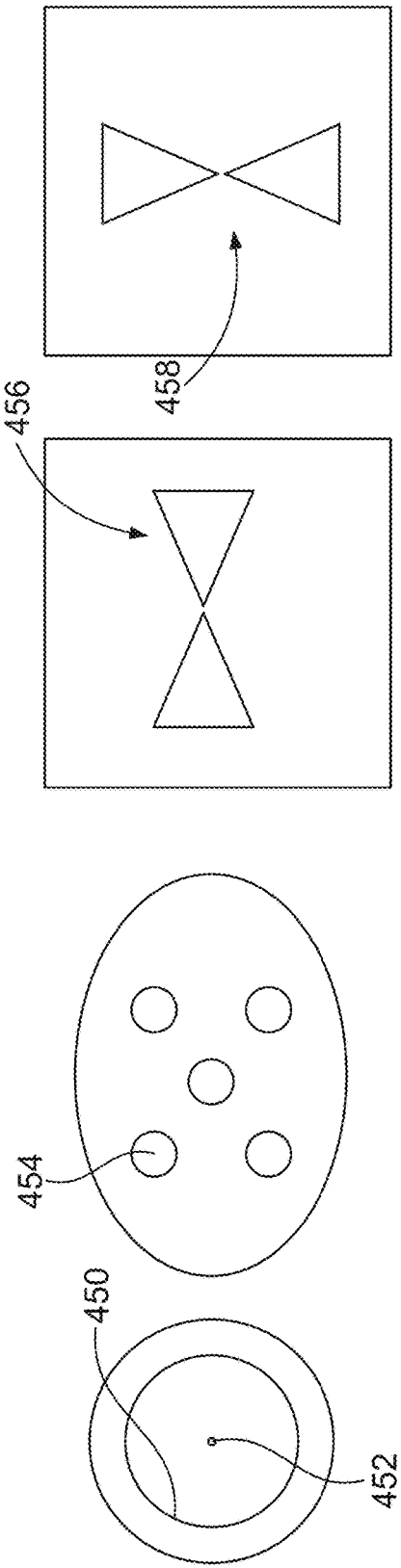

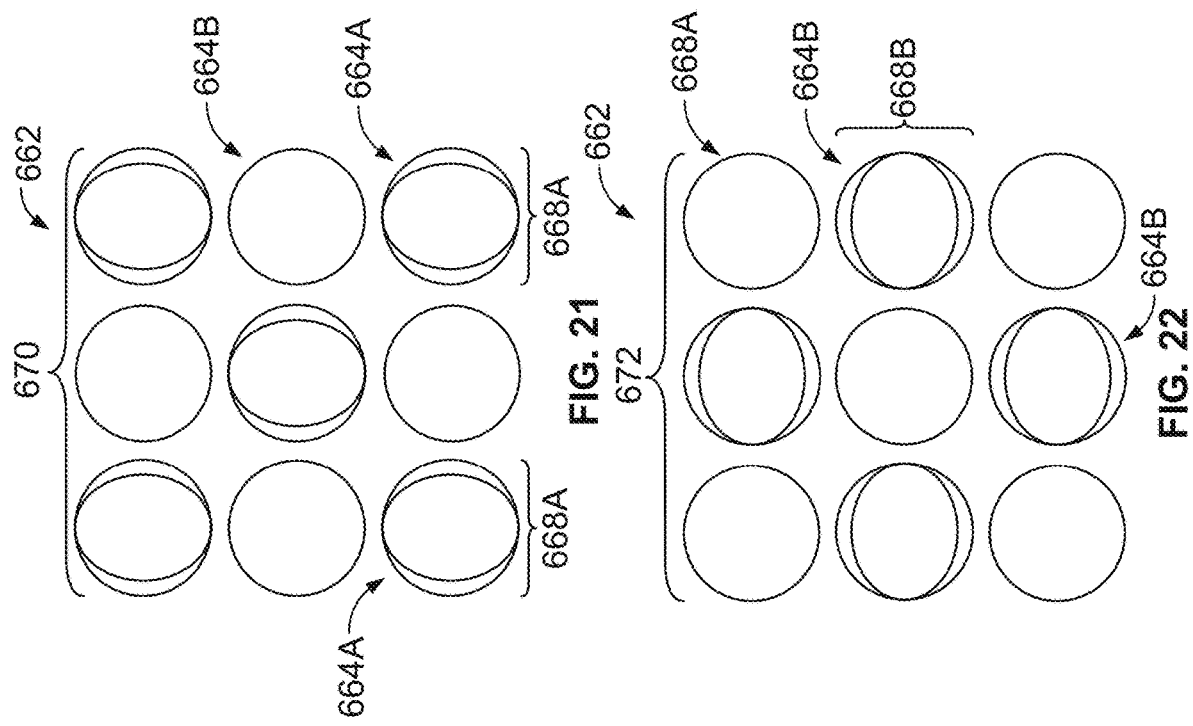
FIG. 21
FIG. 22
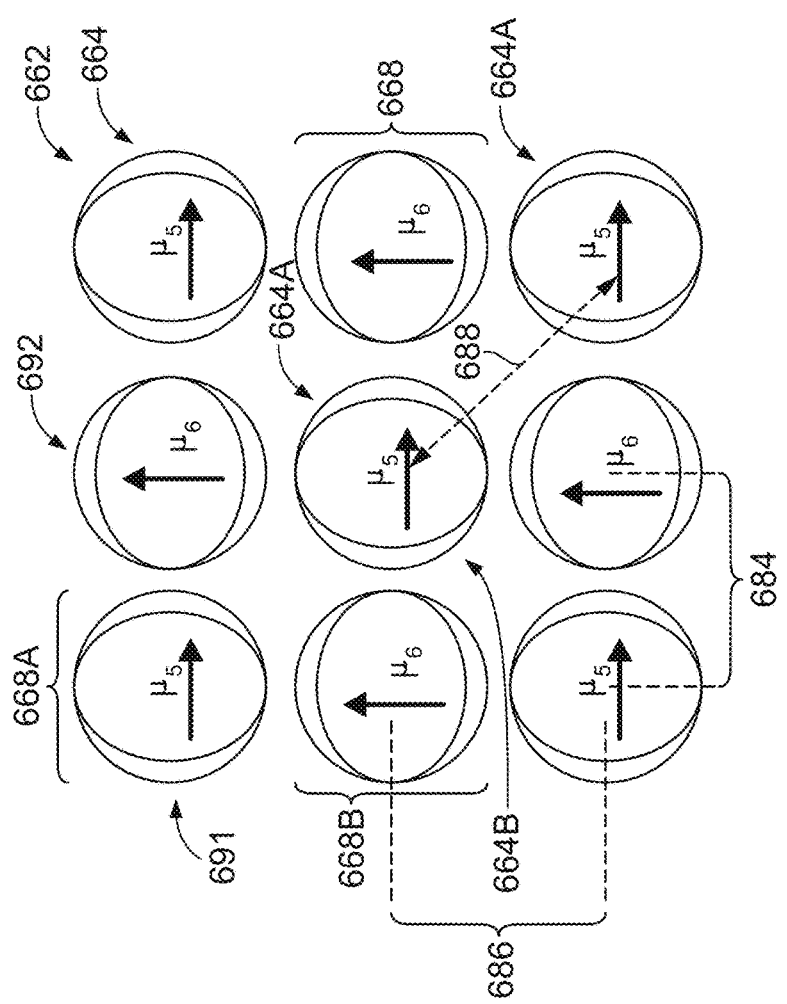
FIG. 20

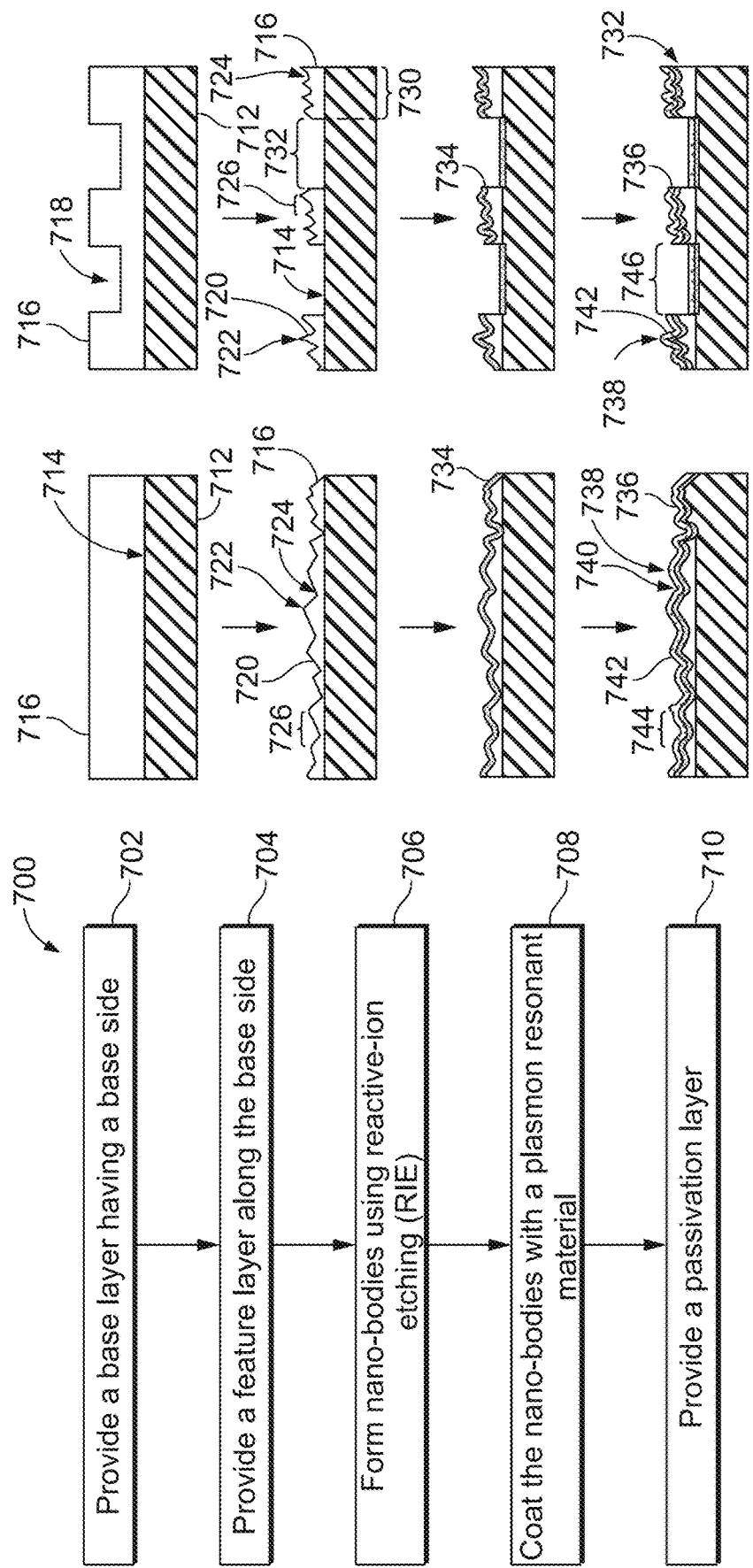

STRUCTURED SUBSTRATES FOR IMPROVING DETECTION OF LIGHT EMISSIONS AND METHODS RELATING TO THE SAME

CROSS-REFERENCE TO RELATED APPLICATIONS

The present application is a continuation of U.S. patent application Ser. No. 15/564,174, filed on Oct. 3, 2017, which is a national stage entry of International Patent Application No. PCT/US2016/027399, filed on Apr. 14, 2016, which claims the benefit of U.S. Provisional Application No. 62/147,440, filed on Apr. 14, 2015, all of which are incorporated herein by reference in their entirety.

BACKGROUND

The present disclosure relates generally to biological or chemical analysis and more particularly to systems and methods for detecting light emissions from an array of reaction sites.

Various protocols in biological or chemical research involve performing a large number of controlled reactions at localized areas of a support surface or within reaction cavities. The designated reactions may then be observed or detected and subsequent analysis may help identify or reveal properties of chemicals involved in the reaction. For example, in some multiplex assays, an unknown analyte having an identifiable label (e.g., fluorescent label) may be exposed to thousands of known probes under controlled conditions. Each known probe may be deposited into a corresponding well of a microplate. Observing any chemical reactions that occur between the known probes and the unknown analyte within the wells may help identify or reveal properties of the analyte.

Other protocols that detect light emissions from an array of reaction sites include known DNA sequencing protocols, such as sequencing-by-synthesis (SBS) or cyclic-array sequencing. In SBS, a plurality of fluorescently-labeled nucleotides are used to sequence nucleic acids of numerous clusters (or clonal populations) of amplified DNA that are located on the surface of a substrate. The surface may, for example, define a channel in a flow cell. The sequences of the nucleic acids in the different clusters are determined by running numerous cycles in which a fluorescently-labeled nucleotide is added to the cluster and then excited by a light source to provide light emissions.

Although the sequencing systems currently used are effective in identifying the nucleotides and determining a sequence of the nucleic acids, systems that are more cost-effective and/or that achieve an even smaller error rate are desired. For example, it is desirable to increase the density of reaction sites. Sequencing methodologies and corresponding systems, however, exploit a complex collection of technologies. Improvements in some of these technologies have been shown to provide substantial cost reductions. However, it is difficult to predict which, if any, is amenable to cost-reducing improvements. Given the dependencies between the technologies in the sequencing systems it is even more difficult to predict which can be modified without having an adverse impact on the overall performance of the methodology or system.

One challenge confronted by many protocols is detecting, with a suitable level of confidence, the designated reactions that generate light emissions. This challenge is even more difficult as the reaction sites become smaller and the density of reaction sites becomes greater. For example, reaction sites may have a diameter or width that is 750 nm or less, and adjacent reaction sites may be separated by 750 nm or less. One consequence of the reaction sites becoming smaller is that the amount of generated light emissions also becomes smaller and, consequently, more challenging to detect. Moreover, as the density of reaction sites becomes greater, it may be more difficult to distinguish which reaction sites provided the light emissions. In addition to the above, it is generally desirable to decrease the amount of time used for detecting the light emissions (also referred to as scan time or image time). As scan times decrease, fewer photons are detected, thereby rendering it even more challenging to reliably detect light emissions that are indicative of a designated reaction occurring.

Accordingly, a need exists for apparatuses, systems, and methods that generate a sufficient amount of light for detecting designated reactions within an array of reaction sites.

BRIEF SUMMARY

Presented herein are structures substrates and methods for manufacturing structures substrates that improve the detectability of optical emissions provided by discrete reaction sites. For example, the structures substrates may increase an intensity of an excitation light experienced by biological substances at the discrete sites, may increase an intensity of the optical emissions from the biological substances, and/or may control a directionality of the optical emissions. Also presented herein are methods of detecting optical emissions from an array of discrete sites. The discrete sites may be reaction cavities formed within a substrate body or localized areas along a surface of a device substrate. The optical emissions may be generated by, for example, fluorescence, chemiluminescence, bioluminescence, electroluminescence, radioluminescence, and the like. Also presented herein are structured substrates having a greater density of discrete sites (or smaller pitch between adjacent sites) than known systems and methods of manufacturing the same.

In some embodiments, the methods and structured substrates may be configured to enhance the light emissions of fluorescently-labeled samples and, more specifically, fluorescently-labeled nucleic acids. In particular embodiments, the methods and compositions presented herein provide fluorescent enhancement of DNA clusters in sequencing by synthesis reactions involving dye-labeled nucleotides. However, it should be understood that methods and devices described herein may also be suitable for other applications.

In an embodiment, a structured substrate is provided. The structured substrate includes a substrate body having an active side. The substrate body includes reaction cavities that open along the active side and interstitial regions that separate the reaction cavities. The structured substrate includes an ensemble amplifier positioned within each of the reaction cavities. The ensemble amplifier includes a plurality of nanostructures configured to at least one of amplify electromagnetic energy that propagates into the corresponding reaction cavity or amplify electromagnetic energy that is generated within the corresponding reaction cavity.

In an embodiment, a method of manufacturing a structured substrate is provided. The method includes providing a base layer having a base side and forming nanostructures along the base side of the base layer. The method also includes forming a cavity layer that is stacked above the base side. The cavity layer includes a plurality of reaction cavities in which each reaction cavity includes a plurality of the nanostructures therein. The plurality of nanostructures form an ensemble amplifier of the corresponding reaction cavity that is configured to at least one of amplify electromagnetic energy propagating into the corresponding reaction cavity or amplify electromagnetic energy generated within the corresponding reaction cavity In an embodiment, a method of manufacturing a structured substrate is provided. The method includes providing a base layer having a base side and forming nanostructures along the base side of the base layer. The method also includes providing a nanoimprint lithography (NIL) layer over the array of nanostructures. The method also includes imprinting an array of reaction cavities into the NIL layer, wherein a different sub-array of the nanostructures is positioned under each reaction cavity. Each sub-array of nanostructures is surrounded by a respective fill region of the NIL layer. The method also includes removing the respective fill regions of the NIL layer to expose the sub-arrays of nanostructures within the corresponding reactions cavities. The sub-array of nanostructures within each reaction cavity forming an ensemble amplifier of the corresponding reaction cavity that is configured to at least one of amplify electromagnetic energy propagating into the corresponding reaction cavity or amplify electromagnetic energy generated within the corresponding reaction cavity.

In an embodiment, a method of manufacturing a structured substrate is provided. The method includes providing a base layer having a base side and providing a nanoimprint lithography (NIL) layer along the base side. The method also includes imprinting the NIL layer to form a base portion and an array of nanobodies that project from the base portion. The method also includes depositing a plasmon resonant film that covers the nanobodies to form a plurality of nanostructures. Each nanostructure includes a corresponding nanobody and a portion of the plasmon resonant film. The method also includes forming a cavity layer including a plurality of reaction cavities in which each reaction cavity includes a plurality of the nanostructures therein. The plurality of nanostructures form an ensemble amplifier of the corresponding reaction cavity that is configured to at least one of amplify electromagnetic energy propagating into the corresponding reaction cavity or amplify electromagnetic energy generated within the corresponding reaction cavity.

In an embodiment, a method of manufacturing a structured substrate is provided. The method includes providing a working substrate having a side surface and an array of reaction cavities. Each of the reaction cavities has an opening along the side surface and extending a depth from the corresponding opening into the working substrate. The reaction cavities coincide with an array plane. The method also includes directing a deposition stream onto the working substrate at a non-orthogonal angle with respect to the array plane. The deposition stream includes a plasmon resonant material. The working substrate forms a shadow area and an incident area in each reaction cavity relative to a path of the deposition stream such that the plasmon resonant material of the deposition stream is blocked by the side surface from being deposited onto the shadow area and is permitted to pass through the opening and form along the incident area.

In an embodiment, a method of manufacturing a structured substrate is provided. The method includes (a) providing a working substrate having a side surface and an array of reaction cavities. Each of the reaction cavities has an opening along the side surface and extending a depth from the corresponding opening into the working substrate, the reaction cavities coinciding with an array plane. The method also includes (b) positioning the working substrate in a receiving orientation relative to a material source. The method also includes (c) directing a deposition stream from the material source onto the working substrate at a non-orthogonal angle with respect to the array plane. The deposition stream includes a plasmon resonant material. The working substrate forms a shadow area and an incident area in each reaction cavity when in the receiving orientation such that the plasmon resonant material from the deposition stream is blocked by the side surface from being deposited onto the shadow area and is permitted to pass through the opening and form along the incident area.

Accordingly, one embodiment presented herein is a substrate, comprising: a plurality of nanostructures distributed on a solid support; a gel material forming a layer in association with the plurality of nanostructures; and a library of target nucleic acids in the gel material. In certain embodiments, the nanostructures are formed of a plasmon resonant material. In certain embodiments, the plasmon resonant material comprises a material selected from the group consisting of: Gold (Au), Silver (Ag), Tin (Sn) Rhodium (Rh), Ruthenium (Ru), Palladium (Pd), Osmium (Os), Iridium (Ir), Platinum (Pt), Titanium (Ti) and Aluminum (Al), Chromium (Cr), Copper (Cu), p-type doped silicon, n-type doped silicon, and gallium arsenide. The plasmon resonant material may comprise a metallic alloy. For example, the plasmon resonant material may comprise Zinc-Indium-Tin Oxide (ZITO) or Tantalum Oxide (e.g., $TaO_5$). In certain embodiments, gel material covers the nanostructures. In certain embodiments, the solid support comprises a surface of a flow cell. In certain embodiments, the solid support comprises a planar surface having a plurality of wells, the nanostructures being distributed within the plurality of wells.

Also presented herein is a method of making a substrate, comprising: (a) providing a solid support comprising a planar surface; (b) dispersing a plurality of nanostructures on the surface of the solid support; (c) and coating at least a portion of the solid support with a gel material thereby forming a gel layer covering the plurality of nanostructures. In certain embodiments, the nanostructures are formed of a plasmon resonant material. In certain embodiments of this method, steps (b) and (c) are performed simultaneously. In certain embodiments, step (b) is performed prior to step (c). In certain embodiments, the method can further comprise (d) delivering a library of target nucleic acids to the gel material to produce an array of nucleic acid features in the gel material. In some embodiments, each feature comprises a different nucleic acid species. In certain embodiments, the plasmon resonant material comprises a material selected from the group consisting of: Gold (Au), Silver (Ag), Tin (Sn) Rhodium (Rh), Ruthenium (Ru), Palladium (Pd), Osmium (Os), Iridium (Ir), Platinum (Pt), Titanium (Ti) and Aluminum (Al), Chromium (Cr), Copper (Cu), p-type doped silicon, n-type doped silicon, and gallium arsenide. The plasmon resonant material may comprise a metallic alloy. For example, the plasmon resonant material may comprise Zinc-Indium-Tin Oxide (ZITO) or Tantalum Oxide (e.g., $TaO_5$).

Also presented herein is a method of detecting nucleic acids, comprising: providing a solid support comprising a plurality of nanostructures; a gel material forming a layer covering the plurality of nanostructures; and a library of target nucleic acids in the gel material; contacting the solid support with at least one fluorescently labeled probe that binds to the target nucleic acids; and detecting fluorescent signal on the solid support to distinguish the target nucleic acids that bind to the at least one probe. In certain embodiments, the nanostructures are formed of a plasmon resonant material. In certain embodiments, the plasmon resonant material comprises a material selected from the group consisting of: Gold (Au), Silver (Ag), Tin (Sn) Rhodium (Rh), Ruthenium (Ru), Palladium (Pd), Osmium (Os), Iridium (Ir), Platinum (Pt), Titanium (Ti) and Aluminum (Al), Chromium (Cr), Copper (Cu), p-type doped silicon, n-type doped silicon, and gallium arsenide. The plasmon resonant material may comprise a metallic alloy. For example, the plasmon resonant material may comprise Zinc-Indium-Tin Oxide (ZITO) or Tantalum Oxide (e.g., $TaO_5$). In certain embodiments, the solid support comprises a surface of a flow cell. In certain embodiments, the solid support comprises planar surface having a plurality of wells, the nanostructures distributed among the plurality of wells. In certain embodiments, the fluorescently labeled probe comprises a fluorescently labeled nucleotide. In certain embodiments, the fluorescently labeled probe comprises a fluorescently labeled oligonucleotide. In certain embodiments, detecting comprises detection of hybridization of an oligonucleotide probe to target nucleic acids in each feature. In certain embodiments, detecting comprises detection of incorporation of a nucleotide or an oligonucleotide probe to target nucleic acids in each feature.

Also presented herein is an array, comprising: a solid support comprising a surface, the surface comprising a plurality of wells, the wells being separated from each other by interstitial regions; and a plurality of nanostructures in each of said plurality of wells. In certain embodiments, the nanostructures are plasmonic nanostructures. In certain embodiments, the nanostructures are situated at the bottom of the wells. In certain embodiments, the nanostructures are situated along the walls of the wells. In certain embodiments, the interstitial regions are substantially devoid of nanostructures. In certain embodiments, the nanostructures comprise nanostructures. In certain embodiments, the nanostructures have a diameter of greater than 1 nm, 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm or greater than 100 nm. In certain embodiments, the nanostructures have a diameter of less than 100 nm, 90 nm, 80 nm, 70 nm, 60 nm, 50 nm, 40 nm, 30 nm, 20 nm, 10 nm, 9 nm, 8 nm, 7 nm, 6 nm, 5 nm, 4 nm, 3 nm, 2 nm, or less than 1 nm. In certain embodiments, the nanostructures comprise dimers or trimers within the wells. In certain embodiments, the nanostructures comprise bowtie nanoantennae. In certain embodiments, the nanostructures comprise nanorods. In certain embodiments, the nanostructures comprise nanorings. In certain embodiments, the nanostructures comprise nanoplugs. In certain embodiments, the nanostructures comprise nanogratings. In certain embodiments, the wells further comprise a gel material. In certain embodiments, the gel material comprises a hydrogel. In certain embodiments, the solid support comprises a surface of a flow cell.

Also presented herein is a method of making an array, comprising obtaining a solid support comprising a planar surface, the surface comprising a plurality of wells, the wells being separated from each other by interstitial regions; coating a metal film on the solid support; subjecting the metal film to a thermal annealing process, thereby forming a plurality of nanostructures in each of said plurality of wells. In certain embodiments, the nanostructures are formed of a plasmon resonant material. In certain embodiments, the method further comprises polishing the planar surface to substantially remove nanostructures from the interstitial regions and to maintain the nanostructures in the wells. In certain embodiments, the method further comprises coating at least a portion of the solid support with a gel material, thereby depositing the gel material in a plurality of the wells. In certain embodiments, nanostructures comprise a material selected from the group consisting of: Gold (Au), Silver (Ag), Tin (Sn) Rhodium (Rh), Ruthenium (Ru), Palladium (Pd), Osmium (Os), Iridium (Ir), Platinum (Pt), Titanium (Ti) and Aluminum (Al), Chromium (Cr), Copper (Cu), p-type doped silicon, n-type doped silicon, and gallium arsenide. The plasmon resonant material may comprise a metallic alloy. For example, the plasmon resonant material may comprise Zinc-Indium-Tin Oxide (ZITO) or Tantalum Oxide (e.g., $TaO_5$).

Also presented herein is a method of detecting nucleic acids, comprising: providing a solid support comprising a planar surface, the surface comprising a plurality of wells, the wells being separated from each other by interstitial regions; plurality of nanostructures in each of said plurality of wells; a gel material forming a layer covering the plurality of nanostructures; and a library of target nucleic acids in the gel material; contacting the solid support with at least one fluorescently labeled probe that binds to the target nucleic acids; and detecting fluorescent signal on the solid support to distinguish the target nucleic acids that bind to the at least one probe. In certain embodiments, the nanostructures are formed of a plasmon resonant material. In certain embodiments, nanostructures comprise a material selected from the group consisting of: Gold (Au), Silver (Ag), Tin (Sn) Rhodium (Rh), Ruthenium (Ru), Palladium (Pd), Osmium (Os), Iridium (Ir), Platinum (Pt), Titanium (Ti) and Aluminum (Al), Chromium (Cr), Copper (Cu), p-type doped silicon, n-type doped silicon, and gallium arsenide. In certain embodiments, the nanostructures are situated at the bottom of the wells. In certain embodiments, the nanostructures are situated along the walls of the wells. In certain embodiments, the interstitial regions are substantially devoid of nanostructures. In certain embodiments, the wells further comprise a gel material. In certain embodiments, the gel material comprises a hydrogel. In certain embodiments, the solid support comprises a surface of a flow cell. In certain embodiments, the fluorescently labeled probe comprises a fluorescently labeled nucleotide. In certain embodiments, the fluorescently labeled probe comprises a fluorescently labeled oligonucleotide. In certain embodiments, detecting comprises detection of hybridization of an oligonucleotide probe to target nucleic acids in each feature. In certain embodiments, detecting comprises detection of incorporation of a nucleotide or an oligonucleotide probe to target nucleic acids in each feature.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 2 is a flow chart illustrating a method of manufacturing a structured substrate in accordance with an embodiment.

FIG. 3 is a flow chart illustrating a method of manufacturing a structured substrate in accordance with an embodiment that includes nano-imprint lithography (NIL) material.

FIG. 8A illustrates a perspective view of a nanostructure that may be used with one or more embodiments.

FIG. 8B illustrates a perspective view of a nanostructure that may be used with one or more embodiments.

FIG. 8C illustrates a perspective view of a nanostructure that may be used with one or more embodiments.

FIG. 8D illustrates a perspective view of a nanostructure that may be used with one or more embodiments.

FIG. 8E illustrates a perspective view of a nanostructure that may be used with one or more embodiments.

FIG. 9A illustrates a cross-section of a nanostructure that may be used with one or more embodiments.

FIG. 9B illustrates a cross-section of a nanostructure that may be used with one or more embodiments.

FIG. 9C illustrates a cross-section of a nanostructure that may be used with one or more embodiments.

FIG. 9D illustrates a cross-section of a nanostructure that may be used with one or more embodiments.

FIG. 10A illustrates a plan view of a nanostructure that may be used with one or more embodiments.

FIG. 10B illustrates a plan view of a nanostructure that may be used with one or more embodiments.

FIG. 10C illustrates a plan view of a nanostructure that may be used with one or more embodiments.

FIG. 10D illustrates a plan view of a nanostructure that may be used with one or more embodiments.

FIG. 20 is a plan view of a structured substrate having an array of reaction sites.

FIG. 21 is the plan view of the structured substrate during a first detection step.

FIG. 22 is the plan view of the structured substrate during a second detection step.

FIG. 23 is a flow chart illustrating a method of manufacturing a structured substrate in accordance with an embodiment.

FIG. 24 is a side view illustrating different steps of the method shown in FIG. 23.

FIG. 25 is a side view illustrating different steps of the method shown in FIG. 23 in which the structured substrate includes separate reaction sites.

DETAILED DESCRIPTION

Figure 1:
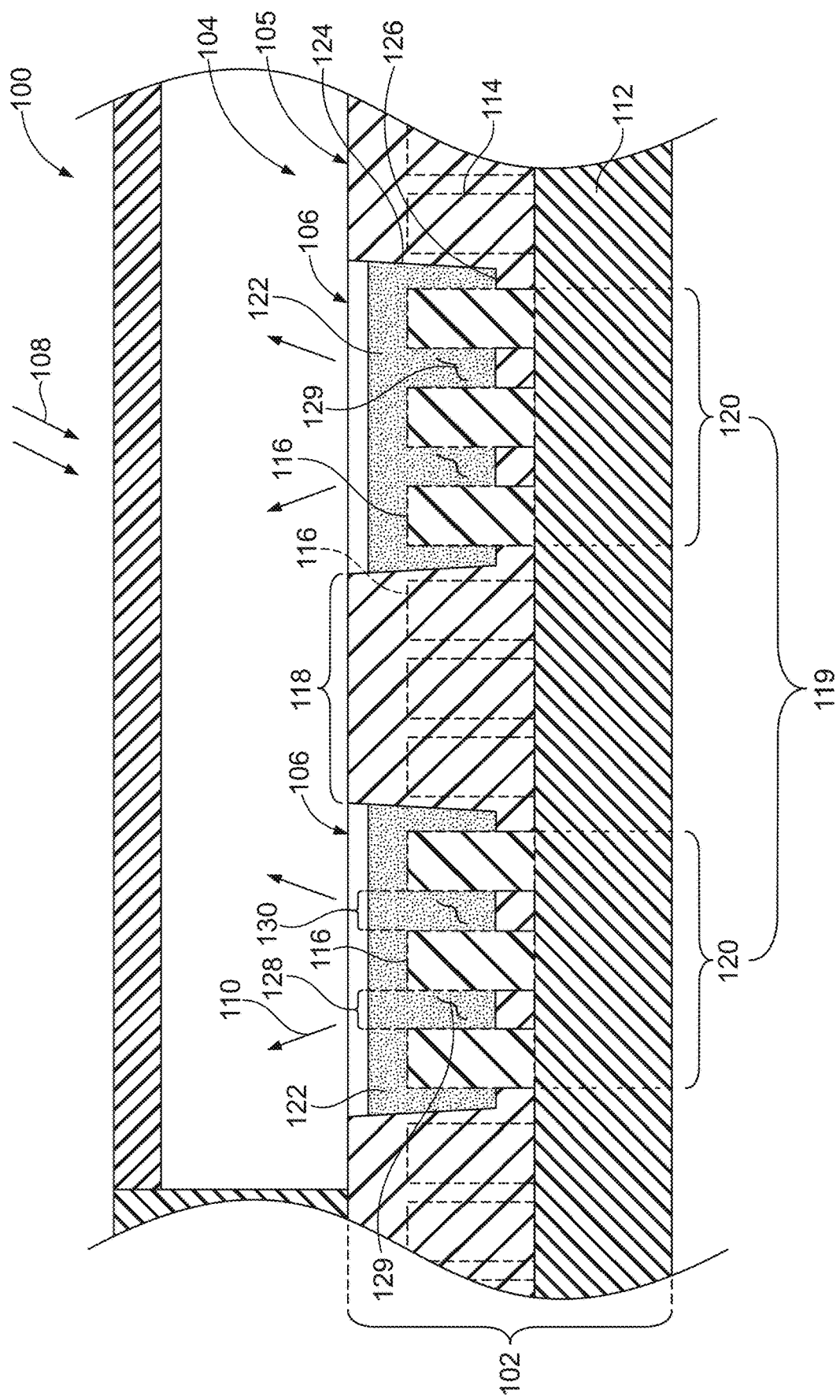
FIG. 1 illustrates a cross-section of a portion of a structured substrate formed in accordance with an embodiment.

The present application includes subject matter similar to subject matter described in U.S. Provisional Application No. 61/920,244, filed on Dec. 23, 2013, and entitled ENHANCING DNA CLUSTER FLUORSCENCE USING LOCALIZED SURFACE PLASMON RESONANCE, and in International Application No. PCT/US2014/072256, filed on Dec. 23, 2014 and entitled STRUCTURED SUBSTRATES FOR IMPROVING DETECTION OF LIGHT EMISSIONS AND METHODS RELATING TO THE SAME, each of which is incorporated herein by reference in its entirety.

The subject matter of the present application may also be applicable with or include similar subject matter that is described in U.S. Patent Appl. Publ. Nos. 2014/0242334; 2014/0079923; and 2011/0059865 and U.S. Pat. No. 8,895, 249. Each of these publications and the patent is incorporated herein by reference in its entirety.

One or more embodiments set forth herein are configured to directly or indirectly enhance light emissions from an array of reaction sites so that the light emissions may be detected by, for example, an imaging system or device. To this end, embodiments may at least one of increase an intensity of an excitation light experienced by a biological substance, increase an intensity of the light emissions generated by the biological substance, and/or control a directionality of the light emissions so that the light emissions may be detected. The increase in intensity and/or control of the directionality of the light emissions may be caused, in part, by one or more nanostructures located at the corresponding reaction site. The amount of increase may be measured relative to an amount of electromagnetic energy that exists at the reaction site without the nanostructure(s).

The array of reaction sites may be disposed along a structured substrate. The structured substrate may be, for example, a flow cell having a channel for directing reagents alongside the reaction sites. The light emissions may be detected by an imaging system that may include, for example, an objective lens that scans or sweeps alongside the structured substrate to detect the light emissions from the reaction sites. Exemplary systems capable of detecting light emissions from the structured substrates set forth herein are described in U.S. Appl. Publ. Nos. 2012/0270305 A1 and 2013/0261028 A1, each of which is incorporated herein by reference in its entirety. Alternatively, the structured substrate may be integrated with an imaging device, such as a solid-state imaging device (e.g., CMOS). In such embodiments, the imaging device may have one or more light sensors that are aligned with reaction sites to capture light emissions from the reaction sites. Such embodiments are described in U.S. Provisional Application No. 61/914,275 and International Application No. PCT/US14/69373, each of which is incorporated herein by reference in its entirety.

A technical effect provided by at least one of the embodiments may include an increased signal intensity from the emitters of the biological substance. The increase in signal intensity may reduce an error rate by increasing the likelihood that the signals will be detected. Another technical effect may include a decrease in signal to noise ratio that enables faster scan speeds and reduces overall time for conducting a protocol. For instance, with respect to sequencing-by-synthesis technology, faster scan speeds on sequencing instruments are desired, but faster scan speeds result in fewer photons being collected per cluster on the imaging camera. With fewer photons captured, the signal to noise ratio typically decreases and it becomes more difficult to confidently assign a base. Furthermore on some sequencing instruments, low NA optics result in signals that are inherently larger and dimmer, potentially yielding higher error rates. Embodiments set forth herein may increase the number of photons that are captured. Another technical effect for at least some embodiments includes a method of manufacturing a structured substrate that is more reliable than at least some known methods and more cost-effective than at least some known methods.

As used herein, a "biological substance" or "chemical substance" includes biomolecules, samples-of-interest, analytes-of-interest, and other chemical compound(s). A biological substance or chemical substance may be used to detect, identify, or analyze other chemical compound(s), or function as intermediaries to study or analyze other chemical compound(s). In particular embodiments, the biological substance is a nucleic acid or, more specifically, a colony of nucleic acids having a common sequence. In particular embodiments, the biological or chemical substances include a biomolecule. As used herein, a "biomolecule" includes at least one of a biopolymer, nucleoside, nucleic acid, polynucleotide, oligonucleotide, protein, enzyme, polypeptide, antibody, antigen, ligand, receptor, polysaccharide, carbohydrate, polyphosphate, cell, tissue, organism, or fragment thereof or any other biologically active chemical compound(s) such as analogs or mimetics of the aforementioned species.

As another example, a biological or chemical substance may include an enzyme or reagent used in a coupled reaction to detect the product of another reaction such as an enzyme or reagent used to detect pyrophosphate in a pyrosequencing reaction. Enzymes and reagents useful for pyrophosphate detection are described, for example, in U.S. Patent Publication No. 2005/0244870 A1, which is incorporated herein in its entirety.

Biological or chemical substances may be naturally occurring or synthetic and located within a designated area or space. In some embodiments, the biological or chemical substances may be bound to a solid phase or gel material. Biomolecules, samples, and biological or chemical substances may also include a pharmaceutical composition. In some cases, biomolecules, samples, and biological or chemical substances of interest may be referred to as targets, probes, or analytes.

Embodiments may be particularly suitable for enhancing emissions from fluorescently-labeled nucleic acids. By way of example, embodiments may provide fluorescent enhancement of DNA clusters in sequencing by synthesis reactions involving dye-labeled nucleotides. Embodiments may increase a signal intensity from fluorescent labels during sequencing by synthesis. The increase in signal intensity may improve overall sequencing performance by reducing sequencing error arising from low intensity clusters and cluster dropouts during long sequencing runs.

Various embodiments utilize one or more nanostructures to amplify electromagnetic energy at a reaction site. For embodiments that utilize a plurality of nanostructures (e.g., two or more nanostructures), the plurality of nanostructures may be referred to as an ensemble amplifier. As used herein, the terms "nanostructure" and "nanoparticle" are used interchangeably to refer to a structure having a greatest dimension (e.g, height, width, diameter) in the range of about 1 nm to about 1000 nm, including any integer or non-integer value between 1 nm and 1000 nm. In typical embodiments, the nanoparticle is a metallic particle or a silicon particle. In some embodiments, the nanoparticle core is a spherical or nearly spherical particle of 20-200 nm in diameter. In some embodiments the range is about 1 nm to about 50 nm (for example about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nm).

Anisotropic nanostructures (e.g., non-spherical structures) may have a length and a width or, for some embodiments, a diameter. In some embodiments, the length of the anisotropic nanostructure is the greatest dimension of the nanostructure. In some embodiments, the length of an anisotropic nanoparticle is a dimension parallel to the plane of the aperture in which the nanoparticle was produced. In some embodiments, the length of an anisotropic nanoparticle is the dimension perpendicular to the plane of the aperture in which the nanoparticle was produced. In the case of anisotropic nanostructures, the nanostructure may have a width or diameter in the range of about 50 nm to about 750 nm. In other embodiments, the nanostructure has a width or diameter of about 350 nm or less. In other embodiments, the nanoparticle has a width or diameter of 250 nm or less and in some embodiments, a width or diameter of 100 nm or less. In some embodiments, the width or diameter is between 15 nm to 300 nm.

In some embodiments, the nanoparticle has a length of about 10-750 nm. In some embodiments, the nanostructures have a preselected shape and can be, for example a nanotube, a nanowire, nanosphere, or any shape comprising the above-described dimensions (e.g., triangular, square, rectangular, or polygonal shape in 2 dimensions, or cuboid, pyramidal, cylindrical, spherical, discoid, or hemispheric shapes in the 3 dimensions). Some examples of nanostructures include, for example, bowtie nanoantennae, nanospheres, nanopyramids, nanoshells, nanorods, nanowires, nanorings, nanoplugs, nanogratings and the like. Preformed dimers and trimers of nanostructures can also be loaded into wells and have the advantage of precisely controlling nanoparticle spacing.

The nanostructures can either be fabricated on a surface or pre-formed and then loaded into the reaction cavities, such as nanowells. Examples of such structures include plasmonic nanoplugs fabricated at the bottom of nanowells, bowtie and cavity antennas in nanowells, metal nanogratings on which nanowells could be formed, nanostructures reflowed in nanowells or a combination of some or all of the above. One example would be a metal nanoplug in a nanowell with nanostructures on the walls formed through an electron beam evaporation process. Ensemble amplifiers or constructs (dimers, n-mers) may also be positioned within the reaction cavities. Such methods allow for precise sub-nanometer control over nanostructure spacings and can be formed on a large scale using bottom up self-assembly.

The spacing between any two nanostructures on a surface can be any distance. In some embodiments, the spacing can be a multiple of a wavelength of incident light energy, such as a particular emission or excitation wavelength in fluorescence spectroscopy. The spacing can be, for example, 1λ, 2λ, 3λ, 4λ, or another multiple of a chosen wavelength (λ) of incident light energy. Thus, using as an example an emission wavelength (λ) of 532 nm, the spacing between nanostructures can be about 532 nm (1λ), about 1064 nm (2λ), or another multiple of the emission wavelength. In some embodiments, the spacing can be a fraction of a wavelength of incident light energy, such as a particular emission or excitation wavelength in fluorescence spectroscopy. The spacing can be, for example, 1λ, ½λ, ⅓λ, ¼λ or another multiple of a chosen wavelength of incident light energy. Thus, using as an example an emission wavelength of (λ) 532 nm, the spacing between nanostructures can be about 532 nm (1λ), 266 nm (½λ), 133 nm (⅓λ) or another fraction of the emission wavelength.

In some embodiments, the nanostructures may be referred to as "plasmonic nanostructure" or "nanoplasmonic structure." These terms may be used interchangeably and refer to any independent structure exhibiting plasmon resonance characteristic of the structure, including (but not limited to) both nanostructures, nanostructures and combinations or associations of nanostructures.

The term "nanoantenna," as used herein, includes a nanostructure or a plurality of nanostructures (or ensemble amplifier) that acts to amplify electromagnetic energy, such as light energy. As used herein, a nanoantenna (or ensemble amplifier) does not necessarily exhibit plasmon resonance characteristics. In some embodiments, a nanoantenna does not substantially comprise a plasmon resonant material.

Thus, in some embodiments, nanoantennas are presented which are made of a non-metal material but which exhibits amplification characteristics of electromagnetic energy. Nanostructures presented herein can be of any suitable shape and size so as to produce the desired energy amplification. Some exemplary shapes of nanoantennas include, for example, bowtie nanoantennae, nanospheres, nanopyramids, nanoshells, nanorods, nanowires, nanorings, nanoplugs, nanogratings and the like. It will be appreciated that any of a number of known methods can be suitable for fabrication and/or deposition of nanoantenna on a solid support. Methods for fabrication of nanoantenna are known in the art and include, for example, the methods described herein for nanoparticle fabrication and deposition.

The nanostructures can comprise any material suitable for use in the methods and compositions described herein, for example, any type of material exhibiting surface plasmon resonance (SPR). In certain preferred embodiments, the nanoparticle comprises a plasmon resonant material. Examples include, but are not limited to, metal nanostructures. For example, the nanostructures can comprise a metal such as one or more of Gold (Au), Silver (Ag), Tin (Sn) Rhodium (Rh), Ruthenium (Ru), Palladium (Pd), Osmium (Os), Iridium (Ir), Platinum (Pt), Titanium (Ti) and Aluminum (Al), Chromium (Cr), Copper (Cu), or any other suitable metal. The plasmon resonant material may comprise a metallic alloy. For example, the plasmon resonant material may comprise Zinc-Indium-Tin Oxide (ZITO) or Tantalum Oxide (e.g., $TaO_5$). The nanostructures can be formed from a single material such as, for example a single metal. Additionally or alternatively, the nanostructures can be formed from a combination of two or more different materials, such as, for example, two or more metals. For example, the nanostructures can comprise a metal/metal mixture such as Sn/Au or Ag/Au. Alternatively or additionally, vertical layered nanostructures, such as multilayer structures of the metal-insulator-metal type may be applied. Examples include p-type doped silicon, n-type doped silicon, and gallium arsenide. In particular embodiments, the nanostructures may be formed from a polymer that is coated by a plasmon resonant material and/or a metallic material.

Formation of nanostructures on a solid support can be performed using any one of a number of methods known in the art. Nanostructures can be formed using bottom-up self-assembly of plasmonic nanostructures and nano-antennae on the sequencing substrate. For example, any one of a number of methods for deposition of layers of a material can be used, such as those described by Gaspar et al. (Scientific Reports, 2013, 3, 1469), which is incorporated herein by reference. Layer-fabricating processes that may be used to form the nanostructures include photolithography, etching (e.g., reactive-ion etching), sputtering, evaporation, casting (e.g., spin coating), chemical vapor deposition, electrodeposition, epitaxy, thermal oxidation, physical vapor deposition, and the like. In some embodiments, the nanostructures may be formed using a shadow technique. In some embodiments, the nanostructures may be formed using nanolithography, such as nanoimprint lithography (NIL).

In exemplary embodiments described herein, the nanostructures can be pre-formed and mixed in a colloid-like composition with a gel material, which is deposited on a surface. Alternatively or additionally, nanostructures can be first deposited on a surface followed by deposition of a gel material over the nanostructures. In other embodiments, a gel material can be deposited on a surface and nanostructures are deposited over the gel material.

In some embodiments, the nanostructures are formed in a well (or concave feature) of a solid surface. A film of starting material such as Sn/Au can be deposited on a solid surface containing nanowells, followed by thermal annealing. In some embodiments, thermal annealing can be utilized to promote formation of nanostructures as the film coalesces into discrete particles. Nanoparticle size can be a function of the starting film thickness. A further polishing step following the thermal anneal can result in nanostructures only in the wells while leaving the interstitial regions substantially void of nanostructures. Nanostructures in interstitial regions can be removed through, for example, chemical and/or mechanical polishing. A distribution of nanoparticle sizes is observed in each nanowell enabling broad spectrum fluorescence enhancement.

In some embodiments, a nanostructure such as a nanoring can be formed along the wall of wells (or concave features) on a surface. The nanostructures can be fabricated using any one of a number of methodologies known in the art. For example, Au can be deposited using sputtered deposition. In an embodiment, conformal deposition of a ~65 nm Au layer may be followed by a reactive ion etch (ME) process. The remaining Au layer was located along the walls of the nanowells, forming nanorings in each of the nanowells.

The terms "excitation light" and "light emissions" mean electromagnetic energy and are used to differentiate the source of the electromagnetic energy. Excitation light is generally provided from a light source (e.g., laser) that is positioned a distance away from the reaction site. For example, for embodiments that include reaction cavities, the light source may be positioned outside of the reaction cavities. Light emissions, however, are typically generated by an emitter within or at the reaction sites. The emitter may be, for example, a fluorophore. Particular embodiments may be configured to amplify electromagnetic energy at any wavelength between 300 nm to 750 nm (e.g., 300 nm, 301 nm, 302 nm, 303 nm, 304 nm, 305 nm, 306 nm, 307 nm, 308 nm . . . 745 nm, 746 nm, 747 nm, 748 nm, 749 nm, and 750 nm). As used herein, the term "wavelength" shall not be limited to a single wavelength unless expressly stated to constitute "a single wavelength" or "only one wavelength". Instead, the term "wavelength" shall encompass a narrow range of wavelengths located about a desired or target wavelength (e.g., 532 nm±10 nm, 532 nm±5 nm, 660 nm±10 nm, 660 nm±5 nm), unless explicitly recited otherwise.

The nanostructures of each ensemble amplifier may be configured relative to one another to amplify the electromagnetic energy in a designated manner. For example, a distance that separates the nanostructures of a corresponding ensemble amplifier may be based on the electromagnetic energy that is desired to be amplified. The nanostructures of the ensemble amplifier may be configured for a particular wavelength (e.g., narrow band of wavelengths). For example, one or more embodiments may be configured to amplify electromagnetic energy having a wavelength of 532 nm. One or more embodiments may be configured to amplify electromagnetic energy having a wavelength of 660 nm. In some embodiments, the ensemble amplifiers may be capable of amplifying multiple wavelengths or broader ranges of wavelengths.

One or more embodiments may include ensemble amplifiers that preferentially respond to certain polarizations of light. For example, a first ensemble amplifier may be configured to respond to a first polarization light, and a second ensemble amplifier may be configured to respond to a second polarization light. The preferential response may be based on, for example, a dipole moment of the corresponding ensemble amplifier.

By way of example, when a first ensemble amplifier is illuminated by a first polarization light, the light emissions provided by the first ensemble amplifier may provide a maximum signal intensity for the first ensemble amplifier. However, when a second ensemble amplifier (which has a different configuration than the first ensemble amplifier) is illuminated by the first polarization light, the light emissions provided by the second ensemble amplifier may be, for example, about 40% or less the maximum signal intensity for the second ensemble amplifier. Likewise, when the second ensemble amplifier is illuminated by the second polarization light, the light emissions provided by the second ensemble amplifier may provide a maximum signal intensity for the second ensemble amplifier. However, when the first ensemble amplifier is illuminated by the second polarization light, the light emissions provided by the first ensemble amplifier may be, for example, about 40% or less the maximum signal intensity for the first ensemble amplifier.

In many cases, the first and second ensemble amplifiers may be illuminated simultaneously, concurrently, or during the same imaging sequence such that a single image detects light emissions from the first ensemble amplifiers and the second ensemble amplifiers. In such embodiments, the ensemble amplifiers that preferentially respond to the excitation light may provide a greater signal intensity than the ensemble amplifiers that do not preferentially respond to the excitation light. A subsequent may then be captured that uses a different excitation light.

FIG. 1 is a cross-section of a portion of a structured substrate 100 formed in accordance with an embodiment. The structured substrate 100 includes a substrate body 102 having an active side 104. The active side 104 includes a plurality of reaction sites 106 and a side surface 105 that extends between the reaction sites 106. The reaction sites 106 are spaced apart from each other by interstitial regions 118 of the substrate body 102. The interstitial regions 118 are areas along the active side 104 or portions of the substrate body 102 that separate the reaction sites 106 from one another. The side surface 105 extends along the interstitial regions 118. In some embodiments, the plurality of reaction sites 106 form a dense array of reaction sites 106 such that the interstitial regions 118 are separated, for example, by less than 1000 nm. In particular embodiments, a center-to-center spacing 119 between adjacent reaction sites 106 may be less than 1000 nm. In particular embodiments, the center-to-center spacing 119 may be less than 800 nm, less than 700 nm or, more particularly, less than 500 nm.

In the illustrated embodiment, the interstitial regions 118 include a continuous, planar side surface 105, but the interstitial regions 118 may include non-planar surfaces in other embodiments. The interstitial regions 118 may include a surface material that differs from the material of the reaction sites 106 and may functionally isolate the reaction sites 106 from one another. In the illustrated embodiment, only two reaction sites 106 are shown along the active side 104. It should be understood, however, that the reaction sites 106 may be part of an array of reaction sites that may include hundreds, thousands, or millions of reaction sites.

In the illustrated embodiment, the reaction sites 106 are cavities and, as such, will hereinafter be referred to as reaction cavities 106. The reaction cavities 106 are typically concave features that form a depression or indentation along the active side 104. The reaction cavities 106 may be, for example, wells, pits, channels, recesses, and the like. However, it should be understood that other embodiments may include reaction sites that are not located within cavities. For example, the reaction sites may be distributed along a planar surface. Such embodiments are described in U.S. Provisional Application No. 61/920,244, which is incorporated herein by reference in its entirety. For example, embodiments that are configured to have ensemble amplifiers that respond differently to different polarized lights may have reaction areas along a planar surface.

As shown in FIG. 1, a reaction cavity has a cross section that is taken perpendicular to the active side 104. The cross-section may include curved sections, linear sections, angles, corners. Generally, a reaction cavity need not pass completely through one or more layers. For example, each of the reaction cavities 106 has at least one sidewall 124 that extends between the active side 104 and a bottom surface 126 of the reaction cavity 106. Both the sidewall 124 and the bottom surface 126 are defined by the cavity layer 114. In alternative embodiments, the base layer 112 (or other layer) may define the bottom 126 of the reaction cavity 106.

The reaction cavities 106 open to the active side 104 such that the reaction cavities 106 are accessible along the active side 104. For example, the reaction cavities 106 may be capable of receiving gel material and/or fluid along the active side 104 during manufacture of the structured substrate 100 or when the structured substrate 100 is used during analysis. The active side 104 may also receive an excitation light 108 from a light source (not shown) and/or face an optical component (not shown), such as an objective lens, that detects light emissions 110 from the reaction cavities.

The substrate body 102 may be formed from one or more stacked layers. In the illustrated embodiment, the substrate body 102 includes a base layer 112 and a cavity layer 114. The base layer 112 may be, for example, a glass ($SiO_2$) wafer. The cavity layer 114 may be a polymer. The substrate body 102, however, may include other layers in alternative embodiments.

As used herein, the term "layer" is not limited to a single continuous body of material unless otherwise noted. For example, each layer may be formed form multiple sub-layers of the same or different materials. Moreover, each layer may include one or more features of different materials located therein or extending therethrough. The different layers may be formed using known layer-fabricating processes, such as photolithography, etching, sputtering, evaporation, casting (e.g., spin coating), chemical vapor deposition, electrodeposition, epitaxy, thermal oxidation, physical vapor deposition, and the like. One or more layers may also be formed using nanolithography, such as nanoimprint lithography (NIL). As used herein, the term "working substrate" includes one or more stacked layers in which at least one of the layers is being processed to form a structured substrate from the working substrate.

Each of the reaction cavities 106 may include at least one nanostructure 116. The interstitial regions 118 may be substantially devoid of nanostructures. In other embodiments, however, the nanostructures 116 are distributed such that one or more of the nanostructures 116 are located within the interstitial regions 118 (as indicated by phantom lines). For example, the nanostructures 116 may be distributed evenly or uniformly along the base layer 112 such that, after the cavity layer 114 is formed, the nanostructures 116 are also located or embedded within the interstitial regions 118. In some embodiments, the embedded nanostructures 116 within the interstitial regions 118 do not have a substantial effect on the electromagnetic energy that propagates into the reaction cavities or the electromagnetic energy that is generated within the reaction cavities. In other embodiments, the embedded nanostructures 116 may have an effect on the electromagnetic energy that propagates into the reaction cavities or the electromagnetic energy that is generated within the reaction cavities.

Figure 44:
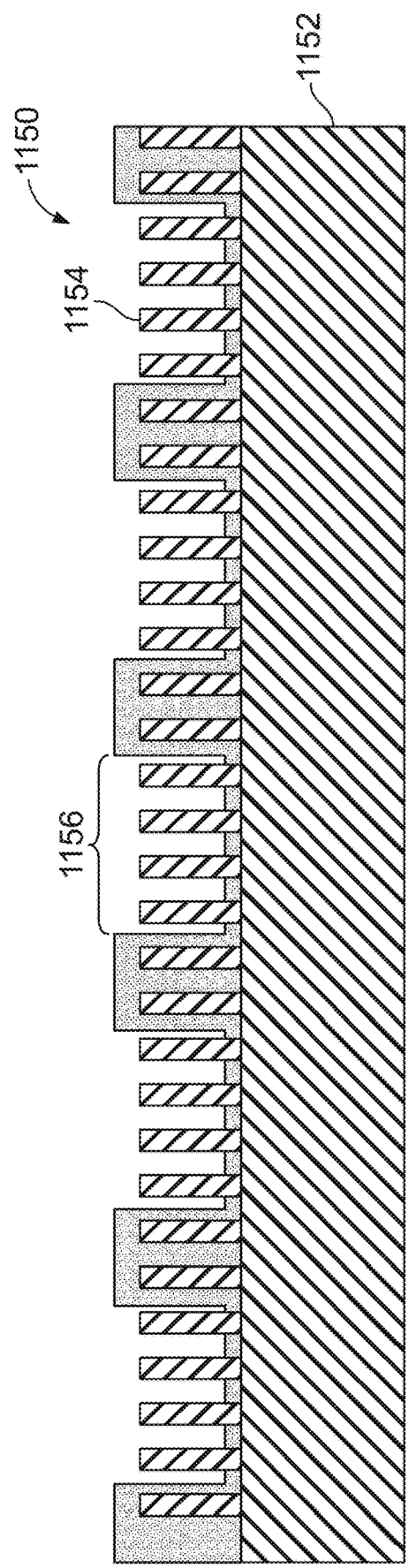
FIG. 44 is a side view of a structured substrate having a uniform embedded array of nanoparticles in accordance with an embodiment.

FIG. 44 illustrates such an example in which a structured substrate 1150 includes an array of nanostructures 1154 that are evenly distributed along a base layer 1152. A cavity layer forms a plurality of cavities 1156 in which the nanostructures 1154 form an ensemble amplifier in each cavity 1156. Such embodiments may reduce the complexity in manufacturing the structured substrates by not requiring precise alignment of the reaction cavities with the nanostructures.

In the illustrated embodiment of FIG. 1, each of the reaction cavities 106 includes a plurality of nanostructures 116. However, it should be understood that alternative embodiments may include only a single nanostructure. The plurality of nanostructures may form an ensemble amplifier, which is hereinafter referred to as an ensemble amplifier 120. The ensemble amplifier 120 is positioned within each of the reaction cavities 106 and is configured to at least one of amplify electromagnetic energy that propagates into the corresponding reaction cavity or amplify electromagnetic energy that is generated within the corresponding reaction cavity.

As used herein, an "ensemble of nanostructures" or "ensemble amplifier" includes a plurality of nanostructures that are configured to at least one of amplify electromagnetic energy that is incident on the discrete site (e.g., reaction cavity) or amplify electromagnetic energy that is generated at the discrete site. For instance, the electromagnetic energy may be the excitation light 108 that propagates from an exterior environment and into a reaction cavity 106, wherein the excitation light is absorbed by an emitter (e.g., fluorophore) that is associated with a biological substance. As another example, the electromagnetic energy may be light emissions 110 that are emitted from the biological substances. More specifically, after being excited, the fluorophores may emit the electromagnetic energy (e.g., light emissions 110) that is then amplified by the ensemble 120 of nanostructures. In some embodiments, the ensemble amplifier 120 may also be referred to as a nanoantenna, because the nanostructures collectively operate to amplify and transmit the light emissions 110 away from the reaction sites.

An ensemble amplifier may include two or more nanostructures that operate in concert to amplify the electromagnetic energy. As described herein, in some embodiments, an ensemble amplifier may be configured to preferentially amplify a type of electromagnetic energy or, more specifically, electromagnetic energy having a predetermined wavelength. For example, an ensemble amplifier may have a greater amplification effect on light emissions than on excitation light or vice versa. Nonetheless, in some embodiments, an ensemble amplifier may amplify both the light emissions and the excitation light.

As used herein, when an ensemble amplifier is "configured to amplify electromagnetic energy," each of the nanostructures may have one or more qualities such that the ensemble amplifier collectively operate to amplify the electromagnetic energy. The qualities may include, for example, a material composition of the nanostructure, a shape of the nanostructure, a size of the nanostructure, and a position of the nanostructure relative to other nanostructures in the ensemble. For example, adjacent nanostructures 116 may have a distance 128 therebetween that is configured amplify electromagnetic energy that is confined therebetween. In some embodiments, the resulting amplification in light emissions may be due to a combination of localized surface plasmon resonance and resonant energy transfer processes.

Also shown in FIG. 1, the reaction cavities 106 may include an organic material 122 disposed within the reaction cavities 106. The organic material 122 may cover the nanostructures 116. In some embodiments, the organic material 122 is configured to immobilize a biomolecule within the corresponding reaction cavity. For example, the biomolecule may be a nucleic acid. Although not shown in FIG. 1, a passivation layer may be applied between the organic material 122 and the cavity layer 114 and/or the nanostructures 116.

In particular embodiments, the organic material 122 includes a gel material, such as a hydrogel. As used herein, the term "gel material" is intended to mean a semi-rigid material that is permeable to liquids and gases. Typically, gel material can swell when liquid is absorbed or received by the gel material and can contract when liquid is removed from the gel material (e.g., through drying). Exemplary gel materials include, but are not limited to those having a colloidal structure, such as agarose; polymer mesh structure, such as gelatin; or cross-linked polymer structure, such as polyacrylamide, SFA (see, for example, US Pat. App. Pub. No. 2011/0059865 A1, which is incorporated herein by reference) or PAZAM (see, for example, U.S. Prov. Pat. App. Ser. No. 61/753,833, which is incorporated herein by reference). Particularly useful gel material will conform to the shape of a reaction cavity where it resides. Some useful gel materials can both (a) conform to the shape of the reaction cavity where it resides and (b) have a volume that does not substantially exceed the volume of the reaction cavity where it resides.

In particular embodiments, the organic material 122 has a volume that is configured to accommodate only a single analyte such that steric exclusion prevents more than one analyte from being captured or seeding the reaction cavity. Steric exclusion can be particularly useful for large analytes, such as nucleic acids. More specifically, reaction cavities can expose a surface of the organic material (e.g., gel material) having an area that is equivalent to or smaller than a diameter of the excluded volume of target nucleic acids that are to be seeded on the substrate. The excluded volume for a target nucleic acid and its diameter can be determined, for example, from the length of the target nucleic acid. Methods for determining the excluded volume of nucleic acids and the diameter of the excluded volume are described, for example, in U.S. Pat. No. 7,785,790; Rybenkov et al., *Proc. Natl. Acad. Sci. U.S.A.* 90: 5307-5311 (1993); Zimmerman et al., *J. Mol. Biol.* 222:599-620 (1991); or Sobel et al., *Biopolymers* 31:1559-1564 (1991), each of which is incorporated herein by reference. Conditions for steric exclusion are set forth in U.S. Ser. No. 13/661,524 and U.S. Pat. No. 7,785,790, each of which is incorporated herein by reference, and can be readily used for structured substrates of the present disclosure.

In some embodiments, such as embodiments that utilize steric exclusion, a library of target nucleic acids can be delivered to reaction cavities that contain the gel material prior to initiation of an amplification process. For example, target nucleic acids can be delivered to a structured substrate under conditions to seed the gel material in the substrate with the target nucleic acids. The structured substrate can optionally be washed to remove target nucleic acids that do not seed the gel material as well as any other materials that are unwanted for subsequent processing or use of the structured substrate.

Nonetheless, it will be understood that in other embodiments, the area of the exposed gel material may be substantially greater than the diameter of the excluded volume of the target nucleic acids that are transported to the amplification sites. Thus, the area for the features can be sufficiently large that steric exclusion does not occur.

Returning to FIG. 1, in some embodiments, the nanostructures 116 are formed along the base layer 112 such that the nanostructures 116 project from the base layer 112 and into the reaction cavities 106. In some embodiments, the nanostructures 116 extend through a portion of the cavity layer 114. In other embodiments, the bottom surface 126 may be defined by a portion of the base layer 122 such that the nanostructures 116 do not extend through the cavity layer 114.

During a protocol in which light emissions are detected by a detector, the light emissions may be generated in response to the excitation light 108. In alternative embodiments, the excitation light 108 is not provided and, instead, the excitation light 108 is generated by emitters coupled to the biomolecule 129. In some embodiments, a gain field 130 exists along one of the nanostructures 116 or between two or more nanostructures 116. The gain field 130 may represent a space where a high intensity electric field is created by the nanostructures 116 in response to excitation light and/or light emissions. For some applications, the nanostructures 116 amplify the excitation light 108 such that the emitters are more energized by the excitation light and provide a greater signal intensity for detection. In other applications, the nanostructures 116 do not amplify the excitation light 108, but amplify the light emissions 110 such that the light emissions 110 provide a greater signal intensity for detection. In some applications, however, the nanostructures 116 may be capable of amplifying both the excitation light 108 and the light emissions 110 such that a greater intensity of the excitation light 108 is experienced by the emitters and a greater intensity of the light emissions 110 is provided by the emitters. Accordingly, embodiments set forth herein may provide a greater signal intensity that is easier to detect by imaging systems or devices. For example, embodiments set forth herein may provide a greater signal intensity compared to sites that do not include such nanostructures.

The present application describes various methods for manufacturing or fabricating structured substrates that may be used to detect or analyze designated reactions. At least some of the methods are illustrated in the figures as a plurality of steps. However, it should be understood that embodiments are not limited to the steps illustrated in the figures. Steps may be omitted, steps may be modified, and/or other steps may be added. By way of example, although some embodiments described herein may include only two layers, other embodiments may include three, four, or more layers. Moreover, steps described herein may be combined, steps may be performed simultaneously, steps may be performed concurrently, steps may be split into multiple sub-steps, steps may be performed in a different order, or steps (or a series of steps) may be re-performed in an iterative fashion. In addition, although different methods are set forth herein, it should be understood that the different methods (or steps of the different methods) may be combined in other embodiments.

The structured substrates may be formed using one or more processes that may, for example, be used to manufacture integrated circuits, during microfabrication, and/or to manufacture nanotechnology. Lithography (e.g., photolithography) is one category of techniques or processes that may be used to fabricate the structured substrates described herein. In particular embodiments, one or more layers are formed using nanoimprint lithography (NIL). Exemplary lithographic techniques or processes are described in greater detail in Marc J. Madou, *Fundamentals of Microfabrication and Nanotechnology: Manufacturing Techniques for Microfabrication and Nanotechnology*, Vol. II, $3^{rd}$ Edition, Part I (pp. 2-145), which is incorporated herein by reference in its entirety.

One or more processes for fabricating structured substrates may also include subtractive techniques in which material is removed from a working substrate. Such processes include chemical techniques, such as dry chemical etching, physical/chemical etching, vapor phase etching, chemical machining (CM), anisotropic wet chemical etching, wet photoetching; electrochemical techniques, such as electrochemical etching (ECM), electrochemical grinding (ECG), reactive-ion etching (RIE), photoelectrochemical etching; thermal techniques, such as laser machining, electron beam machining, electrical discharge machining (EDM); and mechanical techniques, such as physical dry etching, sputter etching, ion milling, water-jet machining (WJM), abrasive water-jet machining (AWJM), abrasive jet machining (AJM), abrasive grinding, electrolytic in-process dressing (ELID) grinding, ultrasonic drilling, focused ion beam (FIB) milling, and the like. The above list is not intended to be limiting and other subtractive techniques or processes may be used. Exemplary subtractive techniques or processes are described in greater detail in Marc J. Madou, *Fundamentals of Microfabrication and Nanotechnology: Manufacturing Techniques for Microfabrication and Nanotechnology*, Vol. II, $3^{rd}$ Edition, Part II (pp. 148-384), which is incorporated herein by reference in its entirety.

One or more processes for fabricating structured substrates may also include additive techniques in which material is added to a working substrate. Such processes include physical vapor deposition (PVD), evaporation (e.g., thermal evaporation), sputtering, ion plating, ion cluster beam deposition, pulsed laser deposition, laser ablation deposition, molecular beam epitaxy, chemical vapor deposition (CVD) (e.g., atmospheric pressure CVD (APCVD), low pressure CVD (LPCVD), very low pressure CVD (VLPCVD), ultra-high vacuum CVD (UHVCVD), metalorganic CVD (MOCVD), laser-assisted chemical vapor deposition (LCVD), plasma-enhanced CVD (PECVD), atomic layer deposition (ALD)), epitaxy (e.g., liquid-phase epitaxy, solid-phase epitaxy), anodization, thermal spray deposition, electroplating, implantation, diffusion, incorporation in the melt, thermal oxidation, laser sputter deposition, reaction injection molding (RIM), self-assembled monolayers (SAMs), sol-gel addition, spin coating, polymer spraying, polymer dry film lamination, casting, plasma polymerization, silk screening, ink jet printing, mechanical microspotting, microcontact printing, stereolithography or microphotoforming, electrochemical forming processes, electrodeposition, spray pyrolysis, laser beam deposition, electron beam deposition, plasma spray deposition, micromolding, LIGA (which is a German acronym for x-ray lithography, electrodeposition, and molding), compression molding, and the like. The above list is not intended to be limiting and other additive techniques or processes may be used. Exemplary additive techniques or processes are described in greater detail in Marc J. Madou, *Fundamentals of Microfabrication and Nanotechnology: Manufacturing Techniques for Microfabrication and Nanotechnology*, Vol. II, $3^{rd}$ Edition, Part III (pp. 384-642), which is incorporated herein by reference in its entirety. As used herein, the term "exemplary," when used as an adjective, means serving as an example. The term does not indicate that the object to which it modifies is preferred.

FIG. 2 is a flowchart illustrating a method 200 of manufacturing a structured substrate. The method 200 includes providing, at 202, a base layer (or working substrate) having a base side. The base layer may be only a single layer of material or include one or more sub-layers. The base side may have a planar surface that is configured to have another layer deposited directly thereon. However, it is contemplated that the base side may include non-planar features prior to being combined with other layers. In particular embodiments, the base layer includes a glass ($SiO_2$) wafer, but other materials may be used.

The method 200 may also include forming, at 204, an array of nanostructures along the base side of the base layer. The forming, at 204, may include multiple processing steps. For example, the forming, at 204, may include providing (e.g., through deposition, growing, or another additive technique) a feature layer along the base side of the base layer. The forming, at 204, may include shaping (e.g., through etching or another subtractive technique) a sub-layer of the base layer to form the nanostructures. The sub-layer may also be referred to as a feature layer as the nanostructures may be formed from the sub-layer. The feature layer may include a material that is capable of being shaped into individual features that may at least partially form a basis of the nanostructures. The material may include a pure material (e.g., gold) or an alloy of material. The feature layer may also include multiple sub-layers of material (e.g., gold and chrome) that are stacked alongside each other. Optionally, one or more of the materials is a plasmon resonant material.

In particular embodiments, the forming, at 204, includes etching the feature layer to form nanobodies. The nanobodies may be arranged in sub-arrays or sets in which each sub-array (or set) may become an ensemble amplifier. In other embodiments, the nanobodies are distributed evenly or uniformly throughout the base layer, such as shown in FIG. 44. In such embodiments, some of the nanobodies will be embedded while others will be disposed within the reaction cavities.

In some embodiments, the nanobodies formed from the etching process may constitute, without further modification, nanostructures that are capable amplifying electromagnetic energy. In other embodiments, however, further processing steps may be necessary to form the nanostructures. For example, the feature layer may comprise a polymer (or other material that is not a plasmon resonant material) that may be shaped to form nanobodies for constructing the nanostructures. A thin layer or film may be subsequently added to exterior surfaces of the nanobodies to form the nanostructures. Yet still in other embodiments, the nanostructures may be locally deposited at select locations. The method 500 (FIG. 11) describes such a process.

The method 200 also includes forming, at 206, a cavity layer along the base side of the base layer. The cavity layer is configured to include the reaction cavities. For embodiments that do not include reaction cavities, the cavity layer may be referred to as a site layer. As used herein, the phrase "along the base side" or "along the base layer" includes the cavity layer being in direct contact with the base layer or includes the cavity layer being separated from the base layer by one or more intervening layers. As used herein, spatially relative terms, such as "top," "above," "below," and the like, are used herein for ease of description to distinguish one element or feature from another. The spatially relative terms do not require that the structured substrate have a particular orientation with respect to gravity during use or operation. For example, the active side of the structured substrate may face in a direction that is opposite the gravitational force direction in some embodiments. Alternatively, the active side of the structured substrate may face in the same direction as the gravitational force direction in other embodiments. The uppermost surface, such as the side surface that liquid flows along during operation, may be referred to as the top surface regardless of the orientation of the structured substrate with respect to gravity.

The forming, at 206, may include providing a cavity layer that is configured to have an array of reaction cavities. The forming, at 206, may include multiple steps. In some embodiments, the cavity layer includes pre-formed reaction cavities. Each of the reaction cavities may be aligned with a corresponding sub-array or set of nanostructures (e.g., two or more nanostructures). Optionally, the cavity layer may be etched to remove portions of the cavity layer and expose the nanostructures within the corresponding reaction cavities.

In other embodiments, the reaction cavities may be shaped while the cavity layer is positioned above and coupled to the base layer. For example, NIL material may be deposited along the base side of the base layer after the nanostructures are formed and cover the nanostructures. The NIL material may be deposited using, for example, a spin coating technique or by depositing droplets along the base side. The NIL material may comprise a material that is capable of being imprinted using the NIL technique. For example, the NIL material may comprise a polymer. The NIL material may then be imprinted or stamped with a mold (also called template) having a pattern of features that form the reaction cavities in the NIL layer. In some embodiments, the mold is transparent to allow ultraviolet (UV) or visible light to propagate therethrough. In such embodiments, the NIL material may comprise a photocurable polymer that is cured by the UV or visible light while the mold is pressed into the NIL material. Accordingly, the NIL material may cure (e.g., harden) to form the reaction cavities. This process may be identical or similar to step-and-flash imprint lithography (SFIL). In other embodiments, the NIL material may be cured by application of thermal energy and/or pressure. The NIL techniques and like processes are described in Marc J. Madou, *Fundamentals of Microfabrication and Nanotechnology: Manufacturing Techniques for Microfabrication and Nanotechnology*, Vol. II, $3^{rd}$ Edition, Part I (pp. 113-116) and Lucas et al., "Nanoimprint Lithography Based Approach for the Fabrication of Large-Area, Uniformly Oriented Plasmonic Arrays" *Adv. Mater.* 2008, 20, 1129-1134, each of which is incorporated herein by reference in its entirety.

Each of the reaction cavities may be aligned with a corresponding sub-array of nanostructures. The NIL material may be preferentially etched to expose the plurality of nanostructures within the corresponding reaction cavity. Regardless of the method of manufacturing, the sub-array of nanostructures may form an ensemble amplifier of the corresponding reaction cavity. The ensemble amplifier is configured to at least one of amplify electromagnetic energy propagating into the corresponding reaction cavity or amplify electromagnetic energy generated within the corresponding reaction cavity.

Optionally, the method 200 may also include providing, at 208, an organic material within the reaction cavities. The organic material may cover the nanostructures. In some embodiments, the organic material is provided across the active side, including the interstitial regions. The organic material may then be removed by polishing the active side. After the active side is polished, each of the reaction cavities may include corresponding organic material that is separated from other organic material of other reaction cavities. In particular embodiments, the organic material is a gel material, such as those described herein (e.g., PAZAM, SFA or chemically modified variants thereof, such as the azidolyzed version of SFA (azido-SFA).

The method 200 may also include additional steps, such as preparing surfaces of the structured substrate to interact with the fluids and samples of a designated protocol. As another example, the method 200 may include mounting, at 210, a flow cover to the active side of the cavity layer. The flow cover may define a flow channel between the flow cover and the active side. Embodiments that include flow covers are described in U.S. Provisional Application No. 61/914,275 and International Application No. PCT/US14/69373, each of which is incorporated herein by reference in its entirety.

Figure 4:
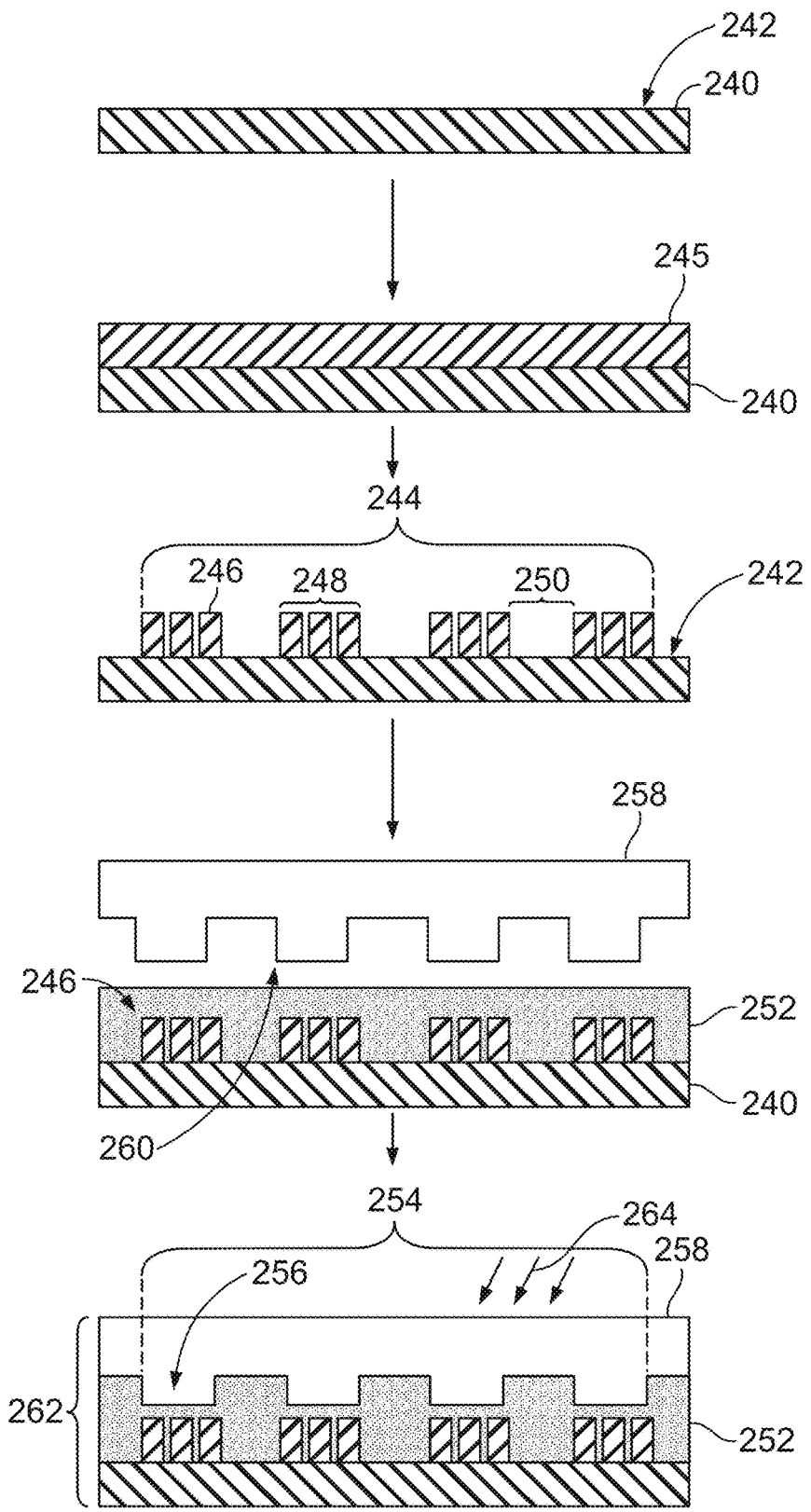
FIG. 4 illustrates different steps of the method shown in FIG. 3.
Figure 5:
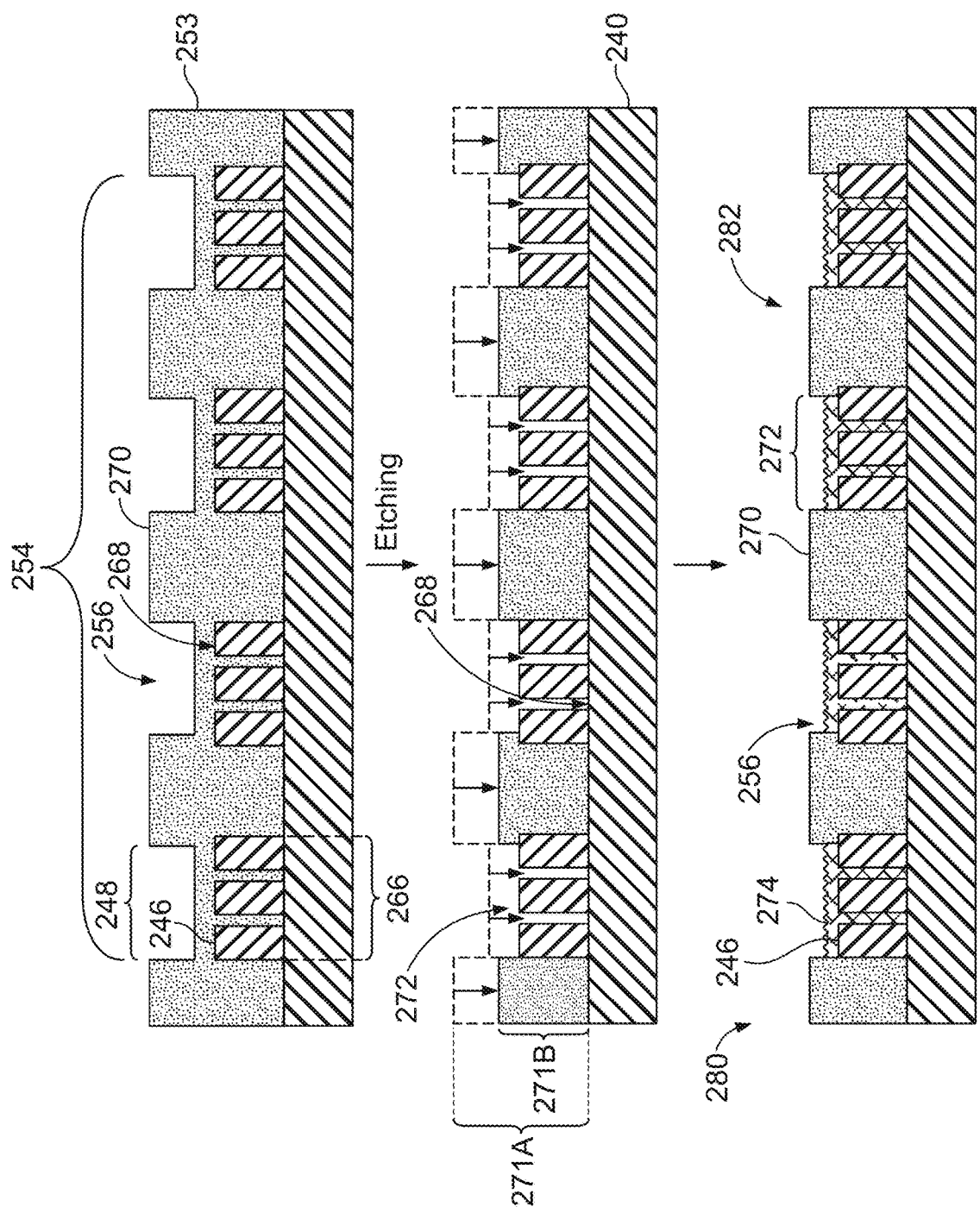
FIG. 5 illustrates different steps of the method shown in FIG. 3.

FIG. 3 illustrates a flowchart of a method 220 of manufacturing a structured substrate 280 (shown in FIG. 5). The method 220 is described with reference to FIGS. 4 and 5. The method 220 may include one or more steps that are similar or identical to the steps of method 200 (FIG. 2). The method 220 includes providing, at 222, a base layer (or working substrate) 240 having a base side 242. The method 220 also includes forming, at 224, an array 244 of nanostructures 246 along the base side 242. For example, a feature layer 245 may be provided to the base side 242 (e.g., through a deposition process) of the base layer 240. The feature layer 245 may be etched to form the array 244 of nanostructures 246. The array 244 may include sub-arrays 248 of the nanostructures 246. Also shown in FIG. 4, adjacent sub-arrays 248 are separated by a spacing 250 along the base side 242. In other embodiments, however, the feature layer 245 is etched such that the array of nanostructures 246 extends uniformly across the base layer 240 (see, e.g., FIG. 44). In such embodiments, some of the nanostructures 246 may be covered or embedded when the structured substrate is complete while other nanostructures 246 may be disposed within corresponding reaction cavities. By using a uniform array of nanostructures 246, it may not be necessary (or may be less difficult) to align the reaction cavities during manufacturing. Yet in other embodiments, the nanostructures 246 are formed across the base layer 240 in a generally random manner.

Each sub-array 248 may include a plurality of the nanostructures 246 that collectively form an ensemble amplifier when the structured substrate 280 (FIG. 5) is fully formed. For example, the nanostructures 246 of each sub-array 248 may be sized, shaped, and positioned relative to each other such that the nanostructures 246 amplify electromagnetic energy. In the illustrated embodiment, the nanostructures 246 are illustrated as upright posts that have a common shape and size. However, it should be understood that the nanostructures 246 may have different shapes in other embodiments. Furthermore, the nanostructures 246 of a single sub-array 248 are not required to have an identical shape and/or an identical size.

At 226, a NIL material 252 may be provided along the base side 242 of the base layer 240. The NIL material 252 may cover the array 244 of the nanostructures 246. The NIL material 252 may be a viscous material such that the NIL material 252 surrounds and fills empty spaces between the nanostructures 246. The NIL material 252 may comprise, for example, a polymer. In the illustrated embodiment, the NIL material 252 is provided as a NIL layer along the base side 242. In other embodiments, the NIL material may be provided as an array of droplets that, when compressed during an imprinting operation, effectively cover at least portions of the base side 242.

At 228, an array 254 of reaction cavities 256 may be imprinted into the NIL material 252. The imprinting, at 228, may include applying a mold 258 to the NIL material 252. The mold 258 may have a non-planar side 260 that includes a pattern of features. The features are sized, shaped, and positioned relative to each to shape the NIL material 252 in a predetermined manner such that the reaction cavities 256 are formed. When the mold 258 is applied to the NIL material 252, a stacked assembly 262 is formed that includes the mold 258, the NIL material 252, the nanostructures 246, and the base layer 240.

The imprinting, at 228, may also include curing the NIL material 252 to solidify the shape of the NIL material 252. For example, the curing process may include applying a UV light or visible light 264 to the stacked assembly 262. The NIL material 252 may comprise a photopolymer that is capable of solidifying after being exposed to the UV or visible light 264. However, alternative methods of solidifying or curing the NIL layer 252 may be used. For example, thermal energy (e.g., heat) or pressure may be applied to the NIL material 252 to solidify the NIL material 252 and form the reaction cavities 256.

With respect to FIG. 5, after the curing process, the NIL material becomes a solidified NIL layer 253 having the array 254 of reaction cavities 256. The solidified NIL layer 253 may constitute a cavity layer, such as the cavity layer 114 (FIG. 1), that includes the reaction cavities 256. Each reaction cavity 256 may be aligned with a corresponding sub-array 248 of the nanostructures 246 such that the reaction cavity 256 is positioned above the corresponding sub-array 248. As shown in FIG. 4, the nanostructures 246 may be positioned within a fill region 266 of the solidified NIL layer 253. The fill region 266 includes the nanostructures 246 surrounded by the solidified material of the NIL layer 253. At this stage, the fill region 266 may define a bottom surface 268 of the reaction cavity 256. Also shown, at this stage, the reaction cavities 256 may be separated by interstitial regions 270, which separate the reaction cavities 256. For embodiments in which the nanostructures 246 are uniformly spaced along the base layer 240, one or more nanostructures 246 may be located within the interstitial regions 270.

The method 220 may also include removing, at 230, the fill regions 266 to expose at least portions of the nanostructures 246 within the corresponding reaction cavities 256. For example, a preferential etching process may be applied to remove the material of the NIL layer 253 that surrounds the nanostructures 246 without substantially damaging or removing the nanostructures 246. During the removing, at 230, the bottom surface 268 of each reaction cavity 256 is lowered such that the bottom surface 268 approaches the base layer 240. In some embodiments, the NIL layer 253 within the fill regions 266 may be etched entirely such that the base layer 240 forms at least a portion of the bottom surface 268. In other embodiments, similar to the structured substrate 100 of FIG. 1, a portion of the NIL layer 253 may remain after the etching process. In such embodiments, the nanostructures 246 may extend through the NIL layer 253 (or cavity layer). During the removing, at 230, the interstitial regions 270 may also be etched, as indicated, such that a height of the interstitial regions 270 relative to the base layer 240 is reduced. The height is reduced from 271A to 271B.

As described above, the nanostructures 246 within each reaction cavity 256 may form an ensemble amplifier 272 of the corresponding reaction cavity 256. The ensemble amplifier 272 is configured to at least one of amplify electromagnetic energy propagating into the corresponding reaction cavity or amplify electromagnetic energy generated within the corresponding reaction cavity.

The structured substrate 280 is shown at the bottom of FIG. 5. The structure substrate 280 includes an active side 282 and has the reaction cavities 256 and the interstitial regions 270 that separate the reaction cavities 256. Optionally, the method 200 may include providing, at 232, an organic material 274 within the reaction cavities 256. Prior to providing the organic material 274, the working substrate may be processed for receiving the organic material 274. For example, a passivation layer (e.g., tantalum oxide or the like) and a layer of silane may be provided onto the passivation layer. Both the passivation layer and the silane layer may cover the nanostructures 246. The providing, at 232, may include spin coating the organic material onto the working substrate. However, other additive techniques may also be used. Optionally, the working substrate having the passivation layer, the silane layer, and the organic material may be incubated.

As shown in FIG. 5, the organic material 274 may cover the nanostructures 246 in the reaction cavities 256. In some embodiments, the organic material 274 is provided across the entire active side 282 such that the organic material 274 covers surfaces of the interstitial regions 270. The organic material 274 may then be removed by polishing the active side 282. After the active side 282 is polished, each of the reaction cavities 256 may include organic material 274 therein that is separated from organic material 274 in adjacent reaction cavities 256. The organic material 274 within each reaction cavity 256 surrounds the nanostructures 246 of the ensemble amplifier 272. The organic material 274 may be configured to support and/or hold a biological or chemical substance that is capable of providing light emissions, such as dye-labeled nucleic acids.

Figure 6:
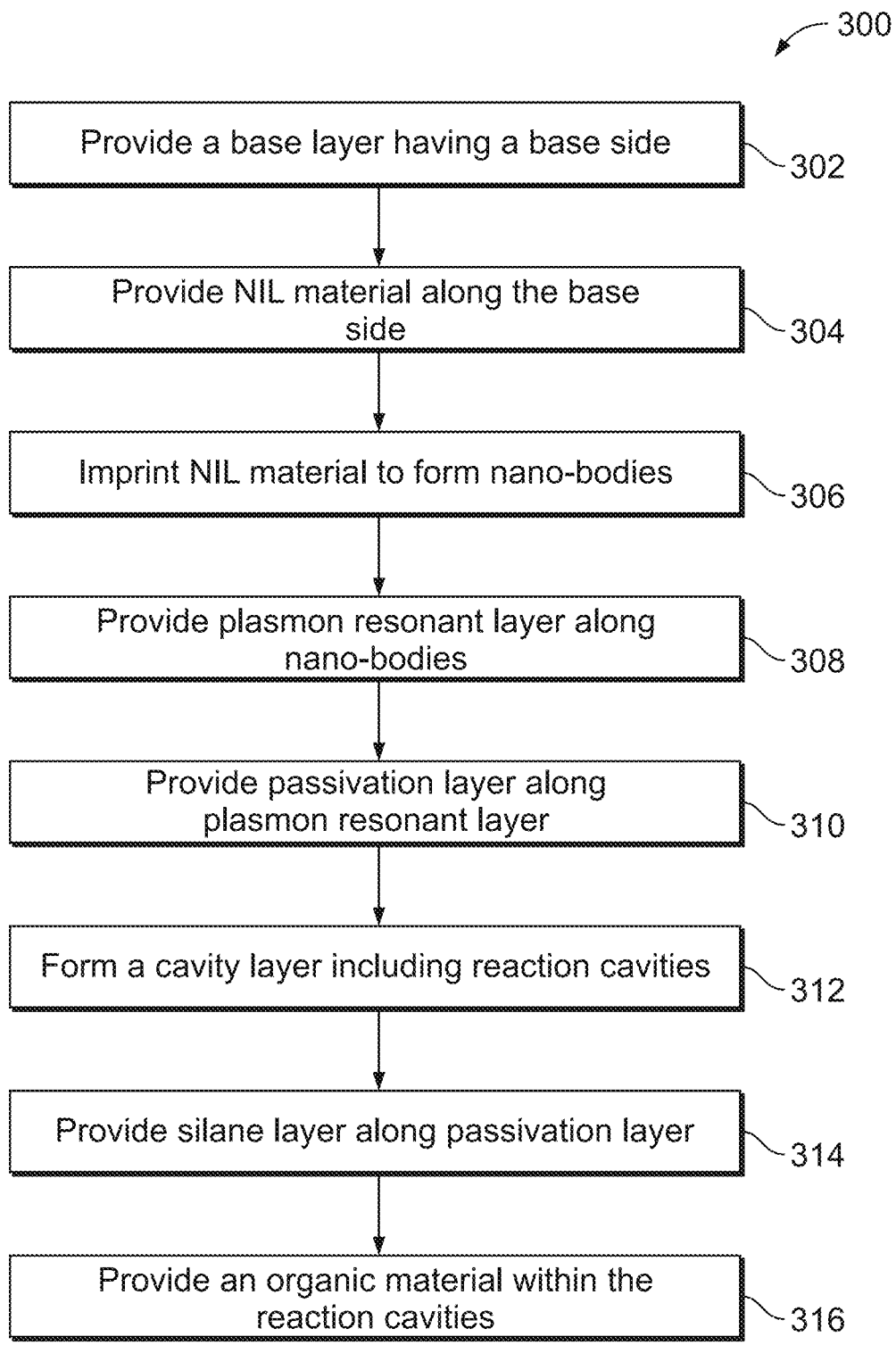
FIG. 6 is a flow chart illustrating a method of manufacturing a structured substrate in accordance with an embodiment that includes NIL material that forms nanostructures.
Figure 7:
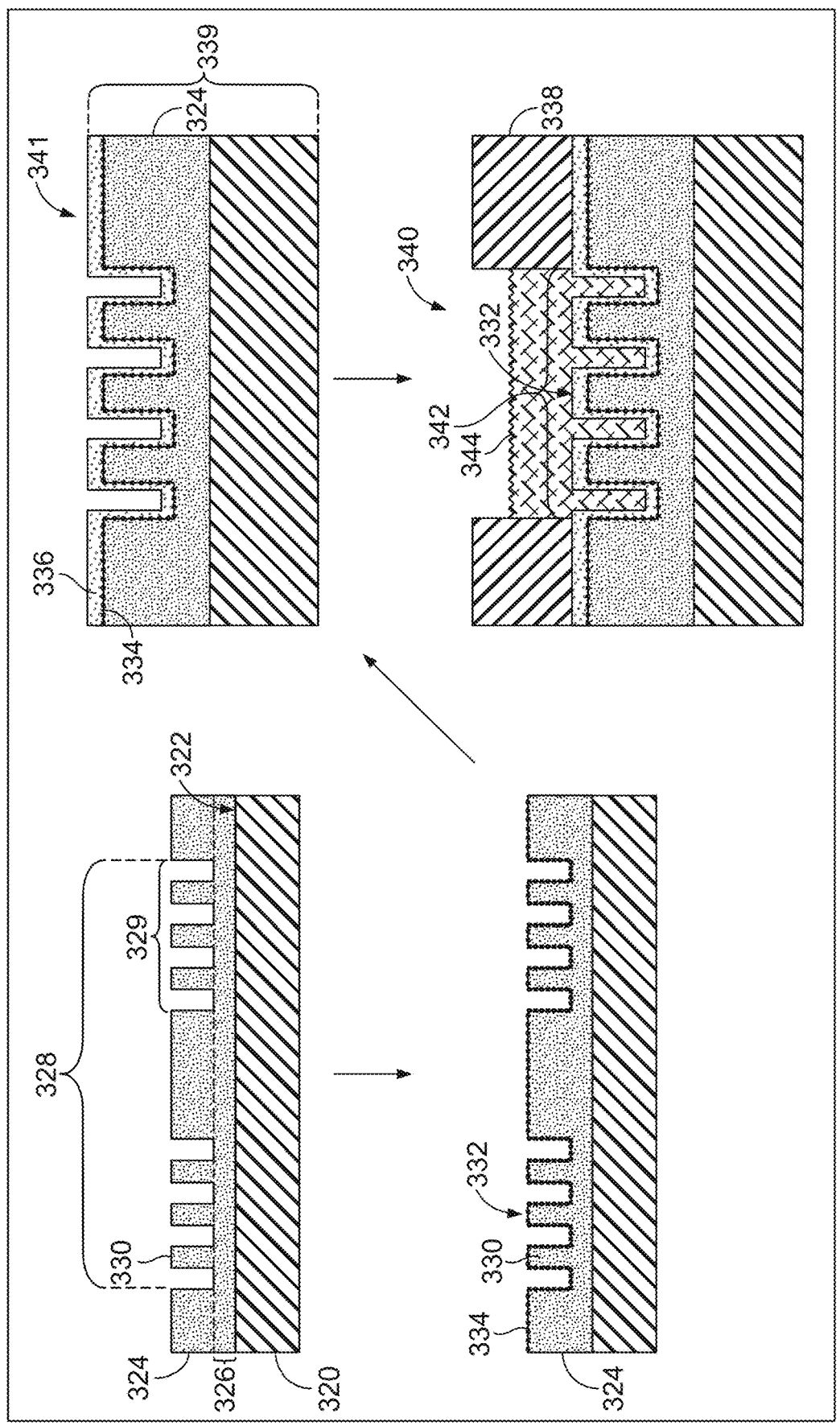
FIG. 7 illustrates different steps of the method shown in FIG. 6.

FIG. 6 is a flowchart illustrating a method 300 of manufacturing or fabricating a structured substrate. In some embodiments, the method 300 includes steps that are similar or identical to the steps of the methods 200 (FIG. 2) and 220 (FIG. 3). Different stages of the method 300 are illustrated in FIG. 7. The method 300 may include providing, at 302, a base layer (or working substrate) 320 having a base side 322 and providing, at 304, NIL material 324 along the base side 322 of the base layer 320. In some embodiments, the NIL material 324 may be provided as a NIL layer. In other embodiments, the NIL material 324 may be provided as separate droplets along the base side 322.

The method 300 may also include imprinting, at 306, the NIL material 324. After imprinting, the NIL material 324 may be a solidified NIL layer 324 having a base portion 326 (indicated by the dashed line) and an array 328 of nanobodies 330 that project from the base portion 326. In some embodiments, the nanobodies 330 are arranged to form sub-arrays, but in other embodiments the nanobodies 330 are uniformly distributed along the base layer 320, such as the nanostructures 1154 shown in FIG. 44. The base portion 326 extends between adjacent nanobodies 330. The nanobodies 330 may have a variety of shapes. In the illustrated embodiment, the nanobodies 330 are elongated posts that project away from the base portion 326 of the NIL layer 324. In alternative embodiments, the base portion 326 is not formed after imprinting. Instead, only the nanobodies 330 may be formed after imprinting.

The method 300 may also include providing, at 308, a plasmon resonant layer 334 along the NIL material 324 and, in particular, the nanobodies 330. The providing, at 308, may also be referred to as depositing or growing. In some embodiments, the plasmon resonant layer 334 may be a thin film or coating. The providing, at 308, may be executed using one or more additive techniques. For example, the providing, at 308, may include at least one of PECVD, ALD, evaporation, sputtering, spin coating, or the like. The plasmon resonant layer 334 includes a plasmon resonant material (e.g., gold, silver, silicon, and the like) that covers the nanobodies 330. Accordingly, nanostructures 332 may be formed in which each nanostructure 332 includes a respective nanobody 330 and a portion of the plasmon resonant layer 334 that covers or surrounds the respective nanobody 330.

Optionally, the method 300 may include providing, at 310, a passivation layer 336. The passivation layer 336 is configured to protect the underlying layers, such as the plasmon resonant layer 334, from damage during use of the structured substrate.

At 312, the method 300 may include forming a cavity layer 338 along the operative side 341 that includes a plurality of reaction cavities 340. In some embodiments, the cavity layer 338 may be formed using, for example, a NIL technique in which a NIL material is imprinted and cured to form the reaction cavities 340. In FIG. 7, only a single reaction cavity 340 is shown, but it should be understood that an array of reaction cavities 340 may be formed.

Also optionally, the method 300 may include providing, at 314, a silane layer (not shown). The silane layer may be configured to facilitate coupling between an organic material and/or biological or chemical substances. By way of example, the providing, at 314, may be accomplished by vapor deposition. In some embodiments, the silane layer may be provided after or before other processing steps. At this stage, the base layer 320, the NIL material 324, the plasmon resonant layer 334, the passivation layer 336, and the optional silane layer may form a working substrate 339 having an operative side 341.

If the cavity layer 338 is formed using a NIL process, empty space between the nanostructures 332 may be filled with the NIL material 324. As described above with respect to the method 220, the NIL material 324 may be removed through preferential etching. After the NIL material is removed, an ensemble amplifier 342 of the nanostructures 332 may be formed within the corresponding reaction cavity 340. At 316, an organic material may be provided to the reaction cavities 340.

In the illustrated embodiment, the cavity layer 338 is formed using a NIL process. However, it should be understood that the cavity layer 338 may be formed using other additive and/or subtractive processes, such as those described above.

FIGS. 8-10 illustrate different nanostructures that may be implemented with one or more embodiments. However, the nanostructures shown in FIGS. 8-10 are exemplary only and are not intended to be limiting. Other nanostructures may be used in alternative embodiments. In FIGS. 8A-8D, the nanostructures are located within corresponding cylindrically-shaped reaction cavities. In other embodiments, the reaction cavities may have a different shape. For example, a cross-section of the reaction cavity may be oval-shaped, square-shaped, rectangular, other polygonal shape, or the like. Yet in other embodiments, the nanostructures may be located along a planar surface.

FIG. 8A is a perspective view of a nanoplug 402 in a reaction cavity 404, which may also be referred to as a nanowell. The nanoplug 402 may comprise gold (Au). In the illustrated embodiment, the nanoplug 402 is centrally located within the reaction cavity 404, but it may have other positions in other embodiments. FIG. 8B is a perspective view of a bowtie antenna 406 that may be use within one or more embodiments. The bowtie antenna 406 includes two separate nanostructures 408 that are triangular in shape and point to each other with a small gap therebetween. The bowtie antenna 406 may form an ensemble amplifier. FIG. 8C illustrates a nanograting 410 in a reaction cavity 412 that includes a series of spaced-apart beams 411. The nanograting 410 may be formed in a lower layer and subsequently exposed when the reaction cavity 412 is formed above the nanograting 410. As shown, the nanograting 410 is not confined within the reaction cavity 412 and extends beyond the wall of the reaction cavity 412. FIG. 8D illustrates a plurality of nanoparticles 414 disposed within a reaction cavity 416. The nanoparticles 414 may be distributed in random locations within the reaction cavity 416. The nanoparticles 414 may be formed, for example, through a reflow or deposition process. FIG. 8E illustrates a dimer 420 and a trimer 422. The dimer 420 and the trimer 422 may be disposed within alone in a single reaction cavity (not shown) without other nanostructures disposed therein. Alternatively, the dimer 420 and trimer 422 may share a common reaction cavity. Optionally, the dimer 420 and trimer 422 are not disposed within reaction cavities and, instead, are distributed along a planar surface (not shown).

FIGS. 9A-9D illustrate side cross-sections of reaction cavities having nanostructures disposed therein. The reaction cavities may be, for example, cylindrical or rectangular-shaped. In FIG. 9A, a reaction cavity 430 is shown that includes a plurality of nanostructures 432. The nanostructures 432 are posts that may be cylindrical or square-shaped. In FIG. 9B, a reaction cavity 434 is shown that includes a plurality of nanostructures 436. The nanostructures 436 may be conical or pyramidal. In FIG. 9C, a reaction cavity 438 is shown that includes a plurality of nanostructures 440. Each of the nanostructures 440 may be conical or pyramidal and have a particle portion 442 disposed at a top of the nanostructure 440. In FIG. 9D, a reaction cavity 444 is shown that includes a plurality of nanostructures 446. The nanostructures 446 constitute sidewalls that face each other.

FIGS. 10A-10D illustrate plan views of reaction cavities having one or more nanostructures disposed therein. More specifically, FIG. 10A illustrates a nanoring 450 that surrounds a central axis 452. The nanoring 450 is circular in FIG. 10A, but may have other shapes (e.g., polygonal) in other embodiments. FIG. 10B illustrates five posts 454 that are positioned relative to one another. FIGS. 10C and 10D show bowtie antennas 456, 458, respectively. The bowtie antennas 456, 458 are configured to preferentially respond to different polarizations of light.

In each of FIGS. 8A-8C, 9A-9D, and 10B-10D, the nanostructures may be configured to form a corresponding ensemble amplifier that is orientation dependent such that the ensemble amplifier preferentially responds to a polarized light of a designated orientation. Such ensemble amplifiers may be referred to as polarized amplifiers. For example, the ensemble amplifiers may be configured to have a dipole moment that is essentially parallel to an excitation light of a designated polarization. The amount of light emissions provided by reaction cavities having such polarized amplifiers is dependent upon the polarization of the excitation light.

In other embodiments, the ensemble amplifiers may be configured to preferentially respond to light emissions of a predetermined wavelength. For example, if the emitters provide light emissions that are equal to or near the predetermined wavelength, the ensemble amplifiers may amplify the light emissions. However, if the emitters provide light emissions that are not equal to or near the predetermined wavelength, the ensemble amplifiers may only partially amplify the light emissions or amplify the light emissions by a negligible amount.

Figure 11:
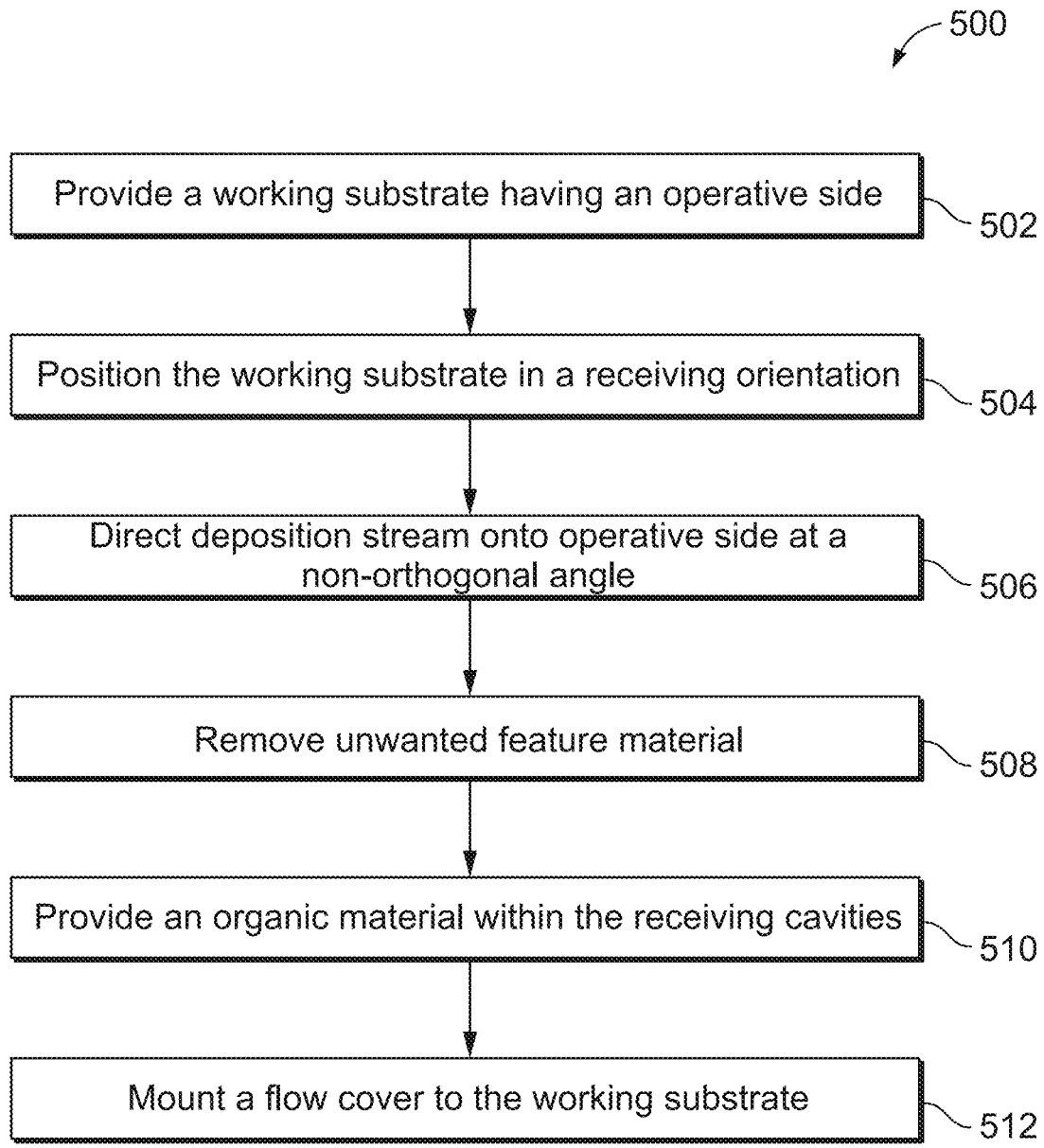
FIG. 11 is a flow chart illustrating a method of manufacturing a structured substrate in accordance with an embodiment.

FIG. 11 is a flowchart illustrating a method 500 of manufacturing or fabricating a structured substrate. The method may include performing one or more additive or subtractive techniques, such as those described above. In some embodiments, the method 500 includes steps that are similar or identical to the steps of the methods 200 (FIG. 2), 220 (FIG. 3), and 300 (FIG. 6). Different stages of the method 500 are illustrated in FIGS. 12-15. The method 500 includes providing, at 502, a working substrate 522 having an operative side 523. The working substrate 522 may represent an unfinished or incomplete structured substrate. The working substrate 522 may be similar to one or more of the base layers and/or other working substrates described herein. For example, the working substrate 522 may include one or more structures (e.g., layers, features, and the like) that have been provided using the additive and subtractive techniques described above.

The operative side 523 has a non-planar contour that includes a side surface 524 and an array of receiving cavities 526 that open to the side surface 524. In the illustrated embodiment, the side surface 524 is planar between the receiving cavities 526. The side surface 524 is not required to be planar, however, and may include projections or other features. As described herein, embodiments may utilize the non-planar contour of the operative side 523 to form nanostructures at desired locations along the operative side 523, such as within the receiving cavities 526.

Figures 12, 13:
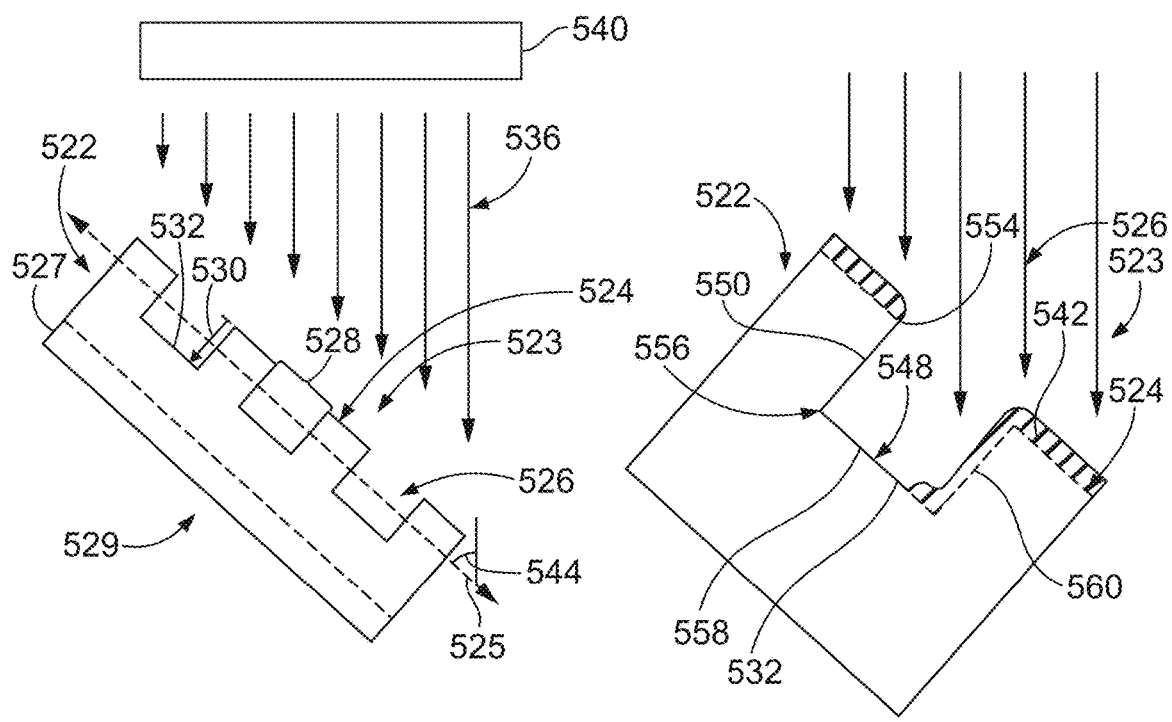
FIG. 12 illustrates a side view of a deposition step during the manufacture of the structured substrate of FIG. 11.
FIG. 13 is an enlarged cross-sectional view of a reaction cavity during the deposition step of FIG. 12.

Each of the receiving cavities 526 has an opening 528 along the side surface 524. The side surface 524 includes interstitial regions that extend between and separate adjacent openings 528. Each of the receiving cavities 526 extends a depth 530 from the corresponding opening 528 into the working substrate 522 to a bottom surface 532. As shown in FIG. 12, the receiving cavities 526 coincide with an array plane 525. More specifically, the array plane 525 may intersect each of the receiving cavities 526. In some embodiments, the array plane 525 extends parallel to the side surface 524 and/or one or more of the layers that form the working substrate 522. For example, a glass wafer 527 may form a bottom layer of the working substrate 522. The array plane 525 may extend parallel to the glass wafer 527.

The method 500 may also include positioning, at 504, the working substrate 522 in a receiving orientation 529, which may also be referred to as the first receiving orientation in some embodiments. The method 500 may also include directing, at 506, a deposition stream 536 onto the operative side 523 of the working substrate 522. The deposition stream 536 may be provided by a deposition source 540. The deposition stream 536 includes a feature material 542 (shown in FIG. 13). In particular embodiments, the deposition stream 536 is provided in a substantially linear manner (e.g., in one direction along an axis). As such, the directing operation at 506 may be characterized as line-of-sight deposition. For example, the deposition source 540 is an electron beam evaporation system. However, it is contemplated that other line-of-sight deposition sources may be used.

In particular embodiments, the feature material 542 is a plasmon resonant material that accumulates along the operative side 523 to directly form nanostructures that are configured to amplify electromagnetic energy as set forth herein. However, in other embodiments, the feature material 524 may not be a plasmon resonant material. In such embodiments, the feature material 524 may be used to indirectly form nanostructures. For example, the feature material 542 may form nanobodies and a plasmon resonant material may be subsequently deposited over the nanobodies to form nanostructures capable of amplifying electromagnetic energy.

In FIG. 12, the deposition stream 536 appears as a plurality of separate streams. In some embodiments, the deposition stream 536 may be a single stream that is scanned along the operative side 523. For example, the deposition source and/or the working substrate 522 may be moved relative to one another so that the deposition stream 536 moves along the operative side 523. In other embodiments, multiple deposition streams 536 may be applied concurrently. Optionally, a mask having apertures may be positioned between the deposition source 540 and the working substrate 522 to block the deposition stream 536 during portions of the deposition operation.

The directing, at 506, may include directing the deposition stream 536 at a non-orthogonal angle 544 with respect to the working substrate 522 when the working substrate 522 is in the receiving orientation 529. For example, the directing, at 506, may include directing the deposition stream 536 at the non-orthogonal angle 544 with respect to the array plane 525. Additionally or alternatively, the non-orthogonal angle 544 may be with respect to the side surface 524. The non-orthogonal angle 544 may be, for example, between 5° and 85°. In some embodiments, the non-orthogonal angle 544 is between 10° and 75°. In particular embodiments, the non-orthogonal angle 544 is between 15° and 60°.

FIG. 13 is an enlarged side view of an exemplary receiving cavity 526 during the directing, at 506 (i.e., during a deposition process), when the working substrate 522 is in the receiving orientation 529 (FIG. 12). As shown, the receiving cavity 526 is defined by a cavity surface 548. The cavity surface 548 may be a single surface having a curved contour or separate surfaces that are joined at, for example, corners. For instance, the cavity surface 548 includes a wall surface 550 and the bottom surface 532 that includes a maximum depth of the receiving cavity 526. The wall surface 550 may be a single circular or curved surface. Alternatively, the wall surface 550 may include multiple surfaces that are joined at, for example, corners of the receiving cavity 526. The wall surface 550 extends from an opening edge 554 that intersects the side surface 524 to a corner 556 formed with the bottom surface 532.

The directing, at 506, is configured to utilize the non-planar contour of the operative side 523 of the working substrate 522 to block portions of the deposition stream 536 from entering the receiving cavities 526 and to allow other portions of the deposition stream 536 to enter the receiving cavities 526. For example, if multiple deposition streams are concurrently incident on the operative side 523, then the non-planar contour would block one or more of the deposition streams from entering the receiving cavities 526. If a single deposition stream is scanned (e.g., moved) along the operative side 523, then the non-planar contour may block the deposition stream for a portion of the scan time. In this manner, the feature material 542 may accumulate in selected areas along the cavity surface 548.

For example, in FIG. 13, the working substrate 522 is positioned in the receiving orientation 529 relative to a linear path of the deposition stream 536. In the receiving orientation 529, a shadow area 558 is formed along the cavity surface 548. The shadow area 558 is indicated in FIG. 13 as a solid line that extends along the cavity surface 548. In an exemplary embodiment, the shadow area 558 includes at least a portion of the wall surface 550 and at least a portion of the bottom surface 532.

In the receiving orientation 529, an incident area 560 is also formed along the cavity surface 548. In the illustrated embodiment, the incident area 560 includes at least a portion of the wall surface 550 and at least a portion of the bottom surface 532. The incident area 560 is indicated in FIG. 13 as a dashed line that extends along the cavity surface 548 and also along the side surface 524.

During the deposition process, the feature material 542 of the deposition stream 536 is permitted to pass through the opening 528 and accumulate along the incident area 560 within the receiving cavity 526. The feature material 542, however, does not accumulate along the shadow area 558. Instead, the side surface 524 blocks or obstructs the deposition stream 536 from entering the receiving cavity 526 and being incident on the shadow area 558. Accordingly, after the deposition process, at 506, one portion of the cavity surface 548 (e.g., the incident area 560) includes feature material 542 thereon, but another portion (e.g., the shadow area 558) is devoid of the feature material 542.

In some embodiments, the method 500 includes repeating the positioning, at 504, and the directing, at 506. For example, the working substrate 522 may be re-positioned in a different second receiving orientation and another deposition stream may be provided onto the working substrate 522. In alternative embodiments, the rotation may occur while the deposition stream 562 is provided to the working substrate 522.

Figures 14, 15:
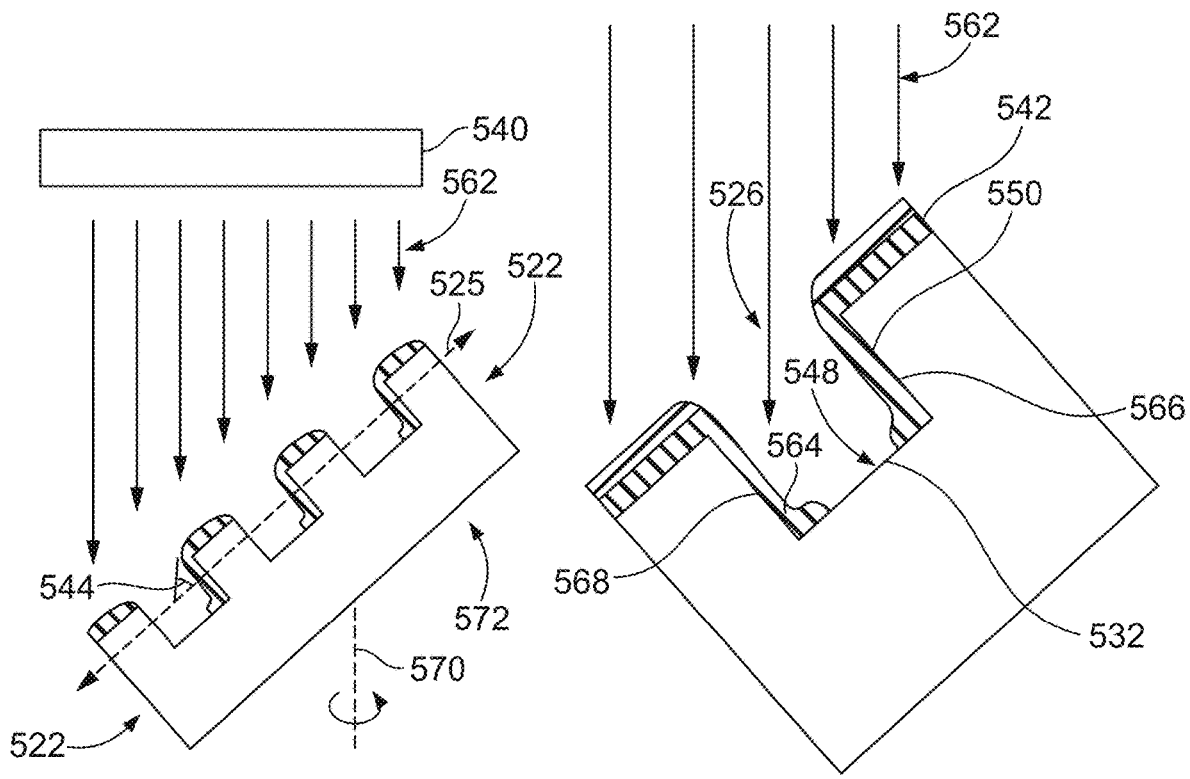
FIG. 14 illustrates a side view of another deposition step during the manufacture of the structured substrate of FIG. 11.
FIG. 15 is an enlarged cross-sectional view of the reaction cavity during the deposition step of FIG. 13.

FIGS. 14 and 15 illustrate the second deposition process. In FIGS. 14 and 15, the deposition stream is referenced as a deposition stream 562. The deposition stream 562 may include a feature material 564 that is identical to or different from the feature material 542 (FIG. 13). In FIGS. 14 and 15, the working substrate 522 is in a second receiving orientation 572 that is different from the first receiving orientation 529. The working substrate 522 may be moved in any amount or direction to the second receiving orientation 572. For example, relative to the working substrate 522 in FIG. 12, the working substrate 522 may be rotated about a central axis 570 that extends substantially parallel to the path of the deposition stream 562. The working substrate 522 may be rotated, for example, +/−45, 90, 135, 180 relative to the first receiving orientation 520 to be positioned in a second receiving orientation 572. The working substrate 522 may also be rotated about other axes that are perpendicular to the central vertical axis 570. For example, the working substrate 522 may be rotated about an axis that is perpendicular to the central axis 570 to increase or decrease the non-orthogonal angle 544.

As shown in FIG. 15, in the second receiving orientation 572, a second shadow area 566 (indicated by solid line) and a second incident area 568 (indicated by dashed line) are formed in each receiving cavity 526. In some embodiments, the second shadow area 566 may at least partially overlap with the first incident area 560 (FIG. 13), and the second incident area 568 may at least partially overlap the first shadow area 558 (FIG. 13). In the illustrated embodiment, the second shadow area 566 includes at least a portion of the wall surface 550 and at least a portion of the bottom surface 532. In the illustrated embodiment, the second incident area 568 includes at least a portion of the wall surface 550 and at least a portion of the bottom surface 532.

During the second deposition process, the feature material 564 of the deposition stream 562 is permitted to pass through the opening 528 and accumulate along the incident area 568 within the receiving cavity 526. In some embodiments, if the feature material 542 is located along the incident area 568, then the feature material 564 may accumulate over the feature material 542. In some embodiments, if the feature material 542 is not located along the incident area 568, then the feature material 564 may accumulate directly over the incident area 568 of the cavity surface 548.

The feature material 564, however, does not accumulate along the second shadow area 566. Instead, the side surface 524 blocks or obstructs the deposition stream 562 from entering the receiving cavity 526. Accordingly, after the second deposition process a portion of the cavity surface 548 includes the feature material 564 therealong, but the other portion is devoid of the feature material 564. The portion devoid of the feature material 564, however, may already include the feature material 542.

In some embodiments, the feature material 542 may form one nanostructure, and the feature material 564 may form another nanostructure. Optionally, the positioning, at 504, and the directing, at 506, may be repeated one or more times to build nanobodies and/or nanostructures within the receiving cavities 526. Collectively, the nanostructures within each receiving cavity 526 may form an ensemble amplifier as described herein.

After depositing the feature material(s) along the operative side 523, extraneous or unwanted feature material(s) along the side surface 524 may be removed, at 508. For example, the side surface 524 may be polished to remove the feature material(s) and/or another subtractive technique may be applied to remove the feature material(s). Optionally, at 510, an organic material (not shown), such as the gel material described herein, may be provided. The organic material may cover the nanostructures in the receiving cavities 526. Optionally, prior to adding the organic material, the nanostructures may be coated with a plasmon resonant material and/or passivation layer as described herein. At 512, a flow cell may be mounted to the working substrate.

Figures 16, 17, 18:
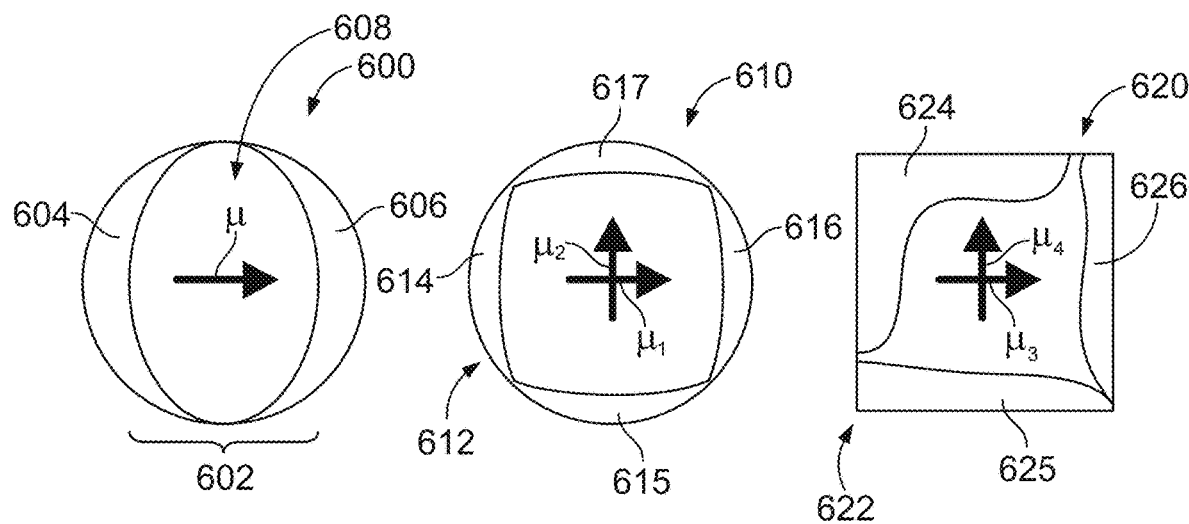
FIG. 16 is an enlarged view of a reaction cavity formed in accordance with an embodiment.
FIG. 17 is an enlarged view of a reaction cavity formed in accordance with an embodiment.
FIG. 18 is an enlarged view of a reaction cavity formed in accordance with an embodiment.

FIG. 16 is a plan view of a reaction cavity 600 having an ensemble amplifier 602 that includes nanostructures 604, 606. In some embodiments, the reaction cavity 600 and the ensemble amplifier 602 may be manufactured, for example, using the method 500 (FIG. 11). For example, the nanostructure 604 may be formed during a first deposition process, and the nanostructure 606 may be formed during a second deposition process after re-positioning the working substrate. The nanostructures 604, 606 are located on opposite sides of the reaction cavity 600 and oppose each other with a gap 608 therebetween.

In some embodiments, the ensemble amplifier 602 is a polarized amplifier that is configured to preferentially respond to electromagnetic energy of a predetermined polarization. For example, the ensemble amplifiers 602 may be configured to have a dipole moment $\mu$ that may be essentially parallel to an excitation light of a predetermined polarization. When the electromagnetic energy of the predetermined polarization is incident on the ensemble amplifier 602, the reaction cavity 600 and/or the ensemble amplifier 602 may preferentially respond to the excitation light. More specifically, the signal intensity of the light emissions provided by the reaction cavity 600 is greater when the dipole moment μ of the ensemble amplifier 602 is parallel to the polarization of the excitation light compared to when the dipole moment μ of the ensemble amplifier 602 is not parallel to the polarization of the excitation light. In other words, the signal intensity of the light emissions provided by reaction cavity 600 in response to the excitation light is dependent upon the polarization of the excitation light.

FIG. 17 is an enlarged view of a reaction cavity 610 having an ensemble amplifier 612 that includes nanostructures 604-607. In some embodiments, the reaction cavity 610 and the ensemble amplifier 612 may be manufactured, for example, using the method 500 (FIG. 11) and multiple different receiving orientations. For example, the nanostructure 614 may be formed during a first deposition process, the nanostructure 615 may be formed during a second deposition process, the nanostructure 616 may be formed during a third deposition process, the nanostructure 617 may be formed during a second deposition process. In some embodiments, the material that forms the nanostructures 614-617 is the same material. In other embodiments, however, one or more of the nanostructures 614-617 may include a different material.

The ensemble amplifier 612 may have two dipole moments $\mu_1$ nd $\mu_2$. The nanostructures 614, 616 are located on opposite sides of the reaction cavity 610, and the nanostructures 615, 617 are located on opposite sides of the reaction cavity 610. In such embodiments, the ensemble amplifier 612 may preferentially respond to two different polarizations of excitation light.

FIG. 18 is an enlarged view of a reaction cavity 620 having an ensemble amplifier 622 that includes nanostructures 624-626. In some embodiments, the reaction cavity 620 and the ensemble amplifier 622 may be manufactured, for example, using the method 500 (FIG. 11) and multiple different receiving orientations. For example, the nanostructure 624 may be formed during a first deposition process, the nanostructure 625 may be formed during a second deposition process, the nanostructure 626 may be formed during a third deposition process. In an exemplary embodiment, the material that forms the nanostructures 624-626 are different materials. In other embodiments, however, the material may be the same.

The ensemble amplifier 622 may have two dipole moments $\mu_3$ and $\mu_4$. For example, a portion of the nanostructures 624 is located opposite the nanostructure 625, and another portion of the nanostructures 624 is located opposite the nanostructure 626. In such embodiments, the ensemble amplifier 622 may preferentially respond to two different polarizations of excitation light. It should be noted, however, that the preferential responses may not be equal. For example, the signal intensity provided when the dipole moment $\mu_3$ is parallel to the polarization of the excitation light may be different from the signal intensity provided when the dipole moment $\mu_4$ is parallel to the polarization of the excitation light. The difference in signal intensity may be caused by the different materials used to form the nanostructures 625 and 626.

Although not shown in FIGS. 16-18, one or more embodiments may include individual nanostructures that are formed from two or more plasmon resonant materials. Moreover, one or more of the individual nanostructures may be formed during multiple depositions processes. For example, a portion of the nanostructure 624 may comprise gold (Au) and another portion of the nanostructure 624 may comprise silver (Ag).

Figure 19:
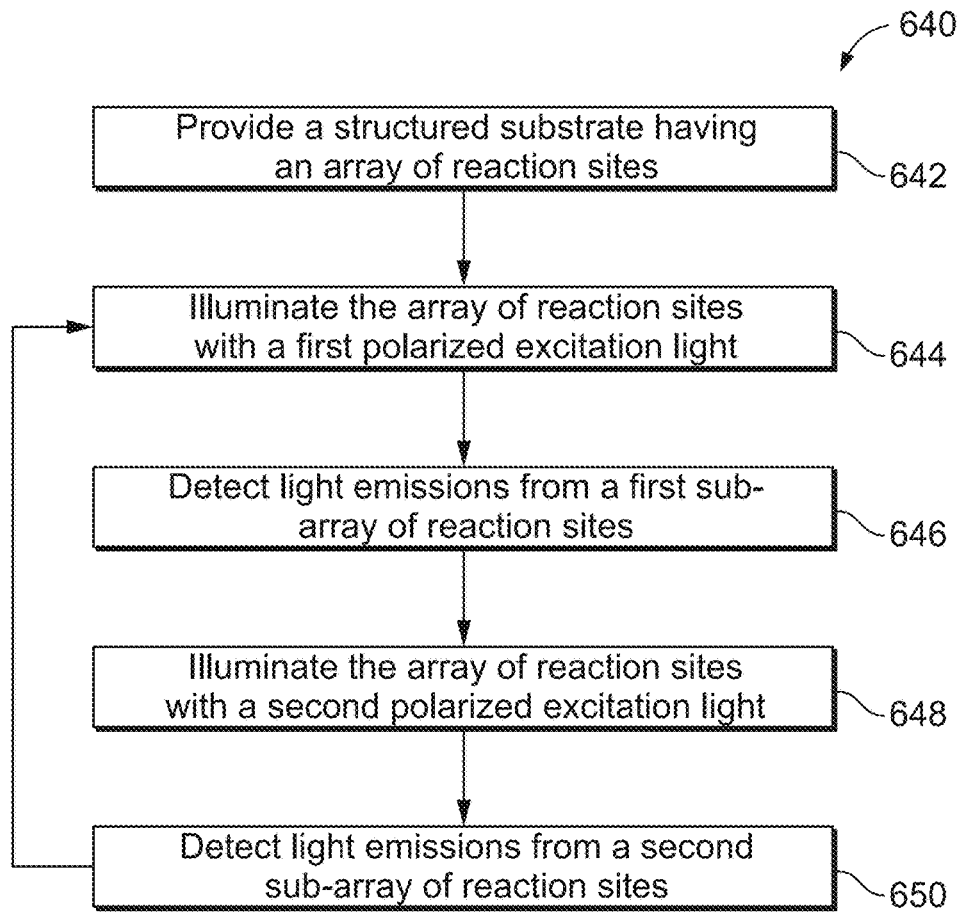
FIG. 19 is a flow chart illustrating a method of detecting light emissions is accordance with an embodiment.

FIG. 19 is a flowchart illustrating a method 640. The method 640 may be, for example, a method of conducting an assay protocol in which a sequence of fluidic and imaging steps occur. In some embodiments, the method 640 is a method of detecting light emissions. The method 640 is described in reference to FIGS. 20 and 21, which illustrate an array 662 of reaction sites 664. The method 640 includes, at 642, providing a structured substrate having an array 662 of reaction sites 664. The structured substrate may be, for example, similar or identical to the structured substrates described herein. In the illustrated embodiment, the reaction sites 664 are reaction cavities, but it should be understood that other embodiments may include reaction areas distributed along, for example, a common planar surface. The reaction sites 664 may be similar to, for example, the reaction cavity 600 (FIG. 16). Each of the reaction sites 664 includes an ensemble amplifier 668 that is a polarized amplifier. The ensemble amplifiers 668 are configured to preferentially respond to electromagnetic energy having a predetermined polarization. The ensemble amplifiers 668 preferentially respond by amplifying the electromagnetic energy.

The array 662 of reaction sites 664 include first and second sub-arrays 670, 672, which are shown in FIGS. 21 and 22, respectively. The first sub-array 670 includes reaction sites 664A having ensemble amplifiers 668A, and the second sub-array 672 includes reaction sites 664B having ensemble amplifiers 668B. The ensemble amplifiers 668A of the first sub-array 670 are configured to preferentially respond to a first polarized excitation light. The ensemble amplifiers 668B of the second sub-array 672 are configured to preferentially respond to a different second polarized excitation light. The first and second polarized excitation lights may differ by, for example, about 90°. However, the difference may be smaller or greater depending upon the application and configuration of the ensemble amplifiers.

In the illustrated embodiment, the reaction sites 664A and 664B have effectively the same ensemble amplifier 668. More specifically, each of the ensemble amplifiers 668 includes a pair of nanostructures that are positioned relative to one another in the same manner. For example, the nanostructures have the same shape and directly oppose each other. However, the ensemble amplifiers 668A and 668B have different first and second orientations such that the ensemble amplifiers 668A have a dipole moment $\mu_5$ and the ensemble amplifiers 668B have a dipole moment $\mu_6$. The dipole moments $\mu_5$ and $\mu_6$ differ by about 90°, but may differ by other amounts in other embodiments.

Turning to FIG. 21, the method 640 includes illuminating, at 644, the array 662 of reaction sites 664 with a first polarized excitation light (or an excitation light having a first polarization). In some embodiments, the entire array 662 is illuminated when the array 662 is illuminated with the first polarized excitation light. More specifically, each of the first and second sub-arrays 670, 672 may be illuminated. In other embodiments, however, only portions of the array 662 is illuminated when the array 662 is illuminated with the first polarized excitation light. For example, only the first sub-array 670 may be illuminated.

At 646, the light emissions from the first sub-array 670 may be detected. Each of the reaction sites 664A in the first sub-array 670 is configured to amplify the excitation light having the first polarization. In some embodiments, the amplification may cause a greater intensity of light emissions from a biomolecule or analyte (e.g., nucleic acids) located at or within the reaction site 664A. For example, if the biomolecule or analyte includes a plurality of fluorescent labels, the fluorescent labels may experience a greater intensity of excitation light and, consequently, provide a greater response to the excitation light. It should be noted that, for some embodiments, one or more of the reaction sites 664A may not include a biomolecule or analyte having the fluorescent labels. For example, if the desired reaction did not occur at or within the reaction site 664A, the reaction site 664 may not have fluorescent labels capable of responding.

For illustrative purposes, FIG. 21 more clearly shows the first sub-array 670 of reaction sites 664A. In some embodiments, the reaction sites 664B (indicated by circles in FIG. 21) may provide a partial response when excited by the excitation light of the first polarization. For example, the reaction sites 664B may emit a signal intensity that is, 40% or less than the average signal intensity provided by the reaction sites 664A that have the designated emitters (e.g., fluorescent labels). More specifically, if the average signal intensity from the reaction sites 664B having the designated emitters is Y, then the reaction sites 664B having the designated emitters may provide, at most, 0.4Y. In such embodiments, the imaging system may identify those locations as providing an insufficient or inadequate response. In particular embodiments, the reaction sites 664B having the designated emitters may emit a signal intensity that is, on average, 30% or less, 20% or less, or 10% or less than the average signal intensity provided by the reaction sites 664A.

With respect to FIG. 22, the method 640 also includes illuminating, at 648, the array 662 of reaction sites 664 with the second polarized excitation light. As described above, in some embodiments, the entire array 662 is illuminated when the array 662 is illuminated with the second polarized excitation light. In other embodiments, however, only portions of the array 662 is illuminated when the array 662 is illuminated with the second polarized excitation light. For example, only the second sub-array 672 may be illuminated.

At 650, the light emissions from the second sub-array 672 may be detected. Each of the reaction sites 664B in the second sub-array 672 is configured to amplify the excitation light having the second polarization. The amplification of the excitation light may cause a greater intensity of light emissions from a biomolecule or analyte (e.g., nucleic acids) located at the reaction site 664B. For example, if the biomolecule or analyte includes a plurality of fluorescent labels, the fluorescent labels may experience a greater intensity of excitation light and, consequently, provide a greater response to the excitation light. As described above, it should be noted that one or more of the reaction sites 664B may not include a biomolecule or analyte having the fluorescent labels in some embodiments.

For illustrative purposes, FIG. 22 more clearly shows the second sub-array 672 of reaction sites 664B. In some embodiments, the reaction sites 664A (indicated by circles in FIG. 22) may provide a partial response when excited by the excitation light of the second polarization. For example, the reaction sites 664A may emit a signal intensity that is, 40% or less than the average signal intensity provided by the reaction sites 664B that have the designated emitters (e.g., fluorescent labels). More specifically, if the average signal intensity from the reaction sites 664B having the designated emitters is Z, then the reaction sites 664A having the designated emitters may provide, at most, 0.4Z. In such embodiments, the imaging system may identify those locations as providing an insufficient or inadequate response. In particular embodiments, the reaction sites 664A having the designated emitters may emit a signal intensity that is, on average, 30% or less, 20% or less, or 10% or less than the average signal intensity provided by the reaction sites 664B.

The embodiment described with respect to FIGS. 19-22 may be suitable for high density arrays. For example, returning to FIG. 20, the reaction sites 664 form rows 691 and columns 692. The reaction sites 664 within a common row 691 may have a center-to-centering spacing 684, and the reaction sites 664 within a common column 692 may have a center-to-center spacing 686. In the illustrated embodiment, the ensemble amplifiers 668A, 668B are positioned relative to each other within the array 662 such that each reaction site 664A (or ensemble amplifier 668A) is closer to reaction sites 664B (or ensemble amplifiers 668B) than to another reaction site 664A (or ensemble amplifier 668A). For example, the center-to-center spacing 684 between adjacent ensemble amplifiers 668 in a common row may be about x measured in, for example, nanometers (nm), and the center-to-center spacing 686 between adjacent ensemble amplifiers 668 in a common column may be about x. Adjacent reaction sites 664 having the same polarized amplifier may have a center-to-center spacing 688. As shown, the center-to-center spacing 688 is greater than each of the center-to-center spacings 684, 686. For example, the center-to-center spacing 688 may be about 1.4x. In other embodiments, the center-to-center spacing 688 may be at least about 1.2x, at least about 1.3x, at least about 1.5x, at least about 1.6x, at least about 1.7x, at least about 1.8x, at least about 1.9x, or at least about 2x. By way of example, the center-to-center spacings 684, 686 may be about 350 nm, and the center-to-center spacing 688 may be about 500 nm. In other embodiments, the center-to-center spacings 684, 686 may be about 200 nm, 250 nm, 300 nm, 400 nm, 450 nm, 500 nm, 600 nm, 700 nm, 800 nm, or more. Although the center-to-center spacings 684, 686 are essentially equal in the illustrated embodiment, the center-to-center spacings 684, 686 may differ in other embodiments.

Accordingly, in some embodiments, neighboring reaction sites, such as those that are in the same column or in the same row, may have a center-to-center spacing that is not optically resolvable by the imaging system. If such neighboring reaction sites were imaged simultaneously, each of the reaction sites would emit fluorescence simultaneously. The imaging system may not be able to differentiate between these neighboring reaction sites. In contrast, the imaging system may be able to differentiate between neighboring reaction sites having different ensemble amplifiers. In such an arrangement, reaction sites with the same ensemble amplifier may have a larger center-to-center spacing. This larger center-to-center spacing may be a distance that is within the imaging resolution of the system. Thus, by including ensemble amplifiers that respond to different polarizations of excitation light, some of the reaction sites (first reaction sites) would be imageable with a first scan in which the excitation light has a first polarization and other reaction sites (second reaction sites) would be imageable with a second scan in which the excitation light has a second polarization. The first and second reaction sites may be positioned relative to one another so that the center-to-center spacings between first reaction sites is increased and the center-to-center spacings between second reaction sites is increased.

For some embodiments, the method 640 may include repeating steps 644, 646, 648, and 650 a plurality of times. As an example, the sequence of steps 644, 646, 648, 650 may be repeated 20 times, 40 times, 60 times, 80 times, 100 times, 120 times, 140 times, 160 times, 180 times, 200 times, or more. The method 640 may be part of a sequencing by synthesis (SBS) protocol as described herein in which the sequence of steps 644, 646, 648, 650 is performed after the incorporation of labeled nucleotides to clusters or colonies of nucleic acids. For example, prior to performing the sequence of steps 644, 646, 648, 650, a liquid comprising labeled reagents (e.g., nucleotides) may be directed along the reaction sites 664 to allow the nucleotides to be added to the nucleic acids. A subsequent wash step may be directed along the reaction sites 664 to remove the unincorporated reagents. After the unincorporated reagents are removed, the sequence of steps 644, 646, 648, 650 may be performed to detect the light emissions and determine which nucleotide was incorporated by the clusters. After detecting the light emissions, the labels may be removed and another cycle of incorporating and detecting the nucleotides may begin.

Although FIGS. 19-22 illustrate an embodiment in which there are only two sub-arrays, it should be understood that other embodiments may include multiple sub-arrays. For example, alternative embodiments may have three, four, five, or more different polarized amplifiers.

FIGS. 23-41 illustrate different methods of manufacturing or fabricating structured substrates that include nanostructures. In some cases, the nanostructures may form ensemble amplifiers as described above. The structured substrates set forth below and elsewhere in the present application may be used to conduct designated chemical reactions for analyzing biological or chemical substances. In particular embodiments, the structured substrates may be used during an SBS protocol.

For various embodiments, such as those described above and below, it is understood that one or more sites (e.g., cavities or localized areas on a surface) of a structured substrate may include nanoparticles that are not suitably positioned relative to one another such that the light emissions and/or excitation light can be amplified. Nonetheless, the methods set forth herein may be capable of providing structured substrates in which a significant number of sites may be capable of amplifying the electromagnetic energy. For example, in some embodiments, more than 50% of the sites may have nanoparticles that are capable of amplifying the electromagnetic energy. In some embodiments, more than 60% or 70% of the sites may have nanoparticles that are capable of amplifying the electromagnetic energy. In particular embodiments, more than 80% or 90% of the sites may have nanoparticles that are capable of amplifying the electromagnetic energy.

FIG. 23 is a flowchart illustrating a method 700 of manufacturing or fabricating a structured substrate. The method 700 may include performing one or more additive or subtractive techniques, such as those described above. The method 700 is illustrated, separately, in FIGS. 24 and 25. The method 700 may be similar to the other methods of manufacturing described herein and may include one or more steps of the other methods. In an exemplary embodiment, the method 700 includes providing, at 702, a base layer 712 having a base side 714 and providing, at 704, a feature layer 716 along the base side 714. In FIG. 24, the feature layer 716 is a continuous, planar layer that is substantially devoid of recess and extends throughout the base side 714. In FIG. 25, however, the feature layer 716 is non-planar and includes designated recesses 718. The designated recesses 718 may be formed through, for example, NIL as described above. The feature layer 716 may include a resin. For example, the feature layer 716 may comprise EVG or other material that is suitable for NIL.

At 706, the method 700 may include forming nanobodies 720 using reactive-ion etching (ME). RIE may be used to remove material having a designated chemistry. For example, the feature layer 716 may comprise a carbon-based material. The RIE may include a chemically-reactive plasma that is configured to remove the material of the feature layer 716 when applied thereto. For instance, the RIE may include using an oxygen plasma to remove portions of the carbon-based material of the feature layer 716. It should be understood, however, that the above is only one example and other materials may be used for the RIE or the feature layer 716.

As shown in FIGS. 24 and 25, the ME may provide an irregular surface along the feature layer 716 that forms peaks 722 and recesses or troughs 724. The peaks 722 and recesses 724 may define the nanobodies 720. The peaks 722 may be separated from adjacent peaks by a peak-to-peak distance 726. The peak-to-peak distances 726 and sizes of the nanobodies 726 appear irregular in FIGS. 24 and 25. In some embodiments, the RIE process may be configured to achieve an average peak-to-peak distance 726. In some embodiments, the RIE process may be configured to provide a majority of the peak-to-peak distances 726 within a designated range. Various parameters may be selected to achieve a desired result. For example, the parameters may include the material for the feature layer 716, the material or type of ME, the etch time, the thickness of the feature layer 716, and/or the pitch or distribution of the recesses 718.

As shown in FIG. 25, the nanobodies 720 may form groups or ensembles 730 that are separated from other groups 730 by an area 732 of the base side 714. Each of the groups 730 includes a plurality of nanobodies 720. The locations of the areas 732 may correlate to the locations of the recesses 718 prior to ME. More specifically, the reduced thickness of the feature layer 716 at the recesses 718 results in the ME process removing all of the material of the feature layer 716 such that the areas 732 are exposed. However, as shown in FIG. 24, the feature layer 716 may form a distribution of the nanobodies 720 across an entirety of the base side 714.

At 708, the etched feature layer 716 may be coated with a plasmon resonant material 734, such as gold (Au). At 710, a passivation layer 736 (e.g., $Ta_2O_5$) may be coated onto the plasmon resonant material 734. As shown, the irregular surface of the feature layer 716 may cause the passivation layer 736 to form peaks 738 and recesses 740. The peaks 738 and recesses 740 may form nanostructures 742 in which adjacent peaks 738 may correspond to adjacent nanostructures 742. As described herein, electromagnetic energy may be amplified by the adjacent nanostructures 742.

Each of the peaks 738 may be separated by a peak-to-peak distance 744. In the illustrated embodiment, the peak-to-peak distance 744 appears irregular or non-uniform. However, a majority of the peak-to-peak distances 744 may be within a designated range. For example, more than 75% of the peak-to-peak distances 744 may be between 0.5× and 1.5×, wherein X is greater than or equal to 1 nm and less than or equal to 1000 nm. By way of example, x may be less than 900 nm, 800 nm, 700 nm, 600 nm, or 500 nm. In particular embodiments, x may be less than 400 nm, 350 nm, 300 nm, 350 nm, or 200 nm. In more particular embodiments, x may be less than 150 nm, 100 nm, 75 nm, 60 nm, or 50 nm. Yet in more particular embodiments, x may be less than 40 nm, 30 nm, 20 nm, 15 nm, or 10 nm. As a specific example, more than 75% of the peak-to-peak distances 726 may be between 1 nm and about 50 nm. More specifically, more than 75% of the peak-to-peak distances 726 may be between 1 nm and about 25 nm. In certain embodiments, more than 75% of the peak-to-peak distances 726 may be between 1 nm and about 10 nm.

As shown in FIG. 25, the groups 730 may be used to form reaction sites or islands 732 in which each reaction site 732 is a localized group of nanostructures 742 that are formed from an irregular surface of the uppermost layer (e.g., passivation layer 736, plasmon resonant layer 734, or feature layer 716). The reaction sites 732 may be separated from one another by areas 746. Although not shown, the method 900 may also include providing an organic material (e.g., hydrogel), as described above, along the nanostructures 742.

Figure 26:
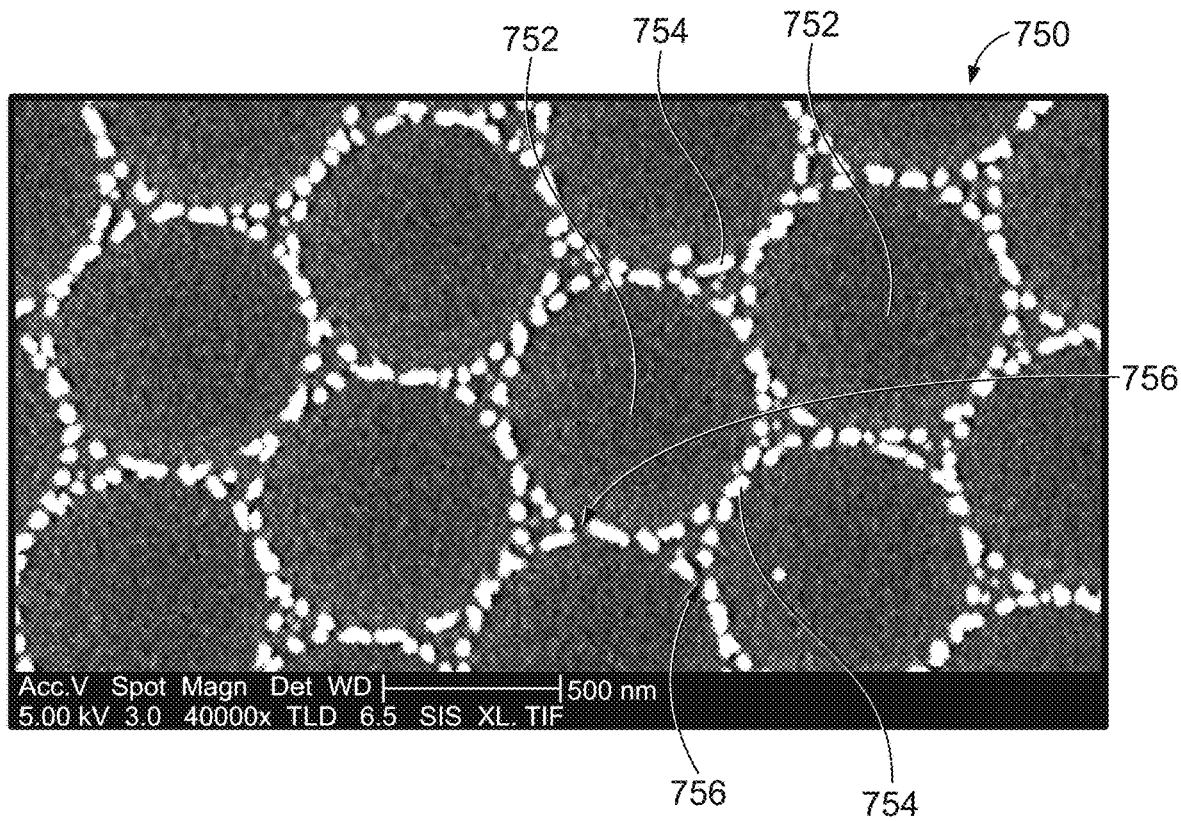
FIG. 26 is a scanning electron microscope (SEM) image of a working substrate that was formed using a method similar to the method of FIG. 23.
Figure 27:
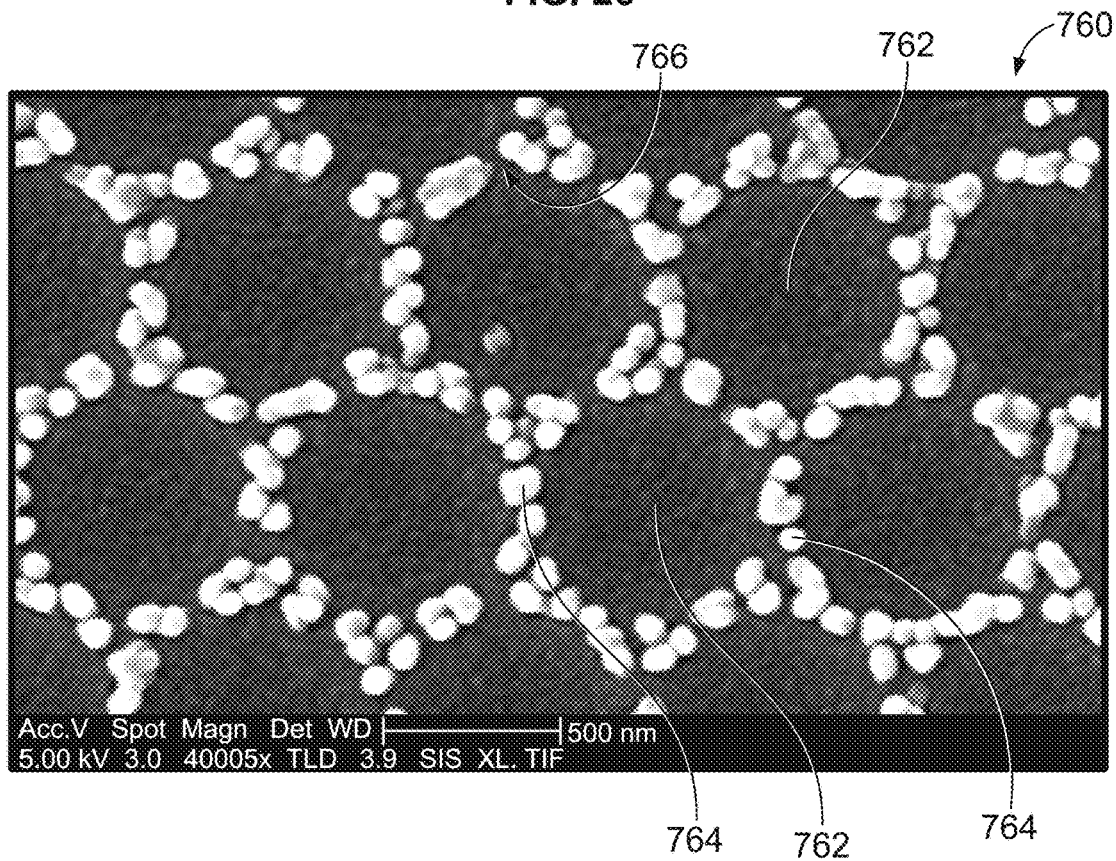
FIG. 27 is a scanning electron microscope (SEM) image of a working substrate that was formed using a method similar to the method of FIG. 23.
Figure 29:
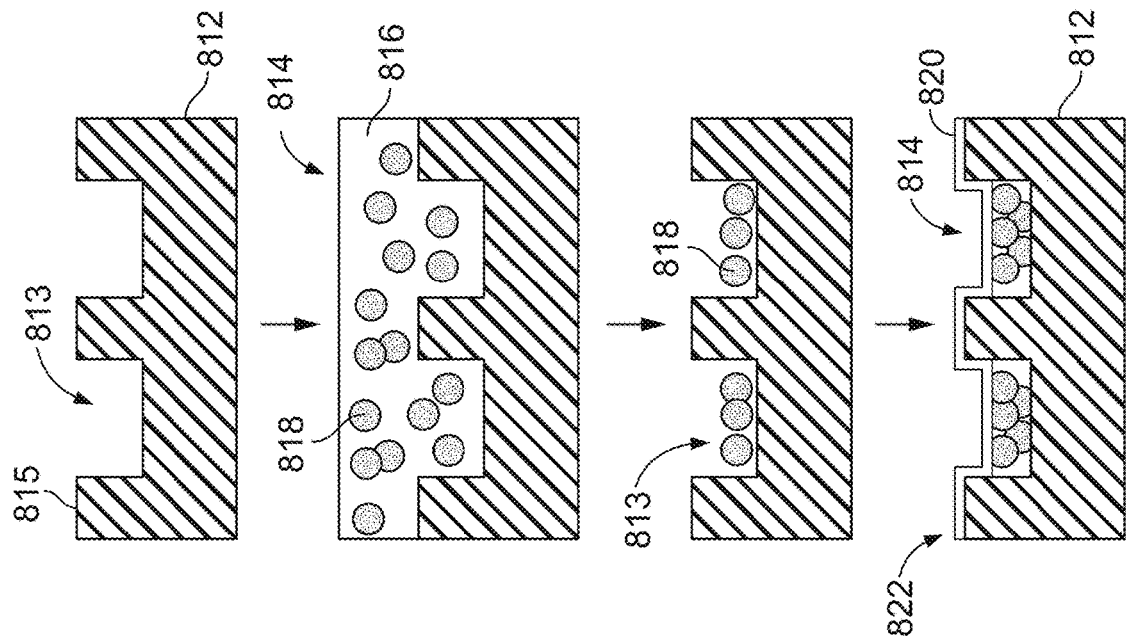
FIG. 29 is a side view illustrating different steps of the method shown in FIG. 28.

FIGS. 26 and 27 illustrate SEM images of structured substrates 750, 760, respectively, that were formed using a process that is similar to the method 700. In particular, a feature layer was provided and shaped to include recesses, which were similar to the recesses 718 (FIG. 25), that were defined by interstitial regions. After an RIE process, the recesses formed the areas 752 and 762. However, the interstitial regions formed the nanobodies 754, 764. The nanobodies 754 in FIG. 26 are smaller than the nanobodies 764 in FIG. 27. The sizes of the nanobodies 754, 764 and spaces 756, 766, respectively, between adjacent nanobodies may be based on various parameters, such as the material of the feature layer, duration of the RIE process, thickness of the feature layer, and the type of RIE plasma used. After the nanobodies 754, 765 are coated with a plasmon resonant material, it is contemplated that dye-labeled biological or chemical substances may be positioned within the spaces 756, 766 and the adjacent nanoparticles may form an ensemble amplifier.

Figure 28:
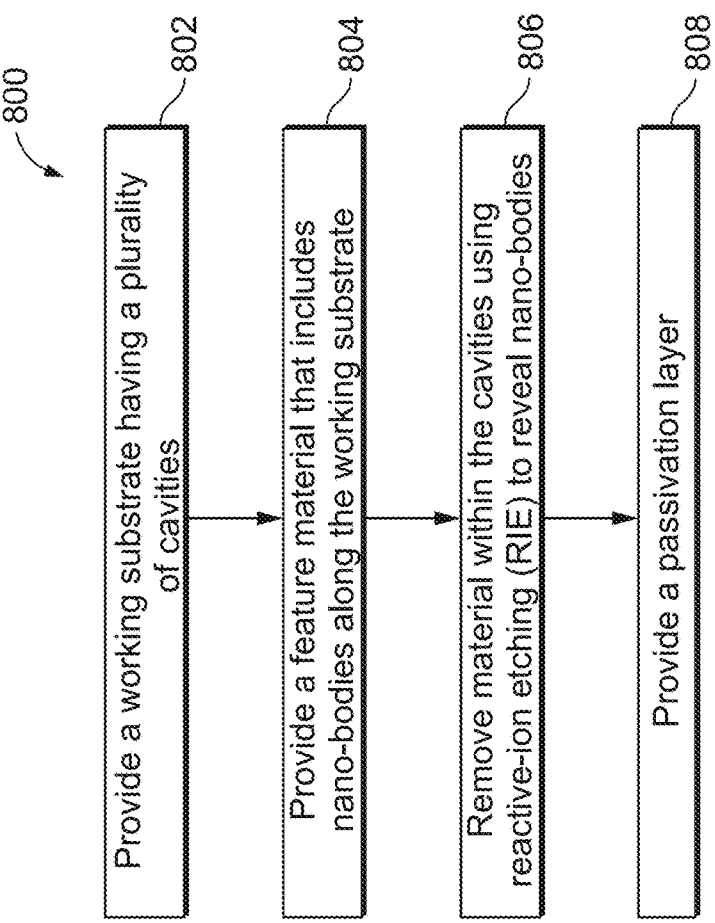
FIG. 28 is a flow chart illustrating a method of manufacturing a structured substrate in accordance with an embodiment.

FIG. 28 is a flowchart showing a method 800 of manufacturing or fabricating a structured substrate. The method 800 may include performing one or more additive or subtractive techniques, such as those described above. The method 800 is illustrated with respect to FIG. 29. The method 800 include providing, at 802, a working substrate 812 having a plurality of cavities or recesses 813 separated by interstitial regions 815. The working substrate 812 may be formed using one or more processes described herein. For example, the working substrate 812 may include fused silica, although other materials may be used. As another example, the working substrate 812 may be formed through an NIL process. At 804, a coating material 814 may be provided onto the working substrate 812. The coating material 814 may include a resin or other viscous material 816 (e.g., high viscosity hydrogel) having nanoparticles 818 dispersed therein. The nanoparticles 818 may include gold particles or other plasmon resonant material particles. In particular embodiments, the coating material 814 may be spin coated onto the working substrate 812 such that the coating material 814 exists within the cavities 813 and along the interstitial regions 815. The providing, at 804, may also include thermally annealing (e.g., baking) the coating material 814 onto the working substrate 812.

At 806, the coating material 814 may be selectively etched to remove the formerly viscous material 816 and reveal the nanoparticles 818. Optionally, the method may include removing nanoparticles 818 from the interstitial regions 815. For example, the working substrate 812 may be polished. At 808, a passivation layer 820 may be applied over the nanoparticles 818 and the interstitial regions 815. For example, $Ta_2O_5$ may be sputtered onto the nanoparticles 818 and the interstitial regions 815. Accordingly, a structured substrate 822 may be provided that includes a plurality of cavities 813 that each have a plurality of nanoparticles 818 therein. The nanoparticles 818 may be relatively dispersed within the cavities 813 such that two or more of the plurality of nanoparticles 818 are separated by a distance that is suitable for amplifying light emissions and/or excitation light.

Figure 30:
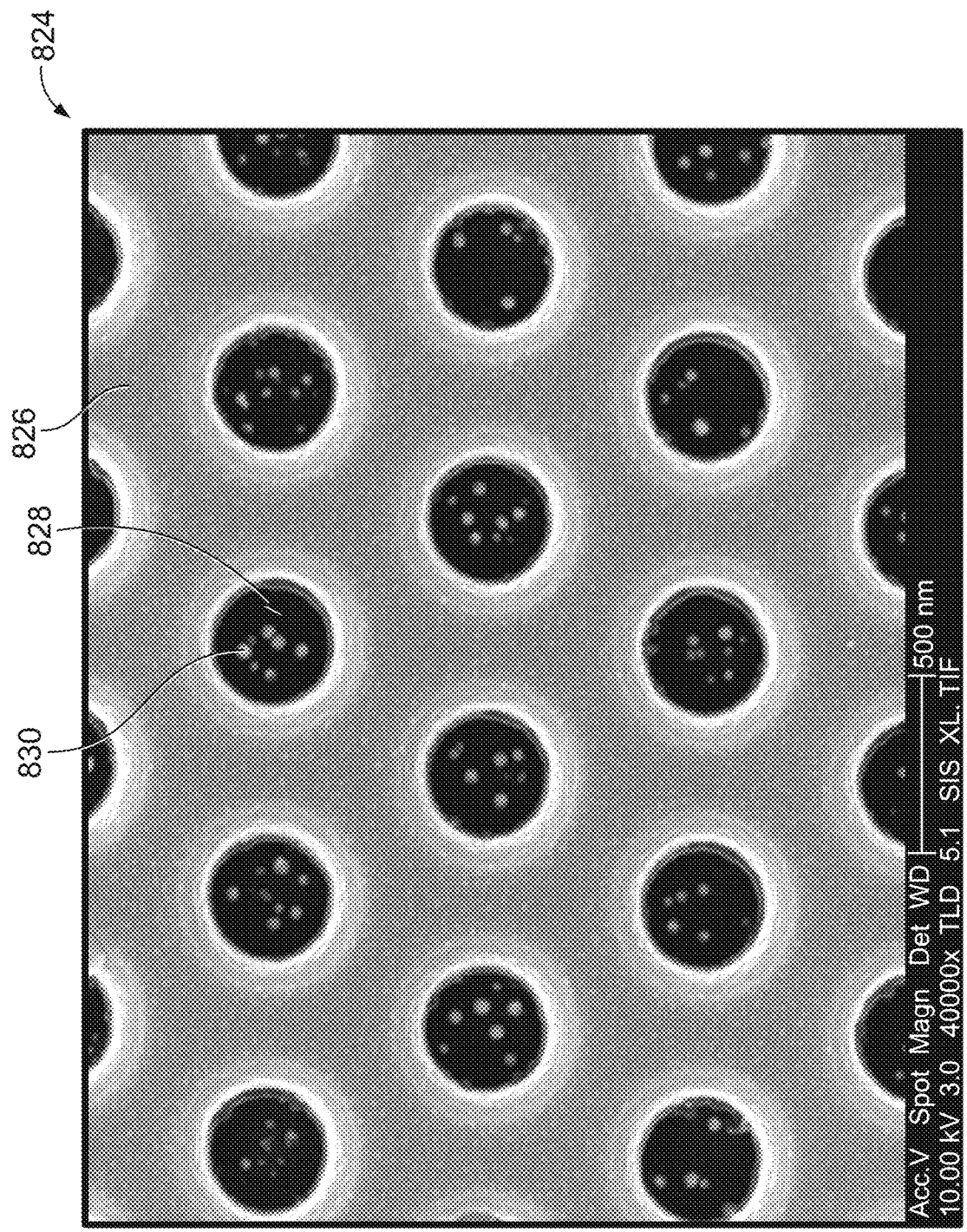
FIG. 30 is an SEM image of a working substrate that was formed using a method similar to the method of FIG. 28.

FIG. 30 is an SEM image of a structured substrate 824 that was formed in accordance with the method 800. As shown, the structured substrate 824 includes a base layer or working substrate 826 having a plurality of cavities 828. Each of the cavities 828 includes a plurality of nanoparticles 830 deposited therein.

Figure 31:
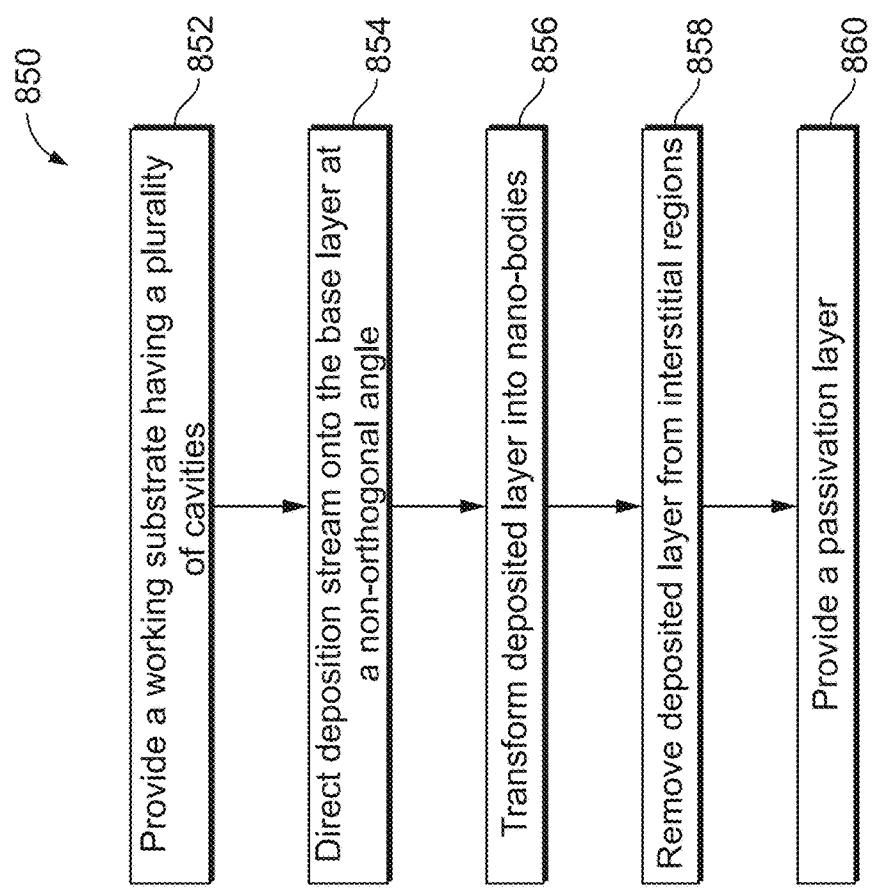
FIG. 31 is a flow chart illustrating a method of manufacturing a structured substrate in accordance with an embodiment.

FIG. 31 is a flowchart illustrating a method 850 of manufacturing or fabricating a structured substrate. The method 850 is illustrated with respect to FIG. 32. The method 850 may include performing one or more additive or subtractive techniques, such as those described above. In some embodiments, the method 850 includes steps that are similar or identical to the steps of the method 500 (FIG. 11) or one of the other methods described herein. The method 850 includes providing, at 852, a working substrate 862 having an operative side 864. The working substrate 862 may be similar to one or more of the working substrates and/or other working substrates described herein. For example, the working substrate 862 may include one or more structures (e.g., layers, features, and the like) that have been provided using the additive and subtractive techniques described above.

The operative side 864 has a non-planar contour that includes a side surface 866 and an array of receiving cavities 868 that open to the side surface 866. In the illustrated embodiment, the side surface 866 is planar between the receiving cavities 868. The method 850 may include directing, at 854, a deposition stream 870 onto the operative side 864 of the working substrate 862. The deposition stream 870 is directed at a non-orthogonal angle with respect to the operative side 864. The deposition stream 870 may be provided by a deposition source (not shown). The deposition stream 870 includes a feature material 872, such as a plasmon resonant material. In particular embodiments, the deposition stream 872 is provided in a substantially linear manner (e.g., in one direction along an axis). As such, the directing operation at 854 may be characterized as line-of-sight deposition. For example, the deposition source may be an electron beam evaporation system. However, it is contemplated that other line-of-sight deposition sources may be used.

Figure 32:
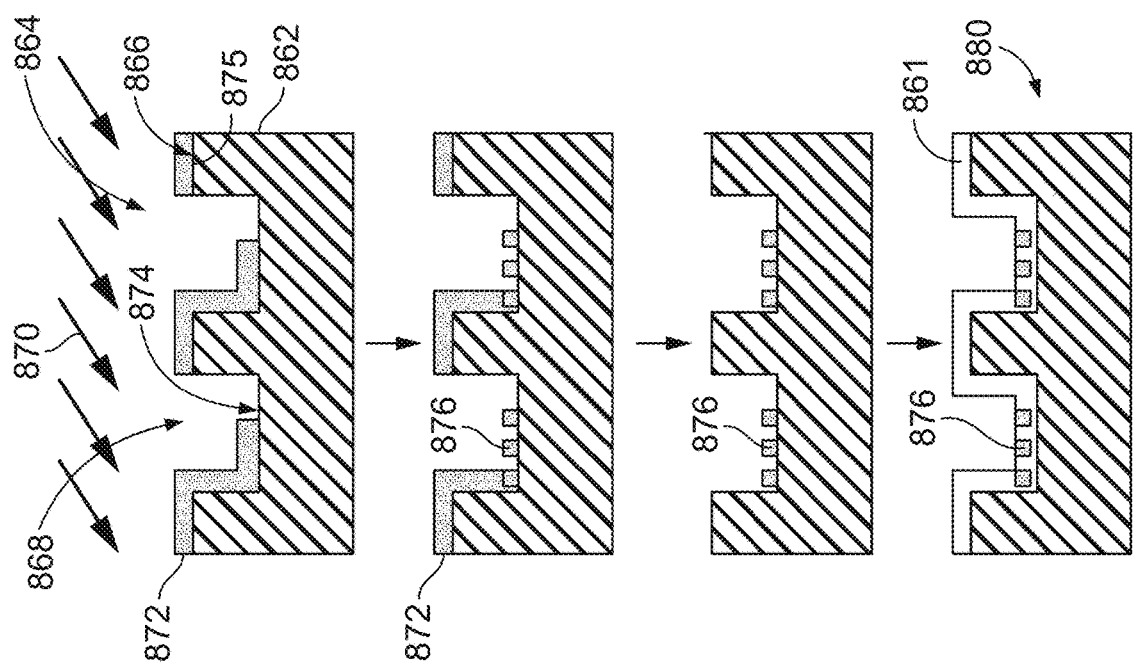
FIG. 32 is a side view illustrating different steps of the method shown in FIG. 31.

The receiving cavities 868 include bottom surfaces 874. The feature material 872 is deposited along the bottom surfaces 874 and surfaces of the interstitial regions 875. However, due to the non-orthogonal angle of the directed deposition and the shadow effect, the feature material 872 in each receiving cavity 868 may be localized closer to one end or side of the receiving cavity 868 as shown in FIG. 32.

After directing, at 854, a deposition stream at a non-orthogonal angle onto the working substrate 862, the method 850 may include transforming, at 856, the deposited layer of the feature material 872 into nanoparticles 876. For example, the deposited layer of the feature material 872 may be thermally annealed or reflowed to transform the layer into nanoparticles 876. During thermal annealing, the deposited layer may be heated (e.g., 400° C.) such that the deposited layer coalesces into discrete nanoparticles. The nanoparticle size can be a function of the starting thickness of the deposited layer.

Optionally, at 858, the deposited layer may be removed from the interstitial regions 875 and, at 860, a passivation layer 861 (e.g., $Ta_2O_5$) may be sputtered onto the nanoparticles 876 and the working substrate 862. Accordingly, a structured substrate 880 may be provided that includes a plurality of nanoparticles 876 that are grouped together within each of the receiving cavities 868.

Figure 33:
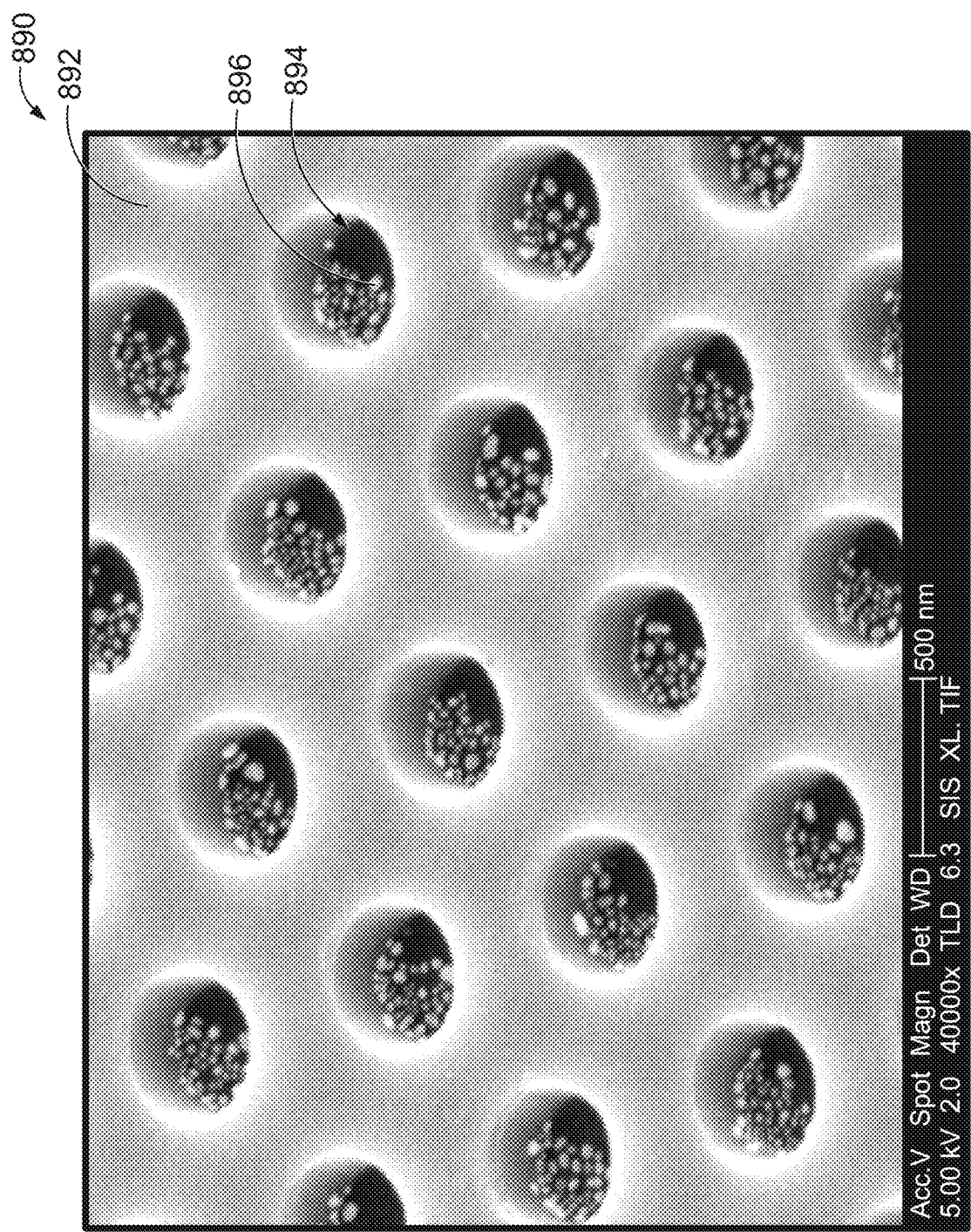
FIG. 33 is an SEM image of a working substrate that was formed using a method similar to the method of FIG. 31.

FIG. 33 is an SEM image of a structured substrate 890 that was formed in accordance with the method 850 (FIG. 31). As shown, the structured substrate 890 includes a working substrate (or cavity layer) 892 having a plurality of cavities

894. Each of the cavities 894 includes a plurality of nanoparticles 896 deposited therein. As shown, the nanoparticles 896 are localized or grouped closer to one side of the receiving cavity 894.

Figure 34:
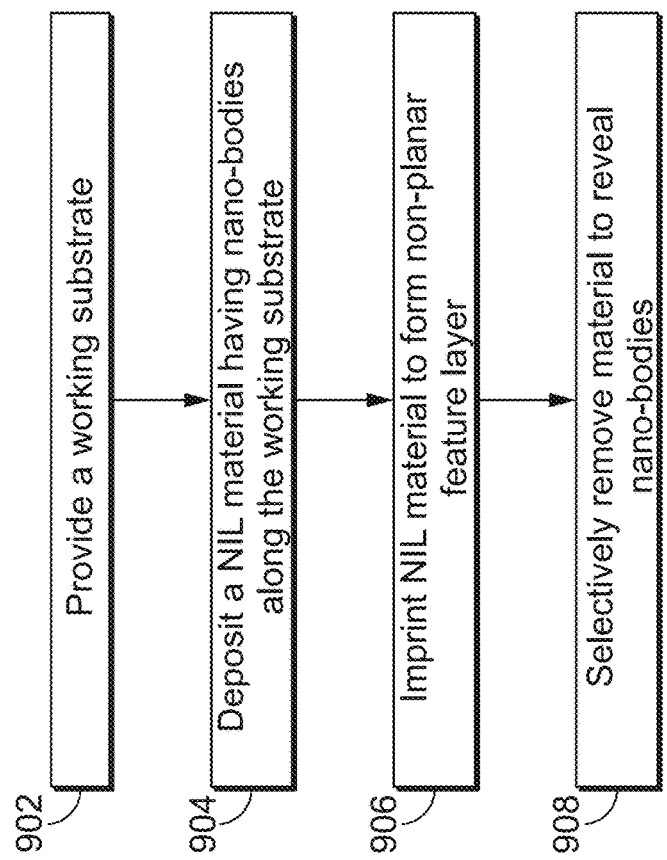
FIG. 34 is a flow chart illustrating a method of manufacturing a structured substrate in accordance with an embodiment.
Figure 37:
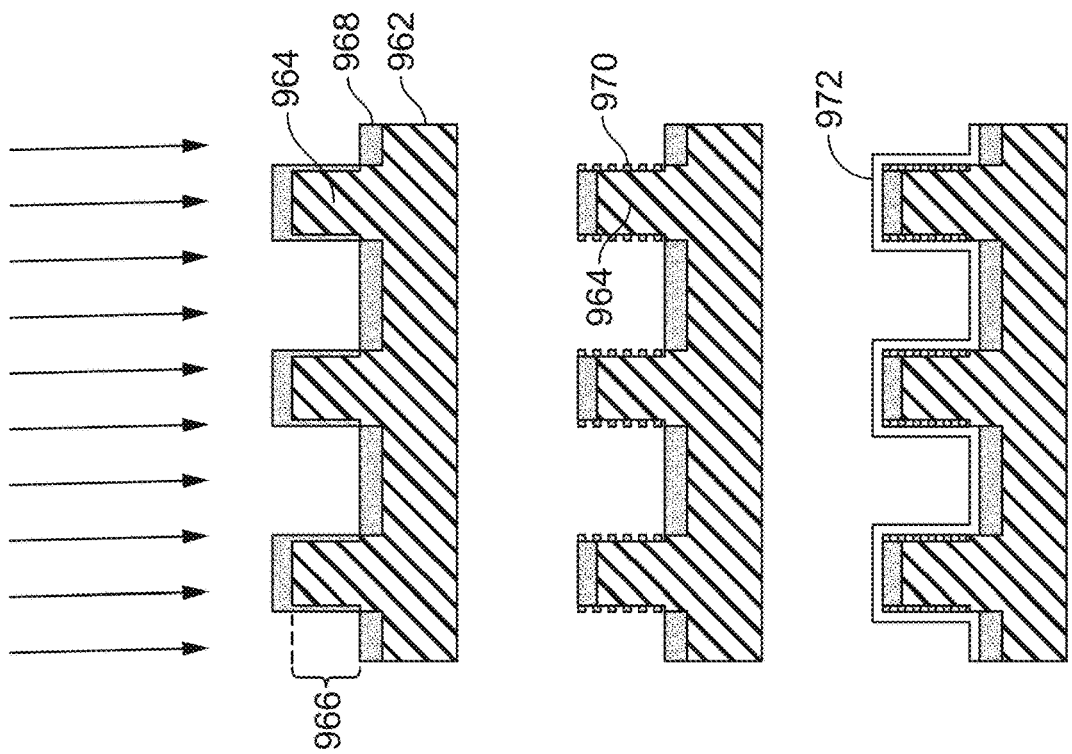
FIG. 37 is a side view illustrating different steps of the method shown in FIG. 36.

FIG. 34 is a flowchart illustrating a method 900 of manufacturing or fabricating a structured substrate. The method 900 is illustrated with respect to FIG. 35. The method 900 may include performing one or more additive or subtractive techniques, such as those described above. For example, the method 900 includes providing, at 902, a working substrate (or base layer) 912 having a substrate side 915. The working substrate 912 may be, for example, a glass wafer or a layer of fused silica. At 904, a NIL material 914 is provided along the substrate side 915 of the working substrate 912. For example, the NIL material 914 may be deposited along the working substrate 912 using a spin coating technique or by depositing a designated pattern of droplets along the substrate side 915. The NIL material 914 may comprise a curable material 917 that is capable of being imprinted using the NIL technique, such as a polymer. The NIL material 914 also includes a plurality of nanoparticles 916 that are dispersed within the curable material 917.

At 906, the NIL material 914 may be imprinted to form a non-planar feature layer 918. For example, a mold (not shown) having a mold side or surface with a predetermined contour may be pressed into the ML material 914 such that the NIL material 914 is sandwiched between the mold and the substrate side 915. The NIL material 914 may then flow into the voids of the mold and take a complementary shape of the mold. The NIL material 914 may then be cured or activated by light, pressure, and/or heat to form the non-planar feature layer 918.

Figure 35:
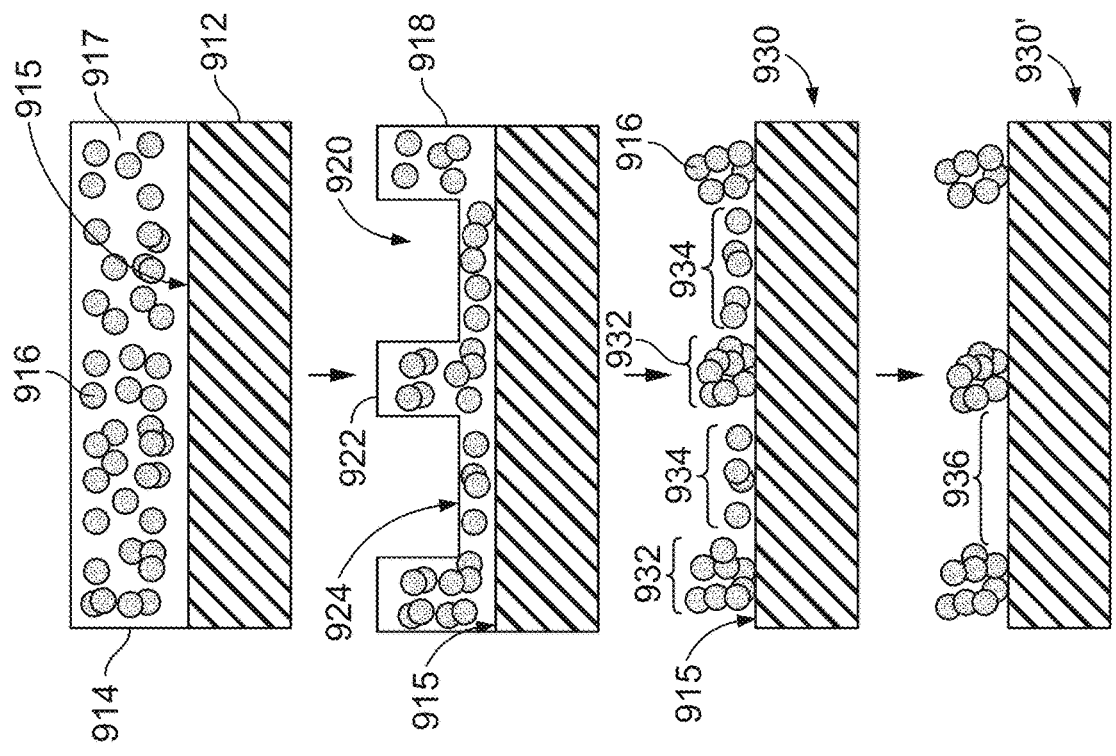
FIG. 35 is a side view illustrating different steps of the method shown in FIG. 34.

The non-planar feature layer 918 includes a plurality of recesses 920 that are separated by interstitial regions 922. In the illustrated embodiment, a portion of the NIL material 914 remains between a bottom surface 924 of the recess 920 and the substrate side 915. In other embodiments, however, the mold may be configured to reduce or minimize the amount of NIL material 914 that exists between the bottom surface 924 and the substrate side 915. As shown in FIG. 35, a greater number of nanoparticles 916 exist within the interstitial regions 922 than the number of nanoparticles 916 that exist within the portion that extends between the bottom surface 924 and the substrate side 915.

At 908, the NIL material 914 may be preferentially or selectively etched to remove the curable material 917 of the NIL material 914. For example, an RIE process may be applied to the feature layer 918 to remove the curable material 917 and reveal or expose the nanoparticles 916 along the substrate side 915. Optionally, a passivation layer (not shown) may be applied onto the working substrate 912 to cover the nanoparticles 916. Accordingly, a structured substrate 930 may be provided.

As shown in FIG. 35, the structured substrate 930 includes dense regions 932 and sparse regions 934. The dense regions 932 include a greater density of the nanoparticles 916 compared to the sparse region 934. The greater density of the nanoparticles 916 is caused by the greater number of nanoparticles 916 that existed within the interstitial regions 922. As such, the locations of the dense regions 932 correlate to the locations of the interstitial regions 922 of the feature layer 918. The sparse regions 934 correspond to the location of the recess 920. The density of the dense regions 932 and/or sparse regions 934 may be based on the contour or shape of the mold (or contour of the feature layer 918) and the density of nanoparticles 916 dispersed within the NIL material 916. In some embodiments, the dense regions 932 may include nanoparticles 916 that are positioned on top of each other to form a three-dimensional structure. Optionally, the sparse regions 934 may be removed through a subsequent etching process to form substantially blank areas 936. The blank areas 936 may separate the dense regions 932 of nanoparticles 916. The dense regions 932 may correspond to reaction sites along the substrate side 915. As described herein, the nanoparticles 916 may form nanostructures and, in some cases, ensemble amplifiers that at least one of amplify electromagnetic energy that propagates into the corresponding reaction site or amplify electromagnetic energy that is generated within the corresponding reaction site.

Figure 36:
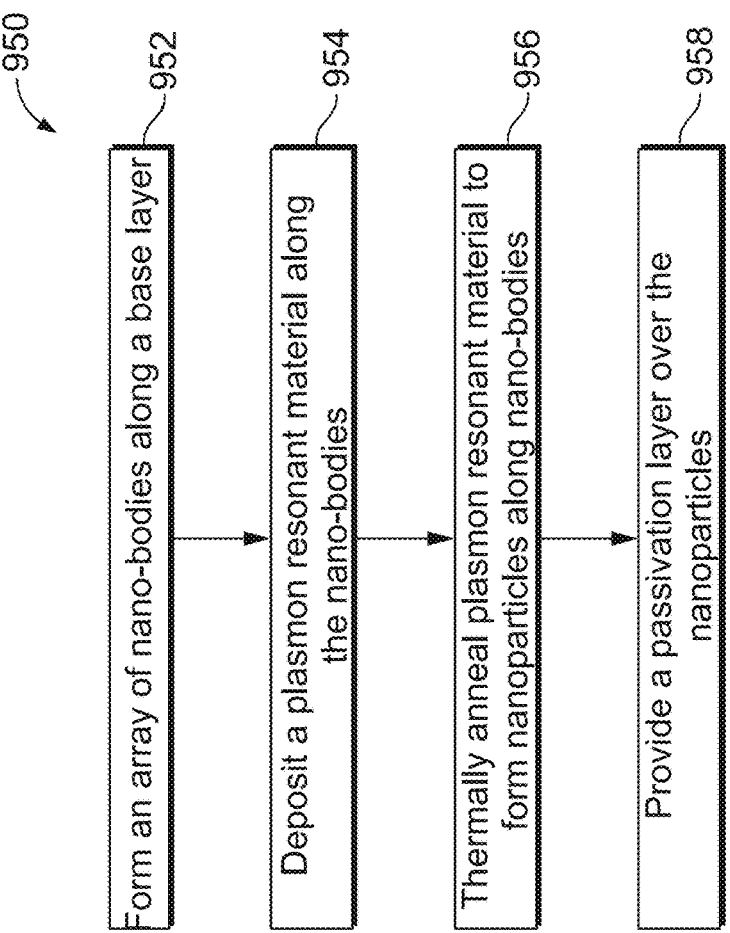
FIG. 36 is a flow chart illustrating a method of manufacturing a structured substrate in accordance with an embodiment.

FIG. 36 is a flowchart showing a method 950 of manufacturing or fabricating a structured substrate. The method 950 is illustrated with respect to FIG. 37. The method 950 may include performing one or more additive or subtractive techniques, such as those described above. For example, the method 950 includes forming, at 952, a plurality of nanobodies 964 along a base layer 962. In an exemplary embodiment, the base layer 962 may comprise a glass wafer or fused silica ($SiO_2$). The base layer 962 may include other sub-layers, such as tantalum oxide, which may be used to form the nanobodies 964. In some embodiments, the nanobodies 964 are formed using photolithographic processes. However, it is contemplated that the nanobodies 964 may be formed using other processes. For example, the nanobodies 964 may be formed using NIL processes, such as those described above. The nanobodies 964 may have a height 966 of, for example, about 100-1000 nm, but other heights may be used. In particular embodiments, the nanobodies 964 are posts that may have a greatest cross-sectional dimension of 100-500 nm. The cross-sections may be, for example, circular or square-shaped.

At 954, a plasmon resonant material 968 (e.g., gold (Au)) may be deposited along the base layer 962 and nanobodies 964. For instance, the plasmon resonant material may be directionally deposited using electron beam evaporation. The plasmon resonant material forms a plasmon resonant layer 968 having a designated thickness. The thickness may be, for example, between 10 and 200 nm or, more particularly, between about 50 and 150 nm. However, other thicknesses may be used. At 956, the working substrate may be subjected to a thermal annealing process to transform the plasmon resonant layer 968 into nanoparticles 970 along the nanobodies 964. For example, the working substrate may be heated to 500° C. for about 10 minutes. At 958, a passivation layer 972 (e.g., $Ta_2O_5$) may be applied. The passivation layer 972 may be applied, for example, through a sputter coating process. In some embodiments, the method 950 may also include providing another layer over the passivation layer and, optionally, forming recesses or cavity from the added layer.

Figure 39:
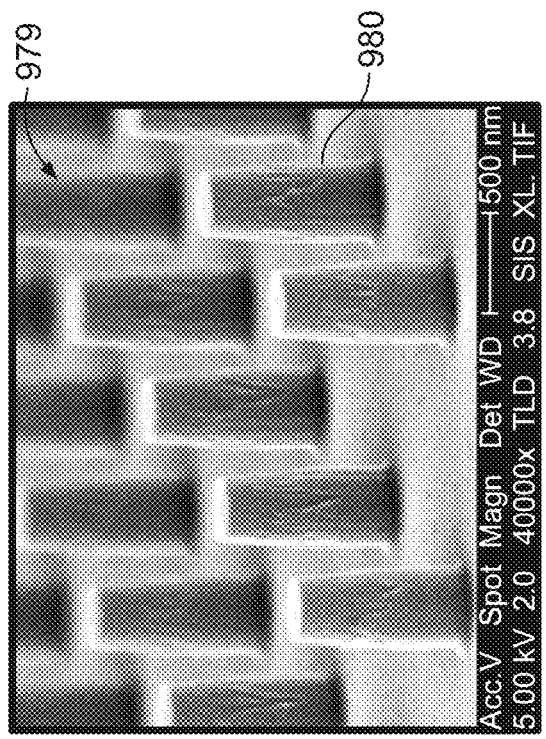
FIG. 39 is an enlarged SEM image of a working substrate that was formed using a method similar to the method of FIG. 36.
Figure 41:
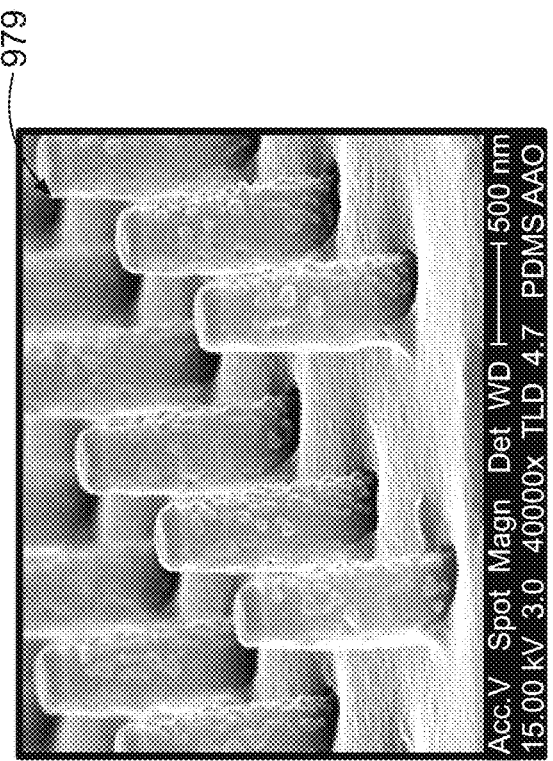
FIG. 41 is an enlarged SEM image of a working substrate that was formed using a method similar to the method of FIG. 36 after a plasmon resonant material has been provided.
Figure 38:
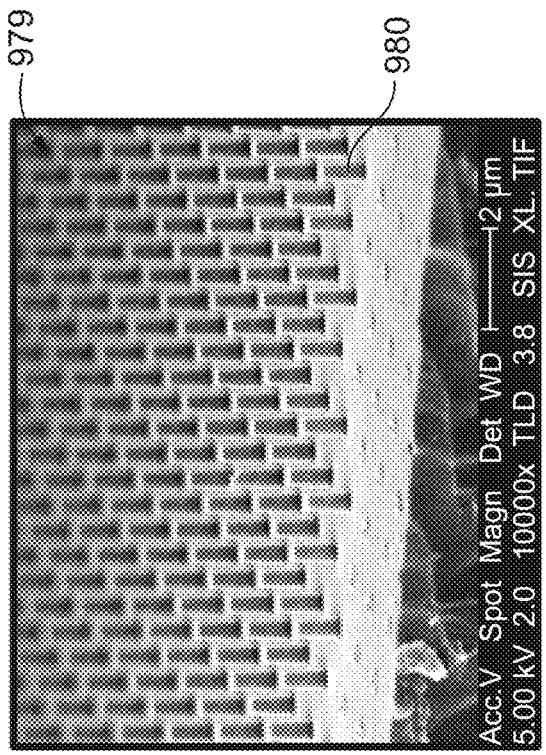
FIG. 38 is an SEM image of a working substrate that was formed using a method similar to the method of FIG. 36.
Figure 40:
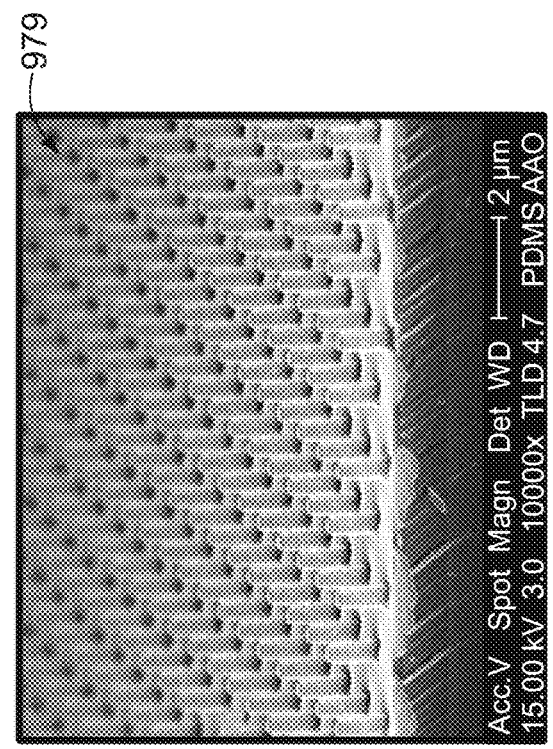
FIG. 40 is an SEM image of a working substrate that was formed using a method similar to the method of FIG. 36 after a plasmon resonant material has been provided.

FIG. 38 illustrates a first SEM image of an array 979 of nanoposts 980 that were formed using a method similar to the method 950. FIG. 39 is a second SEM image of the array 979 of nanoposts 980 at a greater magnification than the magnification of FIG. 38. The nanoposts 980 are formed from fused silica. The nanoposts 980 are cylindrical and have a height of about 800 nm and a diameter of about 350 nm. FIG. 40 illustrates a first SEM image of the array 979 after 100 nm of gold (Au) was directionally deposited onto the nanoposts 980 and thermally annealed for about 10 minutes at 500° C. FIG. 41 is a second SEM image of the array 979 after thermally annealing at a greater magnification than the magnification of FIG. 40.

In some cases, the process that was used to apply a layer to the working substrate may provide identifiable structural characteristic(s) to that layer that is/are distinct from structural characteristic(s) of other layers provided by other processes. More specifically, it may be possible to identify how a layer was manufactured. For example, a portion of a substrate may be examined using a scanning electron microscope (SEM) to identify how one or more layers of the substrate were manufactured.

Figure 42:
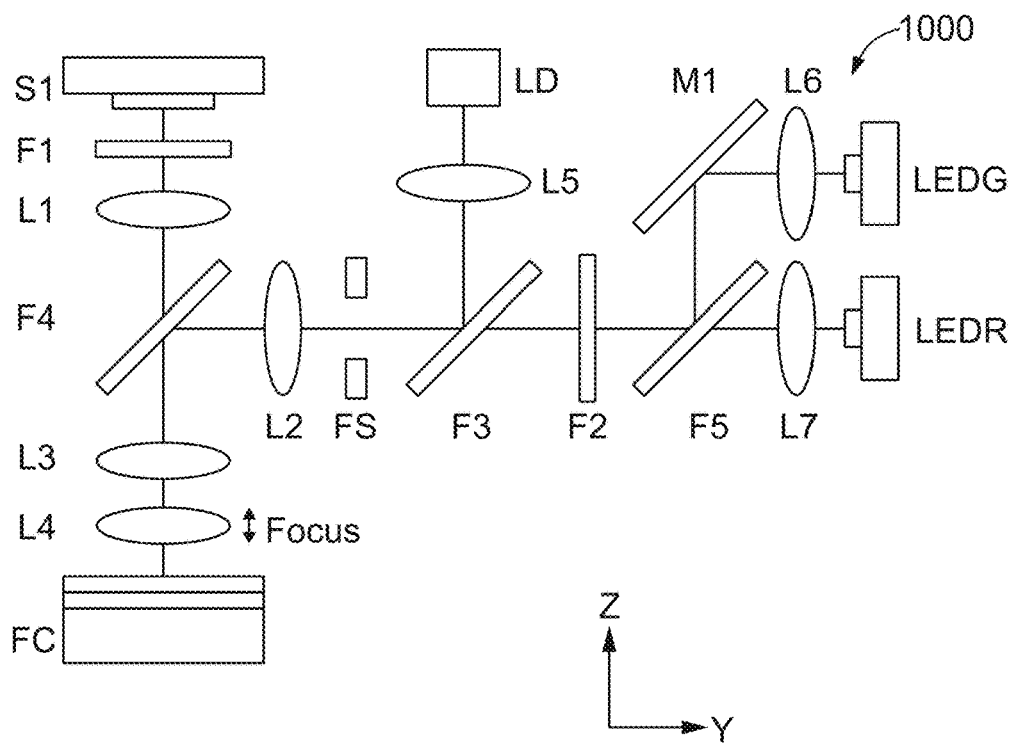
FIG. 42 is a schematic diagram of an imaging system formed in accordance with an embodiment.

FIG. 42 shows a schematic view of an exemplary imaging device or system 1000, which may also be referred to as a microfluorometer, for purposes of demonstrating functional arrangement for at least some optical components. The imaging device 1000 may detect light emissions (e.g., fluorescent light emissions) from a structured substrate, such as the structured substrates described herein. Two excitation sources are shown, including a green LED (LEDG) and a red LED (LEDR). Excitation light from each passes through a green LED collector lens (L6) and red LED collector lens (L7), respectively. An LED fold mirror (M1) reflects the green excitation radiation to a combiner dichroic (F5) which reflects the green excitation radiation through an excitation filter (F2), then through a laser diode beam splitter (F3), then through an excitation field stop (FS), then through an excitation projection lens group L2 to an excitation/emission dichroic (F4) which reflects the green excitation radiation through a stationary objective lens group (L3) and a translating objective lens group (L4) to the surface of a flow cell (FC). The red excitation radiation passes from the red LED collector lens (L7) to the combiner dichroic (F5) after which the red excitation radiation follows the same path as the green excitation radiation to the surface of the flow cell (FC). As shown in the figure, focusing is actuated by moving the translating objective lens group (L4) up and down (i.e. along the z dimension). Emission from the flow cell (FC) surface passes back through the translating objective lens group (L4), and then through the stationary objective lens group (L3) to the excitation/emission dichroic (F4) which passes the emission radiation to the emission projection les group (L1) through to the emission filter and then to the CMOS image sensor (Si). A laser diode (LD) is also directed via a laser diode coupling lens group (L5) to the laser diode beam splitter (F3) which reflects the laser diode radiation through the excitation field stop (FS), the excitation projection lens group (L2), the excitation/emission dichroic (F4), the stationary objective lens group (L3) and the translating objective lens group (L4) to the flow cell (FC).

As demonstrated by the exemplary embodiment of FIG. 42, the imaging device 1000 can include a beam splitter and a detector, wherein the beam splitter is positioned to direct excitation radiation from an excitation radiation source to the objective lens and to direct emission radiation from the objective to the detector. The imaging device 1000 can optionally include an excitation radiation source such as an LED.

It will be understood that the particular components shown in the figures are exemplary and can be replaced with components of similar function. For example, any of a variety of radiation sources can be used instead of an LED. Particularly useful radiation sources are arc lamps, lasers, semiconductor light sources (SLSs), or laser diodes. LEDs can be purchased, for example, from Luminus (Billerica, Mass.). Similarly, a variety of detectors are useful including, but not limited to a charge-coupled device (CCD) sensor; photomultiplier tubes (PMT's); or complementary metal-oxide-semiconductor (CMOS) sensor. A particularly useful detector is a 5-megapixel CMOS sensor (MT9P031) available from Aptina Imaging (San Jose, Calif).

FIG. 42 provides exemplary embodiments of an imaging device 1000 that includes two excitation sources. This configuration is useful for detecting at least two fluorophores that are excited at different wavelengths, respectively. If desired, the imaging device 1000 can be configured to include more than two excitation sources. For example, the imaging device 1000 can include at least 2, 3, 4 or more different excitation sources (i.e. sources producing different wavelengths from each other). Alternatively or additionally, beam splitters and optical filters can be used to expand the range of excitation wavelengths available from an individual radiation source.

Figure 43:
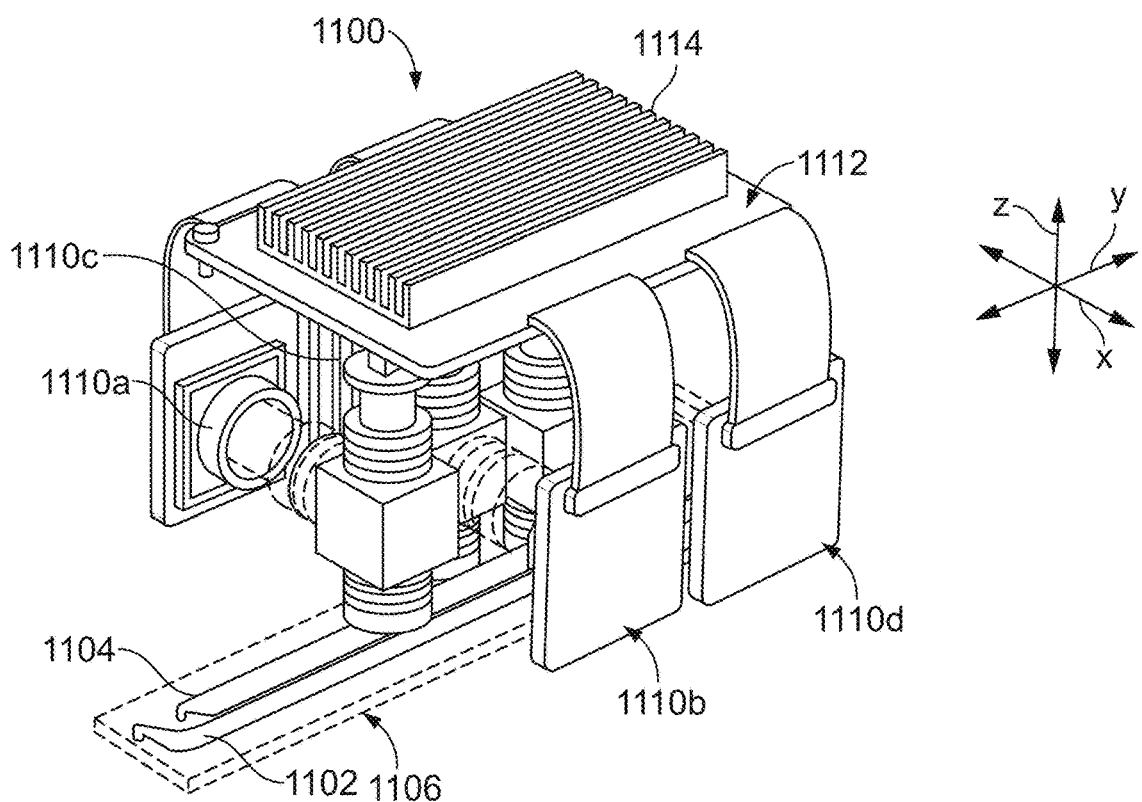
FIG. 43 is a perspective view of a read head including a plurality of microfluorometers formed in accordance with an embodiment.

FIG. 43 shows an exemplary arrangement of four imaging devices (referred to as microfluorometers) in a single read head or carriage 1100. The four microfluorometers are arranged in a staggered layout with respect to first and second channels 1102 and 1104 of a flow cell 1106. In the arrangement shown, two of the microfluorometers (corresponding to detectors 1110A and 1110C) are configured to image separate regions of the first channel 1102 and the other two microfluorometers (corresponding to detectors 1110B and 1110D) are configured to image separate regions of the second channel 1104. As shown, the microfluorometers (corresponding to detectors 1110A and 1110C) are staggered with respect to the microfluorometers (corresponding to detectors 1110B and 1110D) in the x dimension such that the two pairs of microfluorometers can detect the adjacent first and second channels 1102 and 1104 respectively.

In the exemplary embodiment shown in FIG. 43 the four radiation sources are in thermal contact with a single large heat sink 1114. A single large heat sink provides a greater degree of heat dissipation than many configurations that use an individual heat sink for each radiation source. However, if desired individual radiation sources can be thermally coupled to individual heat sinks. An advantage of the arrangement of microfluorometers shown in FIG. 43 is the provision of a compact read head. Similar advantages can be derived for embodiments where the relative positions of the excitation source and detector in each microfluorometer are exchanged.

A microfluorometer, or read head having several microfluorometers, can be positioned above a flow cell (with respect to gravity's arrow) as exemplified for several embodiments set forth herein. However, it is also possible to position a microfluorometer, or a read head, underneath a flow cell. Accordingly a flow cell can be transparent on the top side, bottom side or both sides with respect to the wavelengths of excitation and emission radiation used. Indeed, in some embodiments it may be desirable to position microfluorometers on both sides of a flow cell or to position read heads on both sides of a flow cell. Other orientations with respect to gravity are also possible, including for example a side to side orientation between a flow cell and microfluorometer (or read head).

A microfluorometer or read head can be configured to detect the two opposing, inner surfaces of a flow cell from a single side of the flow cell. For example, the microfluorometer or read head can employ an optical compensator that is inserted and removed to detect alternative surfaces of the flow cell. Exemplary methods and apparatus for detecting opposing inner surfaces of a flow cell such as the use of optical compensators are described in U.S. Pat. No. 8,039,817, which is incorporated herein by reference in its entirety.

A compensator is optional, for example, depending upon the NA and/or optical resolution of the apparatus.

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Solid supports can optionally be inert to a chemistry that is used to modify a gel. For example, a solid support can be inert to chemistry used to attach analytes, such as nucleic acids, to gels in a method set forth herein. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers.

Particular embodiments of the methods and compositions presented herein utilize a solid support having a patterned or structured substrate. The patterned or structured substrate can comprise a patterned gel array, as described in U.S. Ser. No. 13/787,396, the entire content of which is incorporated herein by reference. In particular embodiments, a structured substrate can be made by patterning a solid support material with wells (e.g. microwells or nanowells), coating the patterned support with a gel material (e.g. PAZAM, SFA or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids can be attached to gel material. A solution of target nucleic acids (e.g. a fragmented human genome) can then be contacted with the polished substrate such that individual target nucleic acids will seed individual wells via interactions with primers attached to the gel material; however, the target nucleic acids will not occupy the interstitial regions due to absence or inactivity of the gel material. Amplification of the target nucleic acids will be confined to the wells since absence or inactivity of gel in the interstitial regions prevents outward migration of the growing nucleic acid colony. The process is conveniently manufacturable, being scalable and utilizing conventional micro- or nano-fabrication methods.

A solid support used in a structured substrate set forth herein can be made from any of a variety of materials set forth herein, for example, above in the definitions, below in the examples or immediately following. A particularly useful material is glass. Other suitable substrate materials may include polymeric materials, plastics, silicon, quartz (fused silica), borofloat glass, silica, silica-based materials, carbon, metals, an optical fiber or optical fiber bundles, sapphire, or plastic materials such as COCs and epoxies. The particular material can be selected based on properties desired for a particular use. For example, materials that are transparent to a desired wavelength of radiation are useful for analytical techniques that will utilize radiation of the desired wavelength, such as one or more of the techniques set forth herein. Conversely, it may be desirable to select a material that does not pass radiation of a certain wavelength (e.g. being opaque, absorptive, or reflective). This can be useful for formation of a mask to be used during manufacture of the structured substrate, such as a method set forth herein; or to be used for a chemical reaction or analytical detection carried out using the structured substrate, such as those set forth herein. Other properties of a material that can be exploited are inertness or reactivity to certain reagents used in a downstream process, such as those set forth herein; or ease of manipulation or low cost during a manufacturing process manufacture, such as those set forth herein. Further examples of materials that can be used in the structured substrates or methods of the present disclosure are described in U.S. Ser. No. 13/661,524 and US Pat. App. Pub. No. 2012/0316086 A1, each of which is incorporated herein by reference.

Particularly useful solid supports for some embodiments are located within a flow cell apparatus. Exemplary flow cells, methods for their manufacture and methods for their use are described in US Pat. App. Publ. Nos. 2010/0111768 A1 or 2012-0270305 A1; or WO 05/065814, each of which is incorporated herein by reference. Flow cells provide a convenient format for housing an array that is produced by the methods of the present disclosure and that is subjected to a sequencing-by-synthesis (SBS) or other technique that involves repeated delivery of reagents in cycles (e.g. synthesis techniques or detection techniques having repetitive or cyclic steps). Exemplary detection methods are set forth in further detail below.

In some embodiments a flow-cell or other vessel having multiple surfaces is used. Vessels having multiple surfaces can be used such that only a single surface has gel-containing concave features (e.g. wells). Alternatively two or more surfaces present in the vessel can have gel-containing concave features. One or more surfaces of a flow cell can be selectively detected. For example, opposing surfaces in the interior of a flow cell can be selectively addressed with focused radiation using methods known in the art such as confocal techniques. Useful confocal techniques and devices for selectively directing radiation to multiple surfaces of a vessel (e.g. a flow cell) are described, for example, in US Pat. App. Pub. No. 2009/0272914 A1 or U.S. Pat. No. 8,039,817, each of which is incorporated herein by reference.

In many embodiments, the interstitial region can be substantially devoid of nanostructures by polishing the solid support, for example via chemical or mechanical polishing, thereby retaining nanostructures in the wells but removing or inactivating substantially all of the nanostructures from the interstitial regions on the surface of the structured substrate between the wells. Mechanical polishing can be carried out by applying abrasive forces to the surface of the solid support. Exemplary methods include abrasion with a slurry of beads, wiping with a sheet or cloth, scraping or the like. It will be understood that beads used for polishing or other uses set forth herein can be, but need not be, spherical. Rather beads can have irregular shapes, polygonal shapes, ovoid shapes, elongated shapes, cylindrical shapes etc. The surface of the beads can be smooth or rough. Any of a variety of particles can be useful as beads for the methods and compositions set forth herein. One example of polishing includes using a lintless (cleanroom grade) wipe coated with a 3 μm silica bead slurry (10% w/v in water) to remove interstitial nanostructures. A polishing wheel/grinder can also be used with this slurry. Mechanical polishing can also be achieved using a fluid jet or gas (e.g. air or inert gas such as Argon or Nitrogen) jet to remove gel from interstitial regions.

As used herein, the term "library," when used in reference to analytes, refers to a collection of analytes having different chemical compositions. Typically, the analytes in a library will be different species having a common feature or characteristic of a genera or class, but otherwise differing in some way. For example, a library can include nucleic acid species that differ in nucleotide sequence, but that are similar with respect to having a sugar-phosphate backbone.

As used herein, the terms "nucleic acid" and "nucleotide" are intended to be consistent with their use in the art and to include naturally occurring species or functional analogs thereof. Particularly useful functional analogs of nucleic acids are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid or nucleotide are known in the art. The terms "probe" or "target," when used in reference to a nucleic acid, are intended as semantic identifiers for the nucleic acid in the context of a method or composition set forth herein and does not necessarily limit the structure or function of the nucleic acid beyond what is otherwise explicitly indicated. The terms "probe" and "target" can be similarly applied to other analytes such as proteins, small molecules, cells or the like.

As used herein, the terms "coat" and "coating" and like terms, when used as a verb, are intended to mean providing a layer or covering on a surface. At least a portion of the surface can be provided with a layer or cover. In some cases the entire surface can be provided with a layer or cover. In alternative cases only a portion of the surface will be provided with a layer or covering. The term "coat," when used to describe the relationship between a surface and a material, is intended to mean that the material is present as a layer or cover on the surface. The material can seal the surface, for example, preventing contact of liquid or gas with the surface. However, the material need not form a seal. For example, the material can be porous to liquid, gas, or one or more components carried in a liquid or gas. Exemplary materials that can coat a surface include, but are not limited to, a gel, polymer, organic polymer, liquid, metal, a second surface, plastic, silica, or gas.

Structured substrates of the present disclosure that contain nucleic acid arrays can be used for any of a variety of purposes. A particularly desirable use for the nucleic acids is to serve as capture probes that hybridize to target nucleic acids having complementary sequences. The target nucleic acids once hybridized to the capture probes can be detected, for example, via a label recruited to the capture probe. Methods for detection of target nucleic acids via hybridization to capture probes are known in the art and include, for example, those described in U.S. Pat. Nos. 7,582,420; 6,890,741; 6,913,884 or 6,355,431 or US Pat. App. Pub. Nos. 2005/0053980 A1; 2009/0186349 A1 or 2005/0181440 A1, each of which is incorporated herein by reference. For example, a label can be recruited to a capture probe by virtue of hybridization of the capture probe to a target probe that bears the label. In another example, a label can be recruited to a capture probe by hybridizing a target probe to the capture probe such that the capture probe can be extended by ligation to a labeled oligonucleotide (e.g. via ligase activity) or by addition of a labeled nucleotide (e.g. via polymerase activity).

A nucleic acid array can also be used in a sequencing procedure, such as a sequencing-by-synthesis (SBS) technique. Briefly, SBS can be initiated by contacting the target nucleic acids with one or more labeled nucleotides, DNA polymerase, etc. Those features where a primer is extended using the target nucleic acid as template will incorporate a labeled nucleotide that can be detected. Optionally, the labeled nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., *Nature* 456:53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210, 891; 6,258,568 and 6,274,320, each of which is incorporated herein by reference). In pyrosequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to arrays of the present disclosure are described, for example, in WIPO Pat. App. Ser. No. PCT/US11/57111, US Pat. App. Pub. No. 2005/0191698 A1, U.S. Pat. Nos. 7,595,883, and 7,244,559, each of which is incorporated herein by reference.

Sequencing-by-ligation reactions are also useful including, for example, those described in Shendure et al. *Science* 309:1728-1732 (2005); U.S. Pat. Nos. 5,599,675; and 5,750, 341, each of which is incorporated herein by reference. Some embodiments can include sequencing-by-hybridization procedures as described, for example, in Bains et al., *Journal of Theoretical Biology* 135(3), 303-7 (1988); Drmanac et al., *Nature Biotechnology* 16, 54-58 (1998);

Fodor et al., *Science* 251(4995), 767-773 (1995); and WO 1989/10977, each of which is incorporated herein by reference. In both sequencing-by-ligation and sequencing-by-hybridization procedures, nucleic acids that are present in gel-containing wells (or other concave features) are subjected to repeated cycles of oligonucleotide delivery and detection. Fluidic systems for SBS methods as set forth herein, or in references cited herein, can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides. Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference.

Another useful application for an array of the present disclosure is gene expression analysis. Gene expression can be detected or quantified using RNA sequencing techniques, such as those, referred to as digital RNA sequencing. RNA sequencing techniques can be carried out using sequencing methodologies known in the art such as those set forth above. Gene expression can also be detected or quantified using hybridization techniques carried out by direct hybridization to an array or using a multiplex assay, the products of which are detected on an array. An array of the present disclosure can also be used to determine genotypes for a genomic DNA sample from one or more individual. Exemplary methods for array-based expression and genotyping analysis that can be carried out on an array of the present disclosure are described in U.S. Pat. Nos. 7,582,420; 6,890,741; 6,913,884 or 6,355,431 or US Pat. App. Pub. Nos. 2005/0053980 A1; 2009/0186349 A1 or 2005/0181440 A1, each of which is incorporated herein by reference.

Several applications for arrays of the present disclosure have been exemplified above in the context of ensemble detection, wherein multiple copies of a target nucleic acid are present at each feature and are detected together. In alternative embodiments, a single nucleic acid, whether a target nucleic acid or amplicon thereof, can be detected at each feature. For example, a gel-containing well (or other concave feature) can be configured to contain a single nucleic acid molecule having a target nucleotide sequence that is to be detected. Any of a variety of single molecule detection techniques can be used including, for example, modifications of the ensemble detection techniques set forth above to detect the sites at increased resolution or using more sensitive labels. Other examples of single molecule detection methods that can be used are set forth in US Pat. App. Pub. No. 2011/0312529 A1; U.S. Ser. No. 61/578,684; and U.S. Ser. No. 61/540,714, each of which is incorporated herein by reference.

As used herein, the term "well" refers to a discrete concave feature in a solid support having a surface opening that is completely surrounded by interstitial region(s) of the surface. Wells can have any of a variety of shapes at their opening in a surface including but not limited to round, elliptical, square, polygonal, star shaped (with any number of vertices) etc. The cross section of a well taken orthogonally with the surface can be curved, square, polygonal, hyperbolic, conical, angular, etc.

As used herein, the term "concave feature," when used in reference to a solid support, refers to a recess or indentation in the solid support. Exemplary concave features include, but are not limited to, a well, pit, hole, depression, channel, or trough. A concave feature can optionally have a curved cross section (in the dimension orthogonal to the surface of the solid support); however, a cross section with one or more linear sections, angles or corners is also possible. Cross sections with combinations of curved and linear sections are also possible. Generally, a concave feature need not pass completely through the solid support, for example, instead having a bottom surface or point in the substrate.

The embodiments set forth below and recited in the claims can be understood in view of the above definitions.

For example, in an embodiment, a structured substrate is provided that includes a substrate body having an active side. The substrate body includes reaction cavities that open along the active side and interstitial regions that separate the reaction cavities. The structured substrate also includes an ensemble amplifier positioned within each of the reaction cavities. The ensemble amplifier includes a plurality of nanostructures that are configured to at least one of amplify electromagnetic energy that propagates into the corresponding reaction cavity or amplify electromagnetic energy that is generated within the corresponding reaction cavity.

In one or more aspects, the nanostructures for each of the ensemble amplifiers may have a predetermined position relative to the other nanostructures of the corresponding ensemble amplifier. The ensemble amplifiers may have essentially the same arrangement of nanostructures. Optionally, the ensemble amplifiers have a polarized configuration such that a response from the ensemble amplifiers is based on a polarization of the electromagnetic energy, wherein adjacent ensemble amplifiers have different polarized configurations.

In one or more aspects, the reaction cavities may include a first set of reaction cavities and a second set of reaction cavities. The first set of reaction cavities may preferentially respond to a first polarized light over a second polarized light and the second set of reaction cavities may preferentially respond to the second polarized light over the first polarized light.

In one or more aspects, the active side may include a side surface that extends along the interstitial regions. The side surface may be substantially planar.

In one or more aspects, an organic material may be disposed within the reaction cavities and cover the nanostructures. The organic material may be configured to immobilize a biomolecule within the corresponding reaction cavity. Optionally, the organic material comprises a gel material. Optionally, the organic material comprises a hydrogel. Optionally, the organic material has a volume that is configured to accommodate only a single analyte such that steric exclusion prevents more than one analyte from being captured or seeding the reaction cavity. Optionally, the organic material is permeable to liquid and is configured to attach to a nucleic acid.

In one or more aspects, the substrate body may include a base layer having the nanostructures projecting therefrom. The substrate body may also include a cavity layer stacked with respect to the base layer. The cavity layer may be shaped to include the reaction cavities. Optionally, the nanostructures extend from the base layer, through a portion of the cavity layer, and into the corresponding reaction cavities.

In one or more aspects, the nanostructures are formed of a plasmon resonant material.

In one or more aspects, the nanostructures comprises at least one of: Gold (Au), Silver (Ag), Tin (Sn) Rhodium (Rh), Ruthenium (Ru), Palladium (Pd), Osmium (Os), Iridium (Ir), Platinum (Pt), Titanium (Ti), Aluminum (Al), Chromium (Cr), Copper (Cu), p-type doped silicon, n-type doped silicon, gallium arsenide, Zinc-Indium-Tin Oxide (ZITO), or Tantalum Oxide.

In one or more aspects, the nanostructures in the ensemble amplifiers may have a material composition, shape, and relative position with respect to other nanostructures of the ensemble amplifier to at least one of amplify the electromagnetic energy that propagates into the corresponding reaction cavity or amplify the electromagnetic energy that is generated within the corresponding reaction cavity.

In one or more aspects, the nanostructures in the ensemble amplifiers have a material composition, shape, and relative position with respect to other nanostructures of the ensemble amplifier to amplify the electromagnetic energy that is generated within the corresponding reaction cavity. Optionally, the electromagnetic energy includes fluorescent light emissions.

In one or more aspects, the nanostructures in the ensemble amplifiers may have a composition, shape, and relative position with respect to other nanostructures of the ensemble amplifier to amplify the electromagnetic energy that propagates into the corresponding reaction cavity.

In one or more aspects, a wavelength of the excitation light or the light emissions is between 300 nanometers (nm) and 750 nm.

In one or more aspects, each of the nanostructures may include a nanobody comprising a nanoimprint-lithography (NIL) material and an external layer that surrounds the nanobody. Optionally, the external layer comprises at least one of: Gold (Au), Silver (Ag), Tin (Sn) Rhodium (Rh), Ruthenium (Ru), Palladium (Pd), Osmium (Os), Iridium (Ir), Platinum (Pt), Titanium (Ti), Aluminum (Al), Chromium (Cr), Copper (Cu), p-type doped silicon, n-type doped silicon, gallium arsenide, Zinc-Indium-Tin Oxide (ZITO), or Tantalum Oxide.

In one or more aspects, a passivation layer may extend over the nanobodies. In one or more aspects, a device cover may be coupled to the substrate body to form a flow channel between the active side of the substrate body and the device cover. The flow channel is configured to direct a flow of liquid therethrough that flows into the reaction cavities.

In one or more aspects, the reaction cavities have corresponding bottom surfaces. The nanostructures may project from the bottom surface of the corresponding reaction cavity toward the active side.

In one or more aspects, each of the reaction cavities may be defined by at least one sidewall that extends between the active side and a bottom surface of the reaction cavity. The nanostructures form at least a portion of the at least one sidewall. Optionally, the nanostructures project from the bottom surface of the corresponding reaction cavity.

In one or more aspects, the interstitial regions may be substantially devoid of the nanostructures. Alternatively, the interstitial regions may have embedded nanostructures.

In one or more aspects, the nanostructures may have a height that extends toward the active side along an elevation axis. The height may be at least 10 nm, 20 nm, 30 nm, 40 nm, 50 nm, 60 nm, 70 nm, 80 nm, 90 nm or 100 nm.

In one or more aspects, the nanostructures may have a height that extends toward the active side along an elevation axis. The nanostructures may have a cross-sectional dimension taken transverse to the elevation axis. The cross-sectional dimension may be at least 10 nm, 20 nm, 30 nm, 40 nm, 50 nm, 60 nm, 70 nm, 80 nm, 90 nm or 100 nm.

In one or more aspects, the nanostructures may have a height that extends toward the active side along an elevation axis. The nanostructures may have a cross-sectional dimension taken transverse to the elevation axis. The cross-sectional dimension may be less than 100 nm, 90 nm, 80 nm, 70 nm, 60 nm, 50 nm, 40 nm, 30 nm, 20 nm or 10 nm. Optionally, the cross-sectional dimension is a diameter. Optionally, the cross-sectional dimension represents the greatest cross-sectional dimension that can be taken through the nanostructure.

In one or more aspects, the nanostructures may include dimers or trimers within the reaction cavities.

In one or more aspects, the ensemble amplifiers may form bowtie nanoantennas. In one or more aspects, the nanostructures comprise nanorods, nanorings, and/or nanoplugs.

In an embodiment, a method of manufacturing a structured substrate is provided. The method may include providing a base layer having a base side and forming nanostructures along the base side of the base layer. The method may also include forming a cavity layer that is stacked above the base side. The cavity layer includes a plurality of reaction cavities in which each reaction cavity includes a plurality of the nanostructures therein. The plurality of nanostructures form an ensemble amplifier of the corresponding reaction cavity that is configured to at least one of amplify electromagnetic energy propagating into the corresponding reaction cavity or amplify electromagnetic energy generated within the corresponding reaction cavity.

Various features of the structured substrate, the nanostructures, and/or the ensemble amplifiers may be similar to those described herein.

In one or more aspects, the method also includes providing an organic material within the reaction cavities such that the organic material covers the nanostructures. The organic material may be configured to immobilize a biomolecule within the corresponding reaction cavity.

Optionally, the method also includes polishing the active side to remove the organic material from interstitial regions.

In one or more aspects, the method also includes mounting a device cover to the substrate body to form a flow channel between the active side of the substrate body and the device cover. The flow channel may be configured to direct a flow of liquid therethrough that flows into the reaction cavities.

In an embodiment, a method of manufacturing a structured substrate is provided. The method includes providing a base layer having a base side and forming nanostructures along the base side of the base layer. The method also includes providing a nanoimprint lithography (NIL) layer over the array of nanostructures and imprinting an array of reaction cavities into the NIL layer. A different sub-array of the nanostructures is positioned under each reaction cavity. Each sub-array of nanostructures may be surrounded by a respective fill region of the NIL layer. The method also includes removing the respective fill regions of the NIL layer to expose the sub-arrays of nanostructures within the corresponding reactions cavities. The sub-array of nanostructures within each reaction cavity forms an ensemble amplifier of the corresponding reaction cavity that is configured to at least one of amplify electromagnetic energy propagating into the corresponding reaction cavity or amplify electromagnetic energy generated within the corresponding reaction cavity.

Various features of the structured substrate, the nanostructures, and/or the ensemble amplifiers may be similar to those described herein.

For example, in one or more aspects, the NIL layer is a top NIL layer, wherein forming the nanostructures includes providing a bottom NIL layer and imprinting the nanostructures.

Various features of the structured substrate, the nanostructures, and/or the ensemble amplifiers may be similar to those described herein.

In one or more aspects, the method also includes providing an organic material within the reaction cavities such that the organic material covers the nanostructures. The organic material may be configured to immobilize a biomolecule within the corresponding reaction cavity.

In one or more aspects, the method also includes polishing the active side to remove the organic material from interstitial regions.

In one or more aspects, the method also includes mounting a device cover to the substrate body to form a flow channel between the active side of the substrate body and the device cover, the flow channel configured to direct a flow of liquid therethrough that flows into the reaction cavities.

In an embodiment, a method of manufacturing a structured substrate is provided. The method includes providing a base layer having a base side and providing a nanoimprint lithography (NIL) layer along the base side. The method also includes imprinting the NIL layer to form a base portion and an array of nanobodies that project from the base portion. The method also includes depositing a plasmon resonant film that covers the nanobodies to form a plurality of nanostructures. Each nanostructure includes a corresponding nanobody and a portion of the plasmon resonant film. The method also includes forming a cavity layer having a plurality of reaction cavities in which each reaction cavity includes a plurality of the nanostructures therein. The plurality of nanostructures form an ensemble amplifier of the corresponding reaction cavity that is configured to at least one of amplify electromagnetic energy propagating into the corresponding reaction cavity or amplify electromagnetic energy generated within the corresponding reaction cavity.

Various features of the structured substrate, the nanostructures, and/or the ensemble amplifiers may be similar to those described herein.

For example, the cavity layer may include a NIL material and wherein the step or operation of forming the cavity layer may include imprinting the NIL material of the cavity layer to form the reaction cavities.

In one or more aspects, the method also includes providing an organic material within the reaction cavities such that the organic material covers the nanostructures. The organic material may be configured to immobilize a biomolecule within the corresponding reaction cavity.

In one or more aspects, the method may also include polishing the active side to remove the organic material from interstitial regions.

In one or more aspects, the method may also include mounting a device cover to the substrate body to form a flow channel between the active side of the substrate body and the device cover. The flow channel may be configured to direct a flow of liquid therethrough that flows into the reaction cavities.

In an embodiment, a method of manufacturing a structured substrate is provided. The method includes providing a working substrate having a side surface and an array of reaction cavities. Each of the reaction cavities has an opening along the side surface and extends a depth from the corresponding opening into the working substrate. The reaction cavities coincide with an array plane. The method may also include directing a deposition stream onto the working substrate at a non-orthogonal angle with respect to the array plane. The deposition stream includes a plasmon resonant material. The working substrate forms a shadow area and an incident area in each reaction cavity relative to a path of the deposition stream such that the plasmon resonant material of the deposition stream is blocked by the side surface from being deposited onto the shadow area and is permitted to pass through the opening and form along the incident area.

In one or more aspects, the reaction cavities are defined by respective side walls and bottom surfaces. The side walls extend away from the side surface toward the respective bottom surface. The incident area may extend along at least a portion of the side wall. The shadow area may extend along at least a portion of the bottom surface.

In one or more aspects, the method also includes forming a structured substrate for analyzing biomolecules that includes the working substrate. The material may be deposited along the incident areas forming at least portions of nanostructures that amplify electromagnetic energy.

In one or more aspects, the non-orthogonal angle is a first non-orthogonal angle, the shadow area is a first shadow area, the deposition stream is a first deposition stream, and the incident area is a first incident area. The method may also include directing a second deposition stream onto the working substrate at a second non-orthogonal angle with respect to the array plane that is different than the first non-orthogonal angle. The working substrate may form a second shadow area and a second incident area in each reaction cavity relative to the path of the deposition stream such that a plasmon resonant material of the second deposition stream is blocked by the side surface from being deposited onto the second shadow area and is permitted to pass through the opening and form along the second incident area.

Optionally, at least a portion of the second incident area overlaps with the first shadow area.

Optionally, the plasmon resonant material of the first and second depositions streams is the same.

Optionally, the plasmon resonant material of the first and second depositions streams is different.

In an embodiment, a method of manufacturing a structured substrate is provided. The method includes (a) providing a working substrate having a side surface and an array of reaction cavities. Each of the reaction cavities has an opening along the side surface and extends a depth from the corresponding opening into the working substrate. The reaction cavities coincide with an array plane. The method also includes (b) positioning the working substrate in a receiving orientation relative to a material source (c) directing a deposition stream from the material source onto the working substrate at a non-orthogonal angle with respect to the array plane. The deposition stream includes a plasmon resonant material, wherein the working substrate forms a shadow area and an incident area in each reaction cavity when in the receiving orientation such that the plasmon resonant material from the deposition stream is blocked by the side surface from being deposited onto the shadow area and is permitted to pass through the opening and form along the incident area.

In one or more aspects, the method includes repeating steps (a)-(c), for at least one series, at a different receiving orientation.

In one or more aspects, the method includes repeating steps (a)-(c), for at least one series, with a different plasmon resonant material.

Optionally, steps (a)-(c) are repeated to form an ensemble amplifier having a plurality of the nanostructures within each of the receiving cavities.

In an embodiment, a method of analyzing biomolecules capable of generating light emissions is provided. The method may include providing a structured substrate having an array of reaction sites. Each of the reaction sites includes a plurality of nanostructures that form an ensemble amplifier that is configured to amplify electromagnetic energy that is incident with the nanostructures of the ensemble amplifier. The array of reaction sites includes a first sub-array of reaction sites and a second sub-array of reaction sites. The ensemble amplifiers of the first sub-array are configured to preferentially respond to a first polarized excitation light. The ensemble amplifiers of the second sub-array are configured to preferentially respond to a second polarized excitation light. The method also includes illuminating the array of reaction sites with the first polarized excitation light and detecting light emissions from the first sub-array. The method also includes illuminating the array of reaction sites with the second polarized excitation light and detecting light emissions from the second sub-array.

In one or more aspects, the structured substrate includes reaction cavities that form the reaction sites. The reaction cavities extend a depth into the structured substrate. Each of the reaction cavities has the corresponding ensemble amplifier therein.

In one or more aspects, the ensemble amplifiers of the first sub-array have a dipole moment that is essentially parallel to a polarization of the first polarized excitation light and the ensemble amplifiers of the second sub-array have a dipole moment that is essentially parallel to a polarization of the second polarized excitation light.

In one or more aspects, the light emissions include fluorescence.

In one or more aspects, the reaction sites are covered by a gel material that is configured to hold biomolecules.

In an embodiment, a method of manufacturing a structured substrate is provided. The method includes providing a base layer having a base side, providing a feature layer along the base side, and forming nano-bodies from the feature layer through reactive-ion etching (RIE). The method also includes coating the nano-bodies with a plasmon resonant material and providing a passivation layer over the nano-bodies and the plasmon resonant material.

In an embodiment, a method of manufacturing a structured substrate is provided. The method includes providing a working substrate having a plurality of cavities. The method also includes providing a feature layer that includes nano-bodies along the working substrate. The feature layer fills the cavities. The method also includes removing material within the cavities through reactive-ion etching (ME) to reveal the nano-bodies and providing a passivation layer over the nano-bodies.

In an embodiment, a method of manufacturing a structured substrate is provided. The method includes providing a working substrate having a plurality of cavities, directly depositing a deposition stream onto the base layer a non-orthogonal angle, and transforming the deposited layer into nano-bodies. The method also includes removing the deposited layer from interstitial regions and providing a passivation layer over the nano-bodies.

In an embodiment, a method of manufacturing a structured substrate is provided. The method includes providing a working substrate having a plurality of cavities, depositing a nanoimprint lithography (NIL) material that includes nano-bodies along the working substrate, and imprinting the NIL material to form a non-planar feature layer. The method also includes selectively removing the material to form nano-bodies and providing a passivation layer.

In an embodiment, a method of manufacturing a structured substrate is provided. The method includes providing a working substrate having a base layer and forming an array of nano-bodies along the base layer. The method also includes depositing a plasmon resonant material along the nano-bodies and thermally annealing the plasmon resonant material to form nanoparticles along the nano-bodies. The method also includes providing a passivation layer over the nanoparticles.

Throughout this application various publications, patents and/or patent applications have been referenced. The disclosure of these publications in their entireties is hereby incorporated by reference in this application.

As used herein, the terms "comprising," "including," and "having," and the like are intended to be open-ended, including not only the recited elements, but possibly encompassing additional elements.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the inventive subject matter should, therefore, be determined with reference to the appended claims, along with the full scope of equivalents to which such claims are entitled.

As used in the description, the phrases "in an exemplary embodiment," "in some embodiments," "in particular embodiments," and the like means that the described embodiment(s) are examples of embodiments that may be formed or executed in accordance with the present application. The phrase is not intended to limit the inventive subject matter to that embodiment. More specifically, other embodiments of the inventive subject matter may not include the recited feature or structure described with a particular embodiment.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112 (f) unless and until such claim limitations expressly use the phrase "means for" followed by a statement of function void of further structure.

The following claims recite one or more embodiments of the present application and are hereby incorporated into the description of the present application.

What is claimed is:

1. A method comprising:

providing a structured substrate having an array of reaction sites, each of the reaction sites including a plurality of nanostructures that form an ensemble amplifier that amplifies electromagnetic energy that is incident with the nanostructures of the ensemble amplifier, wherein the array of reaction sites include a first sub-array of reaction sites and a second sub-array of reaction sites, the ensemble amplifiers of the first sub-array configured to preferentially respond to a first polarized excitation light, the ensemble amplifiers of the second sub-array configured to preferentially respond to a second polarized excitation light;

illuminating the array of reaction sites with the first polarized excitation light;

detecting light emissions from the first sub-array;

illuminating the array of reaction sites with the second polarized excitation light; and detecting light emissions from the second sub-array;

where the first polarized excitation light is different than the second polarized excitation light.

2. The method of claim 1, wherein the structured substrate includes reaction cavities that form the reaction sites, the reaction cavities extending a depth into the structured substrate, each of the reaction cavities having the ensemble amplifier of the reaction site therein.

3. The method of claim 1, wherein the ensemble amplifiers of the first sub-array have a dipole moment that is essentially parallel to a polarization of the first polarized excitation light and the ensemble amplifiers of the second sub-array have a dipole moment that is essentially parallel to a polarization of the second polarized excitation light, wherein the first polarized excitation light and the second polarized excitation light differ by about 90°.

4. The method of claim 1, wherein the structured substrate includes reaction cavities that form the reaction sites, the reaction cavities extending a depth into the structured substrate, each of the reaction cavities having the ensemble amplifier of the reaction site therein; and wherein the ensemble amplifiers of the first sub-array have a dipole moment that is essentially parallel to a polarization of the first polarized excitation light and the ensemble amplifiers of the second sub-array have a dipole moment that is essentially parallel to a polarization of the second polarized excitation light.

5. The method of claim 1, wherein the light emissions include fluorescence.

6. The method of claim 1, wherein the reaction sites are covered by a gel material that is configured to hold biomolecules.

7. The method of claim 1, wherein an organic material covers the nanostructures, where the organic material immobilizes a biomolecule within the corresponding reaction site.

8. The method of claim 4, wherein an organic material covers the nanostructures, the organic material configured to immobilize a biomolecule within the corresponding reaction cavity.

9. The method of claim 6, wherein the biomolecules are target nucleic acids.

10. The method of claim 9, further comprising: contacting the structured substrate with at least one fluorescently labeled probe that binds to the target nucleic acids.

11. The method of claim 10, wherein the fluorescently labeled probe is a fluorescently labeled nucleotide.

12. The method of claim 6, wherein detecting light emissions from the first sub-array comprises detection of hybridization of an oligonucleotide probes to the target nucleic acids.

13. The method of claim 6, wherein detecting light emissions from the first sub-array comprises detection of incorporation of a nucleotide or oligonucleotide probes to the target nucleic acids.

* * * * *

UNITED STATES PATENT AND TRADEMARK OFFICE
CERTIFICATE OF CORRECTION

PATENT NO. : 11,466,268 B2
APPLICATION NO. : 17/247731
DATED : October 11, 2022
INVENTOR(S) : M. Shane Bowen et al.

It is certified that error appears in the above-identified patent and that said Letters Patent is hereby corrected as shown below:

On the Title Page

On Page 2, Column 2, Line 6, Item (56) delete "Plasmmon" and insert -- Plasmon --.

In the Specification

On Column 3, Line 5, delete "cavity" and insert -- cavity. --.

On Column 8, Line 57, delete ""FLUORSCENCE" and insert -- FLUORESCENCE --.

On Column 10, Line 33, delete "flurorescent" and insert -- fluorescent. --.

On Column 11, Line 40, delete "4λ," and insert -- 4λ --.

On Column 13, Line 23, delete "(ME)" and insert -- (RIE) --.

On Column 31, Line 1, delete "momentμ" and insert -- moment μ --.

On Column 31, Line 24, delete "nd" and insert -- and --.

On Column 35, Line 63, delete "(ME)." and insert -- (RIE). --.

On Column 36, Line 6, delete "ME" and insert -- RIE --.

On Column 36, Line 20, delete "(ME)" and insert -- RIE, --.

On Column 36, Line 27, delete "ME." and insert -- RIE. --.

On Column 36, Line 29, delete "(ME)" and insert -- RIE --.

Signed and Sealed this
Fourteenth Day of March, 2023

Katherine Kelly Vidal
*Director of the United States Patent and Trademark Office*

CERTIFICATE OF CORRECTION (continued)
U.S. Pat. No. 11,466,268 B2

On Column 39, Line 26, delete "ML" and insert -- NIL --.

On Column 41, Line 40, delete "les" and insert -- lens --.

On Column 41, Line 42, delete "(Si)." and insert -- (S1). --.

On Column 42, Line 44, delete "exchanged," and insert -- exchanged. --.

On Column 49, Line 46-50, delete "In one or more aspects, a device cover may be coupled to the substrate body to form a flow channel between the active side of the substrate body and the device cover. The flow channel is configured to direct a flow of liquid therethrough that flows into the reaction cavities." and insert the same on Column 49, Line 47, as a new paragraph.

On Column 53, Line 55, delete "(ME)" and insert -- (RIE) --.